(12) United States Patent  
Case et al.

(10) Patent No.: US 7,717,952 B2
(45) Date of Patent: May 18, 2010

(54) ARTIFICIAL PROSTHESES WITH PREFERRED GEOMETRIES

(75) Inventors: Brian C. Case, Lake Villa, IL (US); Ram H. Paul, Jr., Bloomington, IN (US); Grant T. Hoffman, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 676 days.

(21) Appl. No.: 11/586,285

(22) Filed: Oct. 25, 2006

(65) Prior Publication Data

US 2007/0100435 A1 May 3, 2007

Related U.S. Application Data

(63) Continuation-in-part of application No. 10/828,716, filed on Aug. 30, 2004, now Pat. No. 7,618,447.

(60) Provisional application No. 60/732,891, filed on Nov. 2, 2005, provisional application No. 60/465,141, filed on Apr. 24, 2003, provisional application No. 60/530,781, filed on Dec. 18, 2003.

(51) Int. Cl.
*A61F 2/06* (2006.01)
(52) U.S. Cl. .................................. 623/1.24; 623/1.26
(58) Field of Classification Search ............... 623/1.24, 623/1.26, 2.11, 2.18, 2.14
See application file for complete search history.

(56) References Cited

U.S. PATENT DOCUMENTS

| | | | | |
|---|---|---|---|---|
| 3,736,598 A * | 6/1973 | Bellhouse et al. | ........... | 623/2.18 |
| 5,139,515 A * | 8/1992 | Robicsek | ................. | 623/1.28 |
| 5,197,979 A * | 3/1993 | Quintero et al. | ............ | 623/1.26 |
| 5,344,426 A | 9/1994 | Lau et al. | ..................... | 606/198 |
| 5,358,518 A | 10/1994 | Camilli | | |
| 5,397,355 A | 3/1995 | Marin et al. | .................. | 623/12 |
| 5,411,552 A | 5/1995 | Andersen et al. | ............... | 623/2 |
| 5,500,014 A * | 3/1996 | Quijano et al. | ............. | 623/1.24 |
| 5,545,215 A * | 8/1996 | Duran | ...................... | 623/1.26 |
| 5,591,197 A | 1/1997 | Orth et al. | ................... | 606/198 |
| 5,607,465 A | 3/1997 | Camilli | ......................... | 623/1 |
| 5,709,707 A | 1/1998 | Lock et al. | ................... | 606/213 |
| 5,713,953 A | 2/1998 | Vallana et al. | ................. | 623/2 |
| 5,733,325 A | 3/1998 | Robinson et al. | ............... | 623/1 |
| 5,755,781 A | 5/1998 | Jayaraman | ..................... | 623/1 |
| 5,824,045 A | 10/1998 | Alt | ................................ | 623/1 |
| 5,836,964 A | 11/1998 | Richter et al. | ............... | 606/194 |
| 5,840,081 A | 11/1998 | Andersen et al. | ............... | 623/2 |
| 5,843,117 A | 12/1998 | Alt et al. | ..................... | 606/194 |
| 5,855,600 A | 1/1999 | Alt | ................................ | 623/1 |
| 5,855,601 A * | 1/1999 | Bessler et al. | .............. | 623/2.38 |
| 5,876,445 A | 3/1999 | Andersen et al. | ............. | 623/11 |
| 5,879,382 A | 3/1999 | Boneau | ......................... | 623/1 |

(Continued)

*Primary Examiner*—Alvin J Stewart
(74) *Attorney, Agent, or Firm*—Buchanan Intellectual Property Office LLC

(57) ABSTRACT

Implantable medical devices, such as intraluminally implantable stents and valves, are provided having certain preferred shapes. Preferably, a portion of the implantable medical device can define a sinus region having a preferred geometry. The sinus region can have one or more preferred geometric configurations described herein, for example to mitigate or prevent thrombosis within a body vessel. The medical device can include a valve means, such as one or more valve leaflets positioned within the sinus region. The implantable medical devices can be delivered from a catheter within a body vessel, and are preferably expandable from a compressed configuration to a radially expanded configuration. The implantable frames can be self-expanding or balloon expandable. Portions of the medical device, such as the implantable frame or a valve leaflet, are optionally coated with one or more bioactive materials.

20 Claims, 29 Drawing Sheets

U.S. PATENT DOCUMENTS

| | | | |
|---|---|---|---|
| 5,907,893 A | 6/1999 | Zadno-Azizi et al. | 29/6.1 |
| 5,957,949 A | 9/1999 | Leonhardt et al. | 606/194 |
| 6,033,398 A | 3/2000 | Farley et al. | |
| 6,053,940 A | 4/2000 | Wijay | 623/1 |
| 6,123,721 A | 9/2000 | Jang | 623/1 |
| 6,129,755 A | 10/2000 | Mathis et al. | 623/1.15 |
| 6,132,460 A | 10/2000 | Thompson | 623/1.15 |
| 6,132,461 A | 10/2000 | Thompson | 623/1.15 |
| 6,146,416 A | 11/2000 | Andersen et al. | 623/1.15 |
| 6,159,237 A | 12/2000 | Alt et al. | 623/1.11 |
| 6,190,406 B1 | 2/2001 | Duerig et al. | 623/1.2 |
| 6,200,336 B1 | 3/2001 | Pavcnik et al. | |
| 6,235,053 B1 | 5/2001 | Jang | 623/1.15 |
| 6,241,763 B1 | 6/2001 | Drasler et al. | |
| 6,280,467 B1 | 8/2001 | Leonhardt | |
| 6,283,990 B1 | 9/2001 | Kanesaka | 623/1.11 |
| 6,287,334 B1 * | 9/2001 | Moll et al. | 623/1.24 |
| 6,312,459 B1 | 11/2001 | Huang et al. | 623/1.15 |
| 6,312,465 B1 * | 11/2001 | Griffin et al. | 623/2.38 |
| 6,315,793 B1 | 11/2001 | Bokros et al. | |
| 6,325,819 B1 | 12/2001 | Pavcnik et al. | |
| 6,328,763 B1 * | 12/2001 | Love et al. | 623/2.15 |
| 6,338,740 B1 * | 1/2002 | Carpentier | 623/2.13 |
| 6,340,366 B2 | 1/2002 | Wijay | 623/1.13 |
| 6,342,067 B1 | 1/2002 | Mathis et al. | 623/1.15 |
| 6,342,070 B1 * | 1/2002 | Nguyen-Thien-Nhon | 623/2.15 |
| 6,348,065 B1 | 2/2002 | Brown et al. | 623/1.16 |
| 6,352,554 B2 * | 3/2002 | De Paulis | 623/1.26 |
| 6,355,056 B1 | 3/2002 | Pinheiro | 623/1.13 |
| 6,440,163 B1 | 8/2002 | Swanson et al. | 623/1.23 |
| 6,458,153 B1 | 10/2002 | Bailey et al. | |
| 6,488,702 B1 | 12/2002 | Besselink | 623/1.15 |
| 6,494,909 B2 | 12/2002 | Greenhalgh | 623/1.24 |
| 6,503,272 B2 | 1/2003 | Duerig et al. | |
| 6,508,833 B2 | 1/2003 | Pavcnik et al. | |
| 6,514,063 B2 | 2/2003 | Acciai et al. | 425/116 |
| 6,558,415 B2 | 5/2003 | Thompson | 623/1.16 |
| 6,572,650 B1 | 6/2003 | Abraham et al. | 623/1.38 |
| 6,582,462 B1 * | 6/2003 | Andersen et al. | 623/1.26 |
| 6,598,307 B2 | 7/2003 | Love et al. | |
| 6,613,086 B1 | 9/2003 | Moe et al. | |
| 6,663,661 B2 | 12/2003 | Boneau | 623/1.11 |
| 6,669,724 B2 * | 12/2003 | Park et al. | 623/1.24 |
| 6,676,698 B2 | 1/2004 | McGuckin, Jr. et al. | |
| 6,678,962 B1 | 1/2004 | Love et al. | |
| 6,730,117 B1 | 5/2004 | Tseng et al. | 623/1.16 |
| 6,786,922 B2 | 9/2004 | Schaeffer | 623/1.15 |
| 6,790,237 B2 * | 9/2004 | Stinson | 623/23.68 |
| 6,821,292 B2 | 11/2004 | Pazienza et al. | 623/1.15 |
| 6,878,162 B2 | 4/2005 | Bales et al. | 623/1.15 |
| 6,958,076 B2 | 10/2005 | Acosta et al. | |
| 6,962,603 B1 | 11/2005 | Brown et al. | 623/1.15 |
| 6,974,474 B2 | 12/2005 | Pavcnik et al. | |
| 6,976,995 B2 | 12/2005 | Mathis et al. | |
| 7,018,403 B1 | 3/2006 | Pienknagura | 623/1.15 |
| 7,018,404 B2 * | 3/2006 | Holmberg et al. | 623/1.26 |
| 7,018,406 B2 * | 3/2006 | Seguin et al. | 623/2.1 |
| 7,025,777 B2 | 4/2006 | Moore | 623/1.15 |
| 7,025,780 B2 | 4/2006 | Gabbay | |
| 7,044,966 B2 | 5/2006 | Svanidze et al. | 623/2.1 |
| 7,060,088 B1 | 6/2006 | Fischell et al. | 623/1.15 |
| 7,101,396 B2 * | 9/2006 | Artof et al. | 623/2.18 |
| 7,118,600 B2 * | 10/2006 | Dua et al. | 623/23.68 |
| 7,125,418 B2 * | 10/2006 | Duran et al. | 623/1.24 |
| 7,128,756 B2 | 10/2006 | Lowe et al. | 623/1.15 |
| 7,128,759 B2 | 10/2006 | Osborne et al. | 623/1.24 |
| 7,147,661 B2 | 12/2006 | Chobotov et al. | 623/1.16 |
| 7,153,324 B2 | 12/2006 | Case et al. | |
| 7,160,320 B2 * | 1/2007 | Duran | 623/1.24 |
| 7,195,641 B2 | 3/2007 | Palmaz et al. | 623/2.18 |
| 7,338,520 B2 * | 3/2008 | Bailey et al. | 623/1.24 |
| 7,347,869 B2 | 3/2008 | Hojeibane et al. | 623/1.24 |
| 7,351,256 B2 | 4/2008 | Hojeibane et al. | 623/1.24 |
| 7,354,455 B2 | 4/2008 | Stinson | 623/23.68 |
| 7,377,938 B2 * | 5/2008 | Sarac et al. | 623/1.26 |
| 7,381,219 B2 | 6/2008 | Salahieh et al. | 623/2.11 |
| 7,445,631 B2 | 11/2008 | Salahieh et al. | 623/2.18 |
| 7,452,371 B2 | 11/2008 | Pavcnik et al. | 623/1.24 |
| 7,524,331 B2 | 4/2009 | Birdsall | 623/2.11 |
| 7,544,207 B2 | 6/2009 | Osborne et al. | 623/2.16 |
| 7,547,322 B2 * | 6/2009 | Sarac et al. | 623/1.24 |
| 2001/0016770 A1 | 8/2001 | Allen et al. | 623/1.15 |
| 2001/0020183 A1 | 9/2001 | Jang | 623/1.15 |
| 2001/0039450 A1 | 11/2001 | Pavcnik et al. | 623/1.24 |
| 2001/0049553 A1 * | 12/2001 | De Paulis | 623/1.24 |
| 2002/0010504 A1 | 1/2002 | Alt | 623/1.15 |
| 2002/0099439 A1 * | 7/2002 | Schwartz et al. | 623/1.24 |
| 2002/0111339 A1 | 8/2002 | Klausener et al. | 514/183 |
| 2002/0123790 A1 | 9/2002 | White et al. | 623/1.14 |
| 2002/0129820 A1 * | 9/2002 | Ryan et al. | 128/858 |
| 2002/0177894 A1 | 11/2002 | Acosta et al. | 623/1.24 |
| 2002/0193871 A1 * | 12/2002 | Beyersdorf et al. | 623/1.26 |
| 2003/0069646 A1 * | 4/2003 | Stinson | 623/23.7 |
| 2003/0093144 A1 | 5/2003 | Jang | 623/1.15 |
| 2003/0139805 A1 * | 7/2003 | Holmberg et al. | 623/1.31 |
| 2003/0144670 A1 | 7/2003 | Pavcnik et al. | |
| 2003/0176914 A1 | 9/2003 | Rabkin et al. | 623/1.15 |
| 2003/0187500 A1 * | 10/2003 | Jansen et al. | 623/1.26 |
| 2003/0208261 A1 * | 11/2003 | Thorpe et al. | 623/1.16 |
| 2003/0220683 A1 | 11/2003 | Minasian et al. | 623/1.15 |
| 2004/0024444 A1 | 2/2004 | Moore | 623/1.15 |
| 2004/0024447 A1 | 2/2004 | Haverich | |
| 2004/0044401 A1 | 3/2004 | Bales et al. | 623/1.22 |
| 2004/0093061 A1 | 5/2004 | Acosta et al. | 623/1.11 |
| 2004/0093073 A1 | 5/2004 | Lowe et al. | 623/1.15 |
| 2004/0102834 A1 | 5/2004 | Nakano et al. | 623/1.15 |
| 2004/0106985 A1 | 6/2004 | Jang | 623/1.16 |
| 2004/0167619 A1 | 8/2004 | Case et al. | |
| 2004/0215333 A1 * | 10/2004 | Duran et al. | 623/1.24 |
| 2004/0225344 A1 | 11/2004 | Hoffa et al. | |
| 2004/0243218 A1 | 12/2004 | Schaeffer | 623/1.15 |
| 2004/0254640 A1 * | 12/2004 | Sutherland et al. | 623/2.13 |
| 2004/0260389 A1 | 12/2004 | Case et al. | |
| 2005/0055079 A1 * | 3/2005 | Duran | 623/1.13 |
| 2005/0059923 A1 * | 3/2005 | Gamboa | 604/9 |
| 2005/0075713 A1 * | 4/2005 | Biancucci et al. | 623/1.11 |
| 2005/0216077 A1 | 9/2005 | Mathis et al. | |
| 2005/0222661 A1 * | 10/2005 | Case et al. | 623/1.1 |
| 2005/0228479 A1 | 10/2005 | Pavcnik et al. | |
| 2005/0234541 A1 | 10/2005 | Hunt et al. | |
| 2005/0234546 A1 * | 10/2005 | Nugent et al. | 623/2.11 |
| 2006/0015178 A1 | 1/2006 | Moaddeb et al. | |
| 2006/0074480 A1 | 4/2006 | Bales et al. | 623/1.15 |
| 2006/0116572 A1 | 6/2006 | Case | |
| 2006/0136045 A1 | 6/2006 | Flagle et al. | |
| 2006/0178729 A1 | 8/2006 | Thielen et al. | |
| 2006/0178730 A1 | 8/2006 | Hill et al. | |
| 2006/0195004 A1 | 8/2006 | Jarvik | |
| 2006/0241744 A1 | 10/2006 | Beith | |
| 2006/0271159 A1 | 11/2006 | Gregorich et al. | 623/1.15 |
| 2006/0276882 A1 | 12/2006 | Case et al. | |
| 2006/0287717 A1 * | 12/2006 | Rowe et al. | 623/2.11 |
| 2007/0260327 A1 * | 11/2007 | Case et al. | 623/23.68 |
| 2008/0082166 A1 * | 4/2008 | Styrc et al. | 623/2.18 |
| 2008/0249619 A1 * | 10/2008 | Stacchino et al. | 623/2.11 |
| 2009/0082858 A1 * | 3/2009 | Nugent et al. | 623/2.18 |
| 2009/0088836 A1 * | 4/2009 | Bishop et al. | 623/2.1 |
| 2009/0099653 A1 * | 4/2009 | Suri et al. | 623/2.11 |
| 2009/0240320 A1 * | 9/2009 | Tuval et al. | 623/1.24 |
| 2009/0248132 A1 * | 10/2009 | Bloom et al. | 623/1.15 |
| 2009/0270965 A1 * | 10/2009 | Sinha et al. | 623/1.11 |

* cited by examiner

ARTIFICIAL PROSTHESES WITH PREFERRED GEOMETRIES

RELATED APPLICATIONS

This application claims the benefit of U.S. Provisional Patent Application 60/732,891, filed Nov. 2, 2005 by Case et al., which is incorporated herein by reference in its entirety. This application is also a continuation-in-part of presently U.S. patent application Ser. No. 10/828,716, filed Aug. 30, 2004 now U.S. Pat. No. 7,618,447 and entitled, "Artificial Valve Prosthesis with Improved Flow Dynamics," by Case et al., which in turn claims priority to U.S. Provisional Applications Nos. 60/465,141, filed Apr. 24, 2003, and 60/530,781, filed Dec. 18, 2003. All of the above-referenced patent applications are incorporated by reference herein in their entirety.

TECHNICAL FIELD

The present invention relates generally to the field of intraluminally implantable devices, including stents and valve support frames. More particularly, this invention relates to intravascular valve prostheses.

BACKGROUND

Intraluminally implantable frames are being implanted in increasing numbers to treat a variety of conditions, and are coming into greater use in a variety of fields. Frames implanted in vessels, ducts or channels of the human body can form part of a valve to regulate fluid flow within a body lumen or as scaffolding to maintain the patency of the vessel, duct or channel lumen. Implantable frames can also support a valve or valve leaflets for regulating fluid flow within a body lumen or for dilating a body lumen. One or more flexible valve leaflets can be attached to an implantable frame to form a medical device useful as an artificial valve. A variety of other implantable prostheses, such as stents, grafts and the like, also comprise an implantable frame placed within the body to improve the function of a body lumen.

The venous system includes a series of valves that function to assist the flow of blood returning to the heart. These natural valves are particularly important in the lower extremities to prevent blood from pooling in the lower legs and feet during situations, such as standing or sitting, when the weight of the column of blood in the vein can act to prevent positive blood flow toward the heart. This condition, commonly known as chronic venous insufficiency, is primarily found in individuals in which gradual dilation of the veins, thrombotic events, or other conditions prevent the leaflets of the native valves from closing properly. The failure of native valves to properly close can worsen, leading to significant leakage of retrograde flow such that the valve can become incompetent. Chronic venous insufficiency is a condition in which the symptoms can progress from painful edema and unsightly spider or varicose veins to skin ulcerations. Elevation of the feet and compression stocking can relieve symptoms, but do not treat the underlying disease. Untreated, the disease can impact the ability of individuals to perform in the workplace or maintain their normal lifestyle.

One promising approach to treating venous valve insufficiency includes the implantation of self-expanding or radially-expandable artificial valves that can be placed using minimally invasive techniques. One common problem evident from early prosthetic valves is the formation of thrombus around the base of the leaflets, possibly due at least in part to blood pooling in that region. In a natural valve, the leaflets are typically located within a sinus or enlargement in the vein. The pockets formed between the leaflets and the walls of the sinus can create vortices of flowing blood that help flush the pocket and prevent blood from stagnating and causing thrombosis around the valve leaflets, which can interfere with the function of the valve. Stagnating blood may restrict oxygen from reaching the endothelium covering the valve cusps, leading to hypoxia of the tissues which may explain increased thrombus formation typical in that location. Expandable-frame valve prostheses are typically cylindrical in shape and lack an artificial sinus or pocket space that is sufficient for simulating these natural blood flow patterns.

What is needed is an intraluminally-placed medical device, such as an artificial valve or stent, that is configured to create more desirable flow patterns around a valve within a body, for instance to circulate the blood or bodily fluids and reduce the likelihood of stagnation and the potential clinical problems that may result. Implantable devices that have structural adaptations resulting in the formation of sinus regions within a body vessel can create beneficial fluid flow conditions such as more turbulent flow, increased velocity of flow, larger and/or more numerous vortices, other factors, or a combination of the above that can mitigate the incidence of thrombosis formation near the implantable medical device.

SUMMARY

The present invention relates to implantable medical devices, and methods of manufacturing and using the same. Preferably, the medical device is configured as a venous valve, having one or more valve leaflets attached to an expandable support structure that defines a sinus region within a body vessel. The sinus region preferably has a geometry that desirably facilitates fluid flow within the body vessel near a valve, for example to mitigate or prevent thrombus formation. For example, the sinus region can have a size or shape to facilitate flow patterns or fluid vortices to facilitate clearing of the blood or other bodily fluid that would otherwise pool in or near the valve structure. The modification of fluid flow in the sinus region can desirably contribute to the closure of valve leaflets when the valve is closed, for example to form a seal and prevent leakage of fluid back through the closed valve. The implantable medical device preferably forms a sinus region within a body vessel that can beneficially function in ways similar to natural sinus regions formed proximate to natural valves in the deep veins of the lower legs. Implantable prostheses adapted to create a preferred geometry sinus region can be used, for example, to improve the function of incompetent natural valves or in combination with implantable prosthetic valve structures.

An implantable medical device defining a sinus region is preferably configured to function as an implantable valve. The implantable valve can define an interior lumen and have at least one valve leaflet moveably positioned within the interior lumen. The valve leaflet can include a flexible free edge that defines a portion of a valve orifice. The valve leaflet can move between an open position and a closed position. In the open position, the valve leaflet can permit fluid to flow through the valve orifice and through the interior lumen in a first direction. In the closed position, the valve leaflet can substantially prevent the flow of fluid through the valve orifice. The flexible free edge can move between the open and closed position responsive to a change in the pressure and/or direction of fluid flow contacting the valve leaflet. Preferably, an implantable valve includes one, two or three valve leaflets, each comprising a free edge cooperatively defining the valve orifice. Also preferably, the implantable valve is moveable between a compressed state for delivery using a transcatheter percutaneous method, and an expanded state after deployment within a body vessel. The implantable valve can include a self-expanding frame, such as a frame formed from a superelastic nickel-titanium alloy, or a balloon-expandable frame, such as a frame formed from stainless steel or cobalt-chromium alloy.

The implantable medical device can define a sinus region having certain preferred dimensional characteristics. The frame typically defines a lumen extending between a proximal end and a distal end along a longitudinal axis. Preferably, the frame includes a substantially annular distal frame end with a first diameter at the distal end and a sinus-forming frame portion proximal to the distal end, the sinus-forming frame portion having a maximum diameter of about 10% to about 200% larger than the first diameter, and most preferably about 60-70% greater. The maximum diameter of the frame is preferably positioned between the distal and proximal end of the frame such that the longitudinal distance from the distal end to the maximum diameter of the sinus-forming frame portion is less than the longitudinal distance from the proximal end to the distal end of the frame. In one aspect, the longitudinal distance from the distal end of the frame to the longitudinal position of the maximum diameter of the sinus-forming frame portion is about 30-40% of the distance between the distal end of the frame to the proximal end of the frame. In another aspect, the maximum diameter of the sinus region is approximately equal to a distance measured along the longitudinal axis of the frame from the free edge of the valve leaflet to the distal end of the sinus region. The frame is preferably radially moveable from a compressed state to a radially expanded state. Optionally, the frame further includes a bioactive material releasably attached to at least a portion of the implantable valve.

The valve leaflet may be attached to the frame within the lumen in a manner defining a sinus region within the lumen between the valve leaflet and the frame. Preferably, the valve leaflet includes a remodelable material, such as an extracellular matrix material. The valve leaflet may have a length measured from a base attached to the frame to a flexible free edge moveable in response to fluid flow through the lumen. In one aspect, the distance measured along the longitudinal axis of the frame from the base of the valve leaflet to the maximum diameter of the sinus region is equal to between about 50% and 150% of the length of the value leaflet. The distance measured along the longitudinal axis of the frame from the maximum diameter to the distal end of the sinus region may be between about 10% and about 200% of the leaflet length.

In another embodiment, methods of manufacturing a valve, such as a venous valve, are provided. The methods of manufacture preferably include the steps of: providing a frame defining a lumen extending between a proximal end and a distal end along a longitudinal axis, the frame comprising a substantially annular distal frame end with a first diameter at the distal end and a sinus-forming frame portion proximal to the distal end, the sinus-forming frame portion having a maximum diameter of about 10% to about 200% larger than the first diameter; and attaching a valve leaflet comprising an extracellular matrix material to the frame within the lumen, the valve leaflet configured and positioned to define a sinus region within the lumen between the valve leaflet and the frame, the valve leaflet having a length measured from a base attached to the frame to a flexible free edge, the free edge moveable in response to fluid flow through the lumen. Preferably attaching the valve leaflet reduces the radius of the frame in at least one direction.

Other embodiments relate to methods of treating conditions, such as a venous valve related condition. The methods of treatment may include the steps of: providing an implantable valve comprising: a frame defining a lumen extending between a proximal end and a distal end along a longitudinal axis, the frame comprising a substantially annular distal frame end with a first diameter at the distal end and a sinus-forming frame portion proximal to the distal end, the sinus-forming frame portion having a maximum diameter of about 10% to about 200% larger than the first diameter; and a valve leaflet attached to the frame within the lumen, the valve leaflet defining a sinus region within the lumen between the valve leaflet and the frame, the valve leaflet having a length measured from a base attached to the frame to a flexible free edge, the free edge moveable in response to fluid flow through the lumen; introducing the implantable valve within a body vessel in the radially compressed configuration; positioning the implantable valve at a point of treatment within the body vessel; and radially expanding the intralumenal medical device at the point of treatment to the radially expanded configuration in a manner effective to place the frame in contact with the wall of the body vessel. Preferably, the frame is a self-expanding frame and the valve leaflet comprises an extracellular matrix material, the method further comprising the steps of: selecting a frame having a maximum diameter that is at least 10% larger than the diameter of the body vessel at the point of treatment.

While the invention is defined by the claims appended hereto, additional understanding of the invention can be gained by reference to the attached drawings and the description of preferred embodiments presented below.

BRIEF DESCRIPTION OF THE DRAWINGS

Embodiments of the present invention will now be described by way of example with reference to the accompanying drawings, in which.

DETAILED DESCRIPTION

Figure 1:
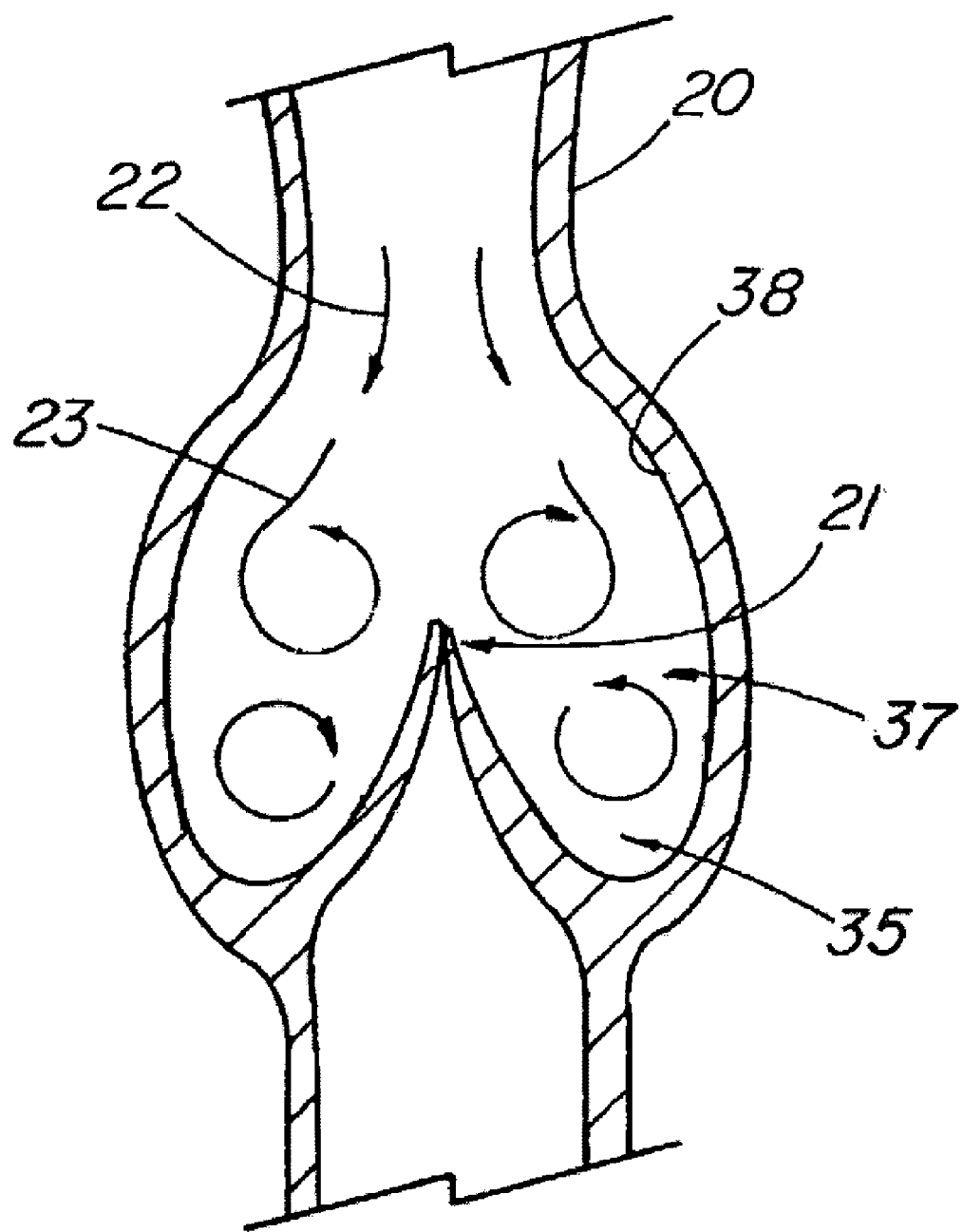
FIG. 1 depicts a cross-sectional view of a native venous valve and retrograde blood flow pattern.

The terms "implantable frame" and "frame" are used interchangeably to refer to the structures disclosed herein. Preferably, the frames are configured for implantation within a body vessel.

The terms "proximal" and "distal" are used to connote a direction or position relative to each other. Unless otherwise indicated, the recitation of "proximal" or "distal" portions of a frame does not refer to any particular orientation of the implantable frame within a body. The implantable frames described herein can be used in many different body lumens, including both the arterial and venous system, and can be implanted in any suitable orientation within the body.

The term "circumferential" or "circumferentially" refers to a direction or displacement measured along the exterior surface area of an assembled implantable frame in the expanded state that is transverse to the longitudinal axis of the implantable frame. A first structural feature "circumferentially adjacent" to a second structural feature means that the first structural feature is the nearest first structural feature to the second structural feature when moving circumferentially along the exterior surface of an implantable frame. The term "circumferential distance" means distance measured along the exterior surface of an implantable frame in the expanded state.

The term "longitudinal" or "longitudinally" refers to a direction measured along the longitudinal axis of the implantable frame. The term "longitudinally adjacent" means positioned in a distal or proximal direction along the exterior surface of an implantable frame parallel to the longitudinal axis of the implantable frame. The term "longitudinal distance" means a distance or displacement measured parallel to the longitudinal axis of an implantable frame in the expanded state, measured along the exterior surface area of the implantable frame.

As used herein, the term "strut" refers to a substantially straight portion of a frame, while the term "bend" refers to an arcuate portion of the frame.

As used herein, the terms "peak" and "valley" are used interchangeably to refer to bends in portions of a frame.

As used herein, the term "symmetrically positioned" refers to a similarity in size, shape, or relative position of corresponding parts.

As used herein, the term "sinus" refers to a portion of a body vessel having a lumen with a larger diameter than the lumen of the body vessel proximal to and/or distal to the sinus. The sinus in a vein can have a bulbous longitudinal cross sectional shape. A sinus can be formed in a body vessel naturally, such as a vein sinus proximate to a venous valve, or a sinus may be formed in a body vessel by implanting a medical device.

As used herein, the term "attachment pathway" refers to the contact interface between a valve leaflet and one or more struts and/or vessel walls. The attachment pathway can define the shape and configuration of the plurality of leaflets comprising the valve structure as deployed.

In one aspect, the collapsible support structure of the valve is expandable to a particular diameter upon deployment, with the valve being configured such that the medical device creates an artificial sinus supporting a portion of a body vessel. The sinus can be defined in part by an unsupported portion of the vessel.

FIGS. 2-9 and FIGS. 11-23 show examples of collapsible, self-expanding or otherwise radially expandable artificial valve 10 that can be deployed within a bodily passageway 20, such as a vessel or duct, of a patient typically delivered and implanted using transcatheter techniques for delivery of self-expanding prostheses. The valve 10 can have a first or proximal end 13 and a second or distal end 14, with the normal, antegrade fluid flow typically traveling from the distal end to proximal end of the medical device, the latter being located closest to the heart in a venous valve when placed within the lower extremities of a patent. The valve 10 comprises a support structure 11 and a valve structure 12, such as the illustrative valve structure, attached to the support structure and configured to selectively restrict fluid flowing therethrough by closing with changes in the fluid pressure differential, such as in the presence of retrograde flow. Preferred embodiments relate to structural features that mimic the natural valve configuration of FIG. 1, for example by modifying the flow dynamics within the medical device such that fluid collecting in pockets 35 near the base of the leaflets 26 can be flushed away or effectively mixed with fresher incoming bodily fluid on a continual basis.

Referring to the implantable prosthetic valve devices shown in FIGS. 2-8, the support structure 11 can be configured such that when the device can be deployed within the bodily passage 20, such as a vein of the lower legs or feet, an artificial sinus 34 can be formed adjacent to and surrounding the valve structure 12 such that the blood or other bodily fluids collecting within the pockets 35 formed around the bases of the valve leaflets 26 can be more likely to be flushed out on a continual basis due to the advantageous geometry created by the artificial sinus 34. The principle can be illustrated in the example of FIG. 1 which shows a natural venous valve 21 in which retrograde blood 22 flowing or falling back down and closing the valve can be thought to create a series of vortices 23 as it contacts the leaflets. It is believed that the rounded shape of the enlarged natural sinus 37 surrounding the valve 21 facilitates creation of these vortices, thereby preventing blood from pooling or stagnating within the pockets 35 at the base of the valve 21, which may lead to thrombus formation or other problems. With respect to FIGS. 2-8, the support structure 11 is preferably configured to create an artificial sinus 34 similar to the natural sinus 37 in the vein.

In one exemplary embodiment, the expandable support structure comprises a first, proximal portion and a second, distal portion that are interconnected by one or more thin members or struts, such that the largely unsupported region between the first and second (proximal and distal) sections of the support structure forms an artificial sinus (proximal is typically toward the heart in a venous valve). The valve structure can be attached to the support structure such that it the valve structure can be substantially positioned within the artificial sinus. For example, the valve structure (defined herein to include one or more cooperating leaflets, tubular members, or other flexible structure adapted to restrict fluid flow in a passageway in response to changing fluid pressure differentials thereacross) may be attached to the interconnecting members, which can comprise oppositely placed struts having attachment points (e.g., suture or any suitable structure or method) to facilitate attachment of the valve material.

Figure 2:
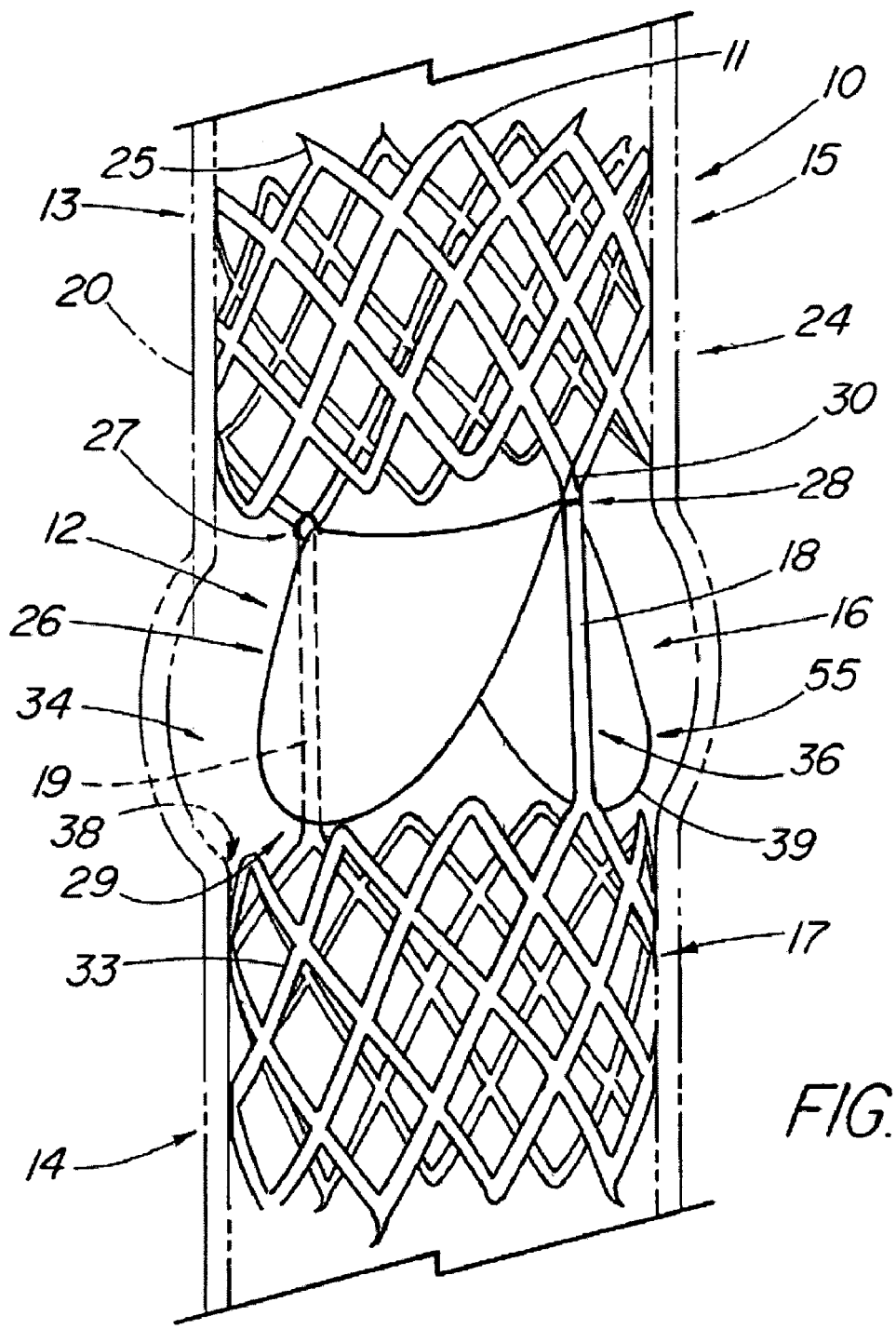
FIG. 2 depicts a schematic view of an illustrative embodiment of the present invention in which the medical device includes interconnecting proximal and distal sections defining an intermediate, substantially open section for creating an artificial sinus in the vessel.

FIG. 2 depicts a side view of an illustrative embodiment in which the medical device 10 includes a first or proximal section 15 and a second or distal section 17 that are spaced apart from one another, defining an intermediate, substantially open section 16 for creating the artificial sinus 34 in the vessel 20. The term "substantially open" is used herein to define a largely unsupported portion of the bodily passage in which at least some minimal interconnecting structure (e.g., thin or flexible elements aligned with the leaflet commissures) traverses the unsupported portion of the bodily passage, but it comprises very limited surface area and typically supplies minimal, if any, force against the walls of the passageway lateral to the valve structure 12. The proximal and distal sections 15,17, which preferably comprise a pair of radially expandable or self-expanding anchoring portions 24, are joined by an interconnecting means 36, such as the illustrative pair of connection struts 18,19 that allows the intermediate section 16 to be otherwise open and free of scaffolding so that the vein walls 38 along that section of the vessel 20 are able to expand due to pressure exerted by the blood flowing within the vein. The anchoring portions 24 can function as stents to help the bodily passage remain patent. The support structure 11 and anchoring portions 24 also may be configured to be readily collapsible as with a normal vein. Since the diameters of the proximal and distal sections 15, 17 generally assume a fixed diameter after deployment, the intermediate section, which can be substantially unsupported or covered by structure, can expand to form a bulging region of a vein that expands to form an artificial sinus 34 between pulses of blood flow. Although the interconnecting means 36 advantageously permit the proximal and distal sections 15, 17 to be deployed together at a fixed distance from one another, the valve 10 can also comprise separate unconnected sections that are deployed sequentially at an effective distance from one another to create an artificial sinus 34 therebetween. Additionally, the interconnecting means 36 can comprise suture, fabric, or some other non-rigid material to join the proximal and distal sections 15,17 and define the optimal length of the intermediate section 16, without interfering with the creation of the artificial sinus 34. To deploy a medical device 10 having a flexible interconnecting means 36, one of either the proximal or the distal sections 15,17 can be deployed first with the delivery system then being slowly withdrawn until the interconnecting means 36 becomes taut, whereby the opposite section can be then deployed.

In the illustrative embodiment of FIG. 2, the valve structure 12 comprises a pair of leaflets 26 that are situated in the intermediate section. Optionally, the valve structure 12 can comprise one, three, four, five, six or more leaflets 26. The leaflets 26 can be attached to the proximal section 15 at two or more commissural points 27,28, each located at the proximal ends of the interconnecting struts 18,19, using an appropriate attachment means 30, such as suture, adhesive, fasteners, tissue welding using heat and/or pressure, and the like. The leaflets 26 can be attached about their distal ends 29 to the distal section 17 of the support structure 11 using the same or another suitable attachment means 30. Alternatively, the leaflets 26 can be formed by a tube-shaped material attached around the outside of the distal section 15 and to the connection struts 18, 19. The proximal edge of the tube-shaped material can thereby form opposable leaflet free edges between the connection struts 18, 19.

Figure 3:
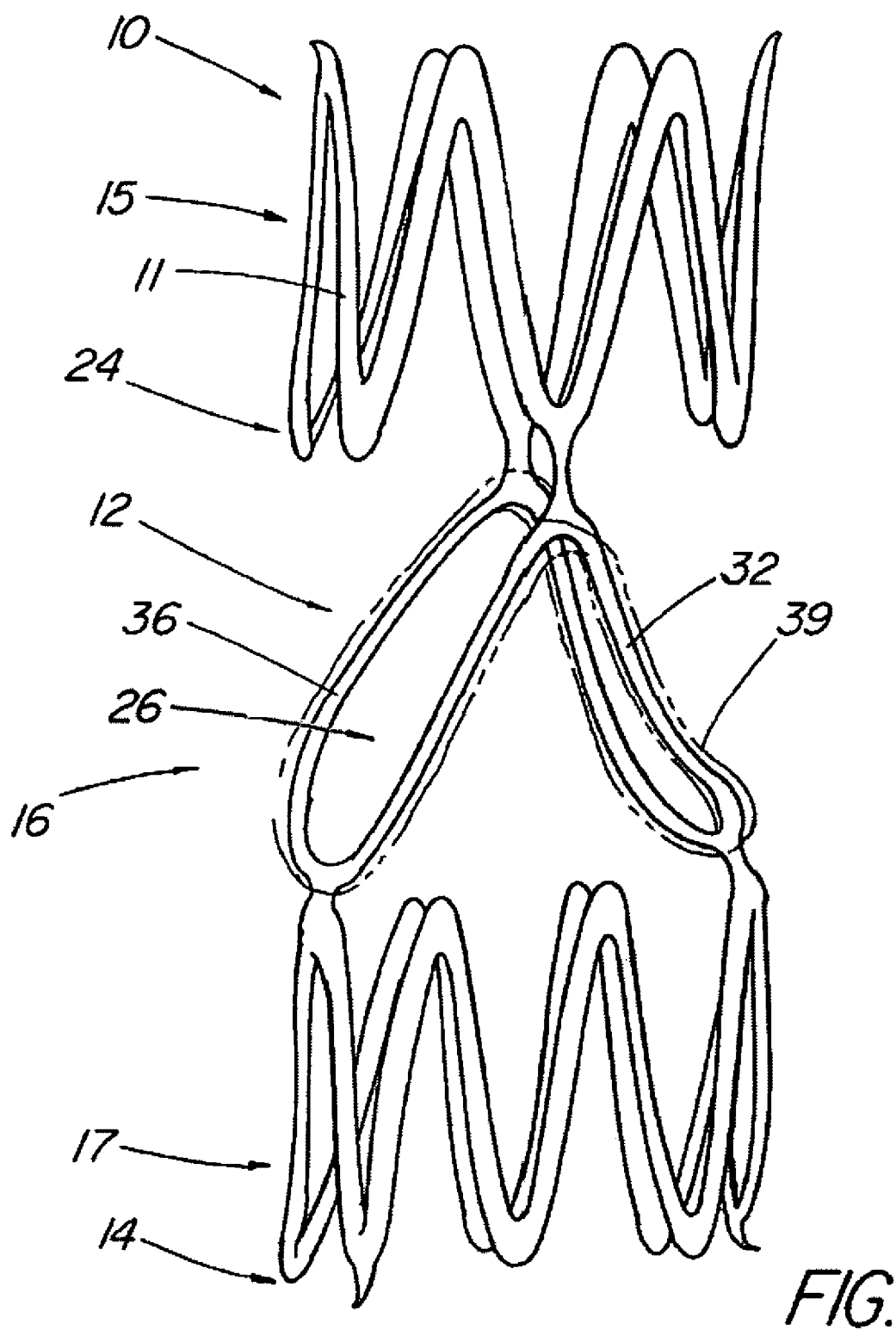
FIG. 3 depicts a schematic view of a second illustrative embodiment of the present invention in which the proximal and distal sections are interconnected by a frame that can be incorporated into the valve structure of the medical device.

Referring to the embodiment shown in FIG. 3, the frame 32 also serves as the interconnecting means 36 between the proximal and distal section 15,17 of the support structure 11, with the struts being laser cut (for example) from the same tube used to form the remainder of the support structure 11. The frame 32 can be formed by any method suitable for the material being used, including laser cutting, weaving, welding, molding, and the like. Preferably, the valve structure 12 can be configured so that it advantageously expands with the deployment of the proximal and distal sections 15, 17 such that the outer edges 39 thereof contact the vessel wall sufficiently to at least substantially prevent leakage of bodily fluid around the valve structure 12. Optionally, the wall-engaging outer edges of the leaflets 26 can be reinforced with a separate frame 32 that can be attached to or incorporated into the outer edges to improve sealing with the vessel wall. The valve frame 32 (that portion of the support structure 11 that reinforces the valve structure 12) can either be configured to exert relatively little radial force beyond what might be required to ensure adequate contact with the vessel wall, or it may be configured such that the frame 32 exerts sufficient radial force such that it assists in creating an artificial sinus in the portion of the vein along the intermediate section 16 of the valve 10.

In another aspect, the proximal end of the collapsible support at which the valve structure can be located is radially expanded (e.g. flared outward) such that the expanded end or a combination of the expanded end and adjacent area of the vein forms the artificial sinus. The expandable support structure of the valve can include a framework or anchoring portion having an intermediate region that includes an enlarged diameter configured to create an artificial sinus about the valve structure, which can be attached inside the intermediate region. In one embodiment, the support structure can be made of a superelastic material, such as nitinol, and the intermediate region comprises an expanded or bulging portion that can be formed by heat setting the nitinol tubular frame around a mandril or other fixture of the desired configuration using a method well known in the medical arts. The intermediate portion can expand to a diameter larger than the proximal and distal portions when the medical device can be deployed from the delivery system, thereby producing larger pockets around the valve structure which create more effective flow patterns to reduce pooling.

Figure 4:
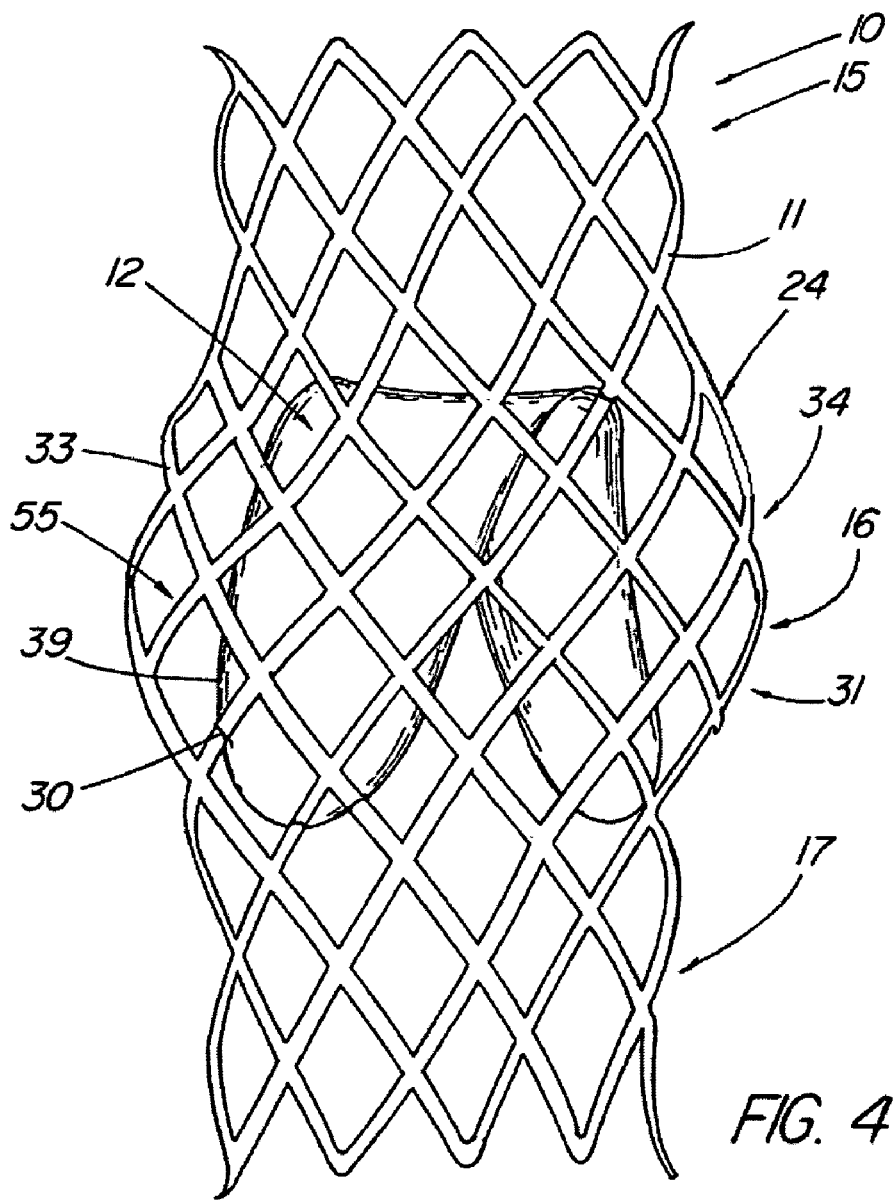
FIG. 4 depicts a schematic view of an illustrative embodiment of the present invention in which the intermediate section of the medical device comprises an expanded portion of the support structure.
Figure 5:
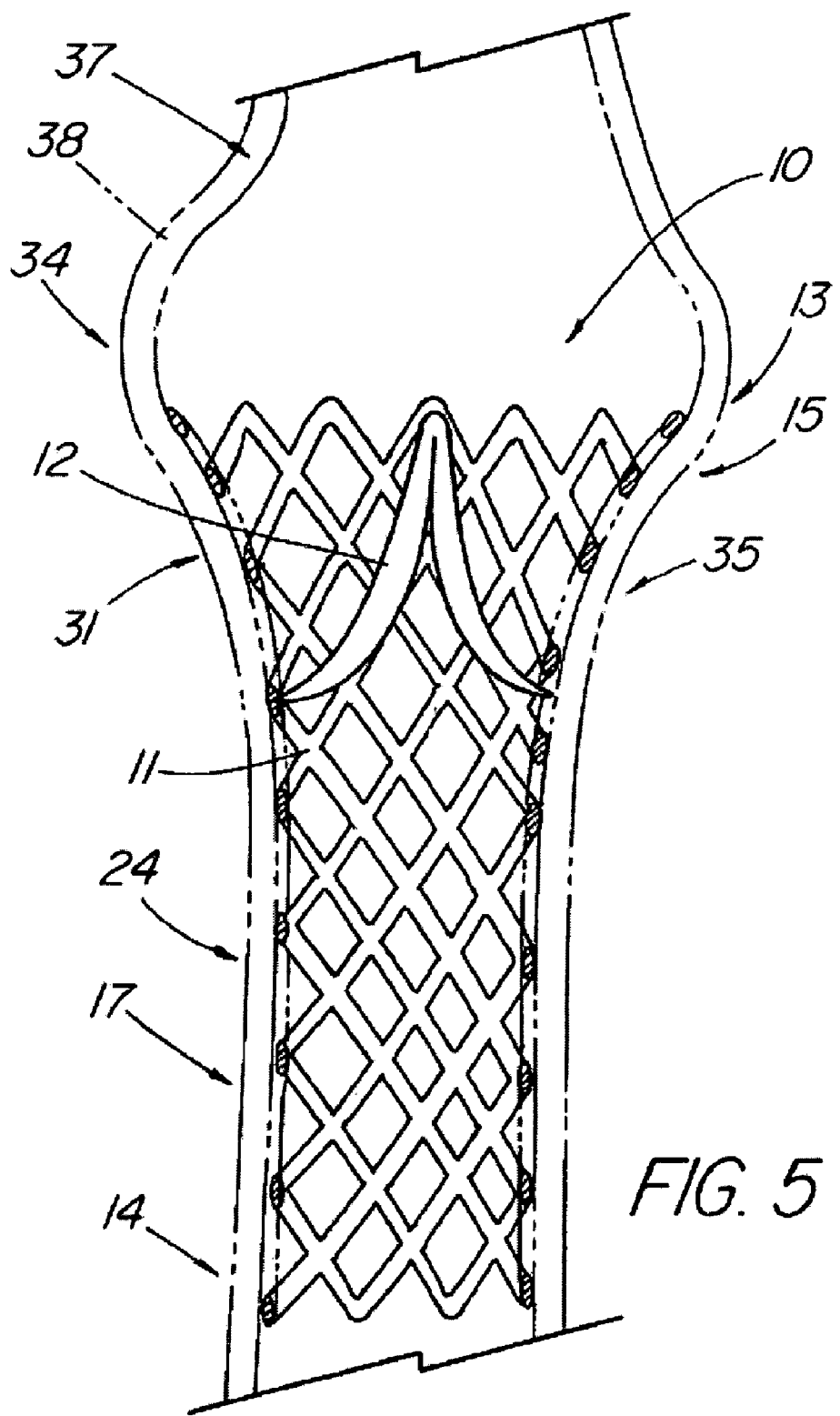
FIG. 5 depicts a schematic view of an illustrative embodiment of the present invention in which the proximal end can be expanded to create an artificial sinus about the valve structure.

FIGS. 4-5 depict implantable prosthetic devices wherein the support structure 11 includes an expanded portion 31, larger in diameter than the remainder of the support structure 11 that upon deployment can create an artificial sinus 34 surrounding the valve structure 12. The diameter of the artificial sinus 34 caused extending the vessel wall 38 is, at its widest point, is preferably about 10-200% larger than the diameters of the proximal and distal sections 15,17 when fully deployed (unrestrained from within the delivery sheath), with a more preferred differential of about 30-120%, more preferably difference of 40-80% larger and most preferably about 60% larger, depending on the diameter of the vein, the valve structure geometry, fluid column pressures at that location, and other factors. In the illustrative embodiments, the transition between the proximal and distal section 15,17 and the expanded intermediate section 16 can be curvilinear, creating a bulge-like or flared configuration (FIGS. 4 and 5, respectively). In the examples depicted, the support structure can comprise a single tubular anchoring portion 24 that can be plastically, resiliently, or otherwise deformed into a second configuration that includes the expanded portion 31. For example, the anchoring portion 24 can be laser cut from a tube of nitinol, placed around a mandril having the desired shape, and heat set to produce the final desired shape. In the embodiment of FIG. 4, the expanded portion 31 comprises the intermediate section 16 of the medical device 10, such that the artificial sinus 34 can be created between the proximal and distal sections 15, 17 and the valve structure 12 can be located therein. In FIG. 5, the expanded portion 31, which comprises the proximal section 15 of the support structure 11, includes a flared configuration that extends outward from the distal section 17 (no separately functional intermediate section 16 is present). Preferably, the flared configuration defines at least a portion of a sinus region having a maximum diameter equal to the maximum diameter of the expanded portion 31, upon implantation in a body vessel. The valve structure 12 can be attached about the proximal end 13, while the flared, expanded portion 31 thereabout causes the vessel 20 to bulge outward, thus creating an artificial sinus 34 about the proximal end of the medical device 10. The artificial sinus 34 comprises a combination of a supported and an unsupported portion in the embodiment of FIG. 5. In both illustrative embodiments the valve structure 12 can be sewn to the struts 33 of the support structure within the passageway of the anchoring portion 24. Other alternative methods of attachment include adhesives, staples or other fasteners, wire, engagement barbs on the frame, tissue welding, etc.

In another embodiment, the proximal, distal, and intermediate sections can be separate, interconnected sections, such as zig-zag frame or other expandable or self-expanding support or anchoring frames. The intermediate section comprising the artificial sinus can include a first and a second radially expandable or self-expanding portion in which the adjoining ends of each are larger in diameter than the ends which adjoin the proximal and distal sections, respectively. The frustoconical shape of the respective intermediate sections can be accomplished, for example, by forming the section into that shape (i.e., plastic deformation of a tubular medical device, heat setting nitinol, laser cutting a frustoconical section of tubing, etc.) or a constraining means, such as a suture or thin wire, can be used to manipulate the relative diameters by feeding the constraining means through the apices of the bend or apertures therein and applying the appropriate amount of tension to create the desired shape. Optionally, a tubular or band-like section can be positioned between opposing frustoconical sections to create a longer artificial sinus.

Figure 6:
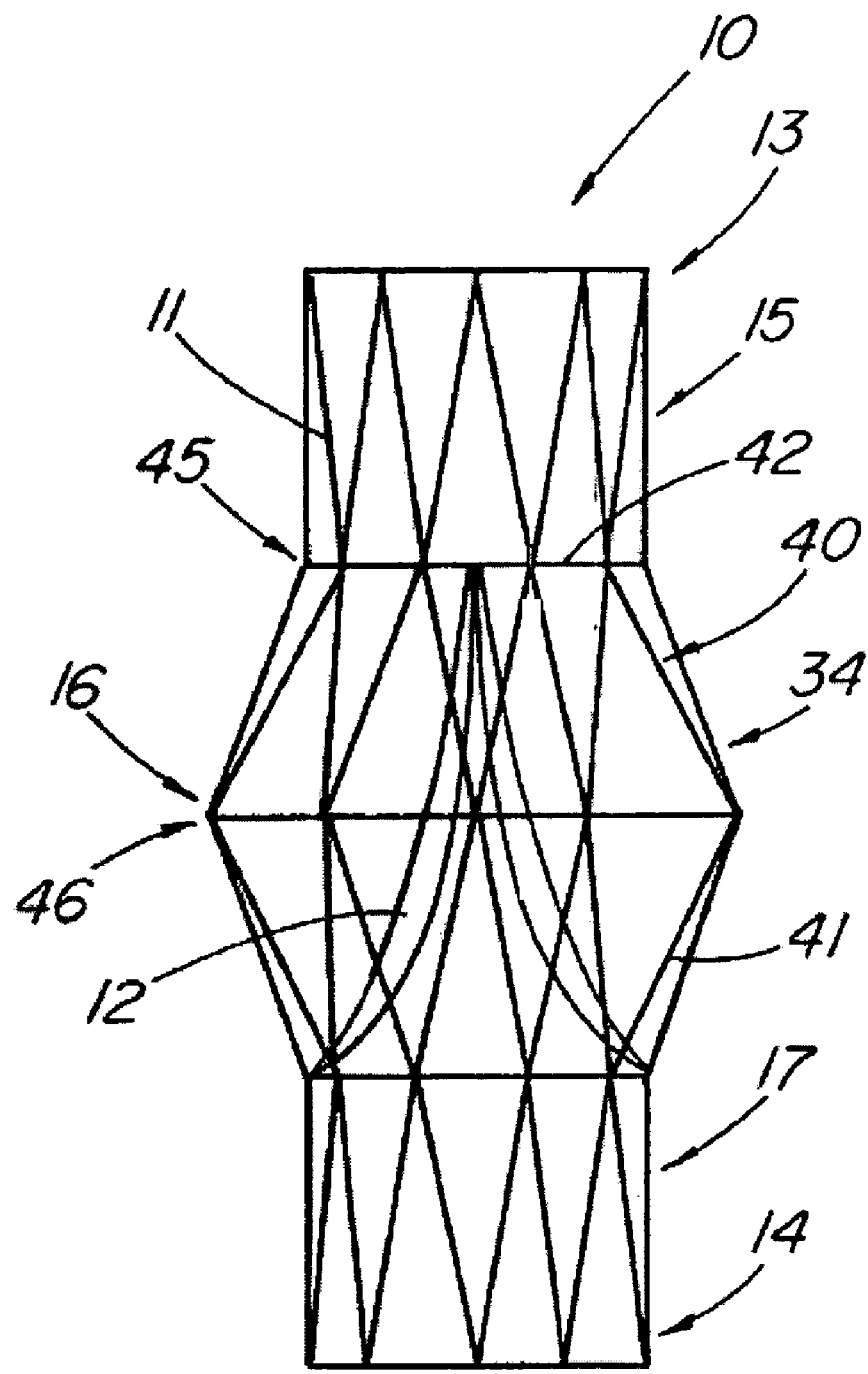
FIGS. 6-7 depict side views of embodiments of the present invention in which artificial sinus comprises a plurality of separate support sections.
Figure 7:
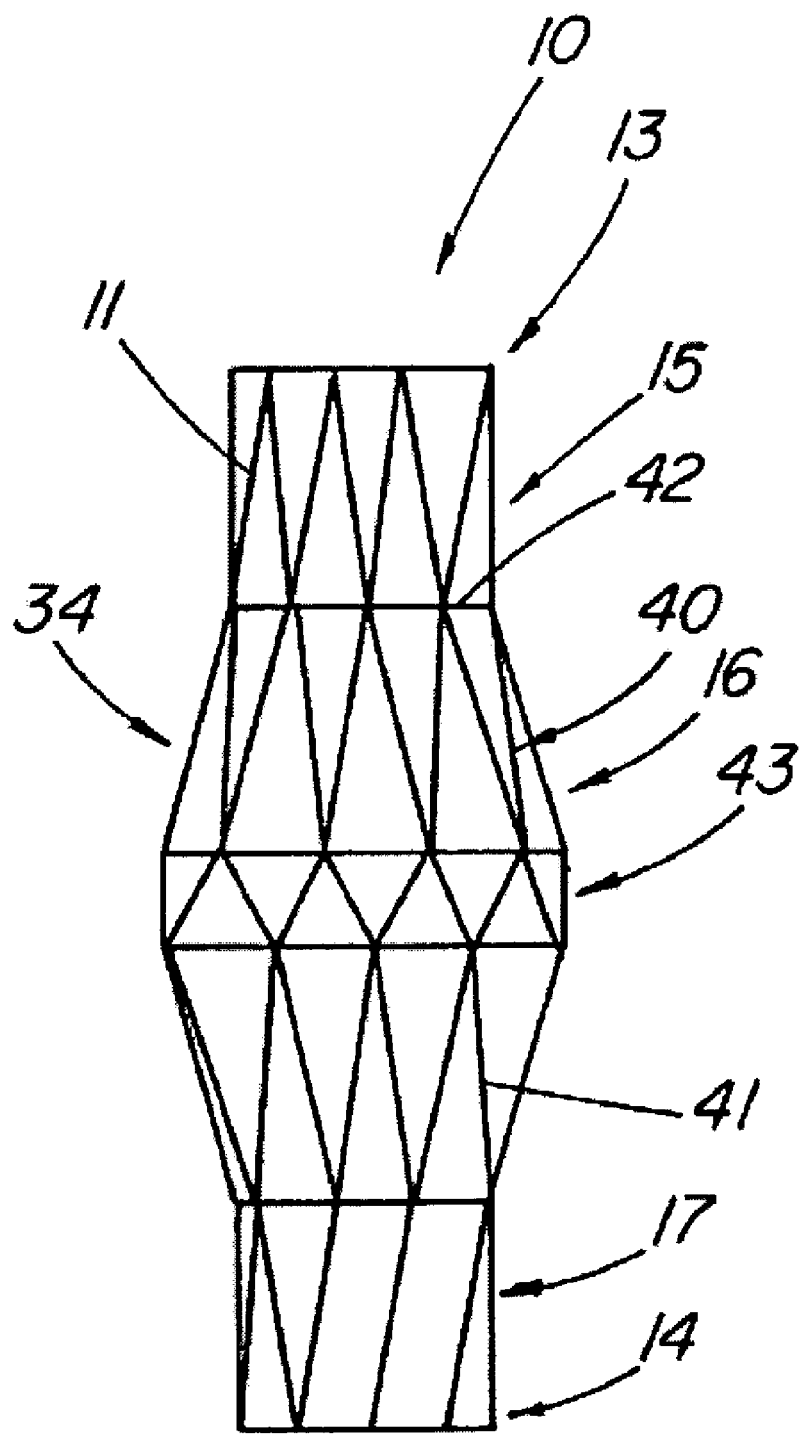

FIGS. 6-7 depict embodiments similar to that of FIG. 5, except that the proximal, intermediate, and distal sections 15, 16, 17 comprise separate anchoring portions (having a serpentine or "zig-zag" configuration in the illustrative embodiment) that are attached to one another in any suitable manner, such as by feeding a constraining means 42, such as the illustrative thread material or suture, through the apices 45 of adjoining bends and securing it therearound. In the embodiment of FIG. 6, the intermediate section 16 comprises a first and a second intermediate subsection 40, 41 of opposing frustoconical-shaped anchoring portion that are coupled to form the artificial sinus 34. The first and second subsections 40, 41 can be manipulated into a frustoconical shape by plastically deforming the anchoring portion into that shape, or by increasing constraint of the frame about the distal end of a cylindrical-shaped proximal portion 15 and the proximal end of a cylindrical-shaped distal portion 17 with a constraining means 42, such as thread, suture, wire, band, covering, etc., so that the respective sections 15, 17 assume a frustoconical shape. Additional constraining means 42 may be included at the first and second ends 13, 14, as depicted, to maintain the cylindrical shape of the proximal and distal 15, 17 sections. The thread or suture 30 (constraining means) at the interface 46 interconnecting the first and second intermediate subsections 40,41 may or may not function to tension the apices 45 of those respective subsections. The illustrative embodiment of FIG. 7 can be similar to that of FIG. 6 except that the intermediate section 16 also comprises a third intermediate subsection 43, located between intermediate subsection 40 and 41, that extends the length of the artificial sinus. The illustrative third intermediate section 43 comprises a short cylindrical or band-shaped portion whose width can be adjusted to create the desired geometry of the artificial sinus 34. Additional subsections can be added as well, if so desired.

Figure 8:
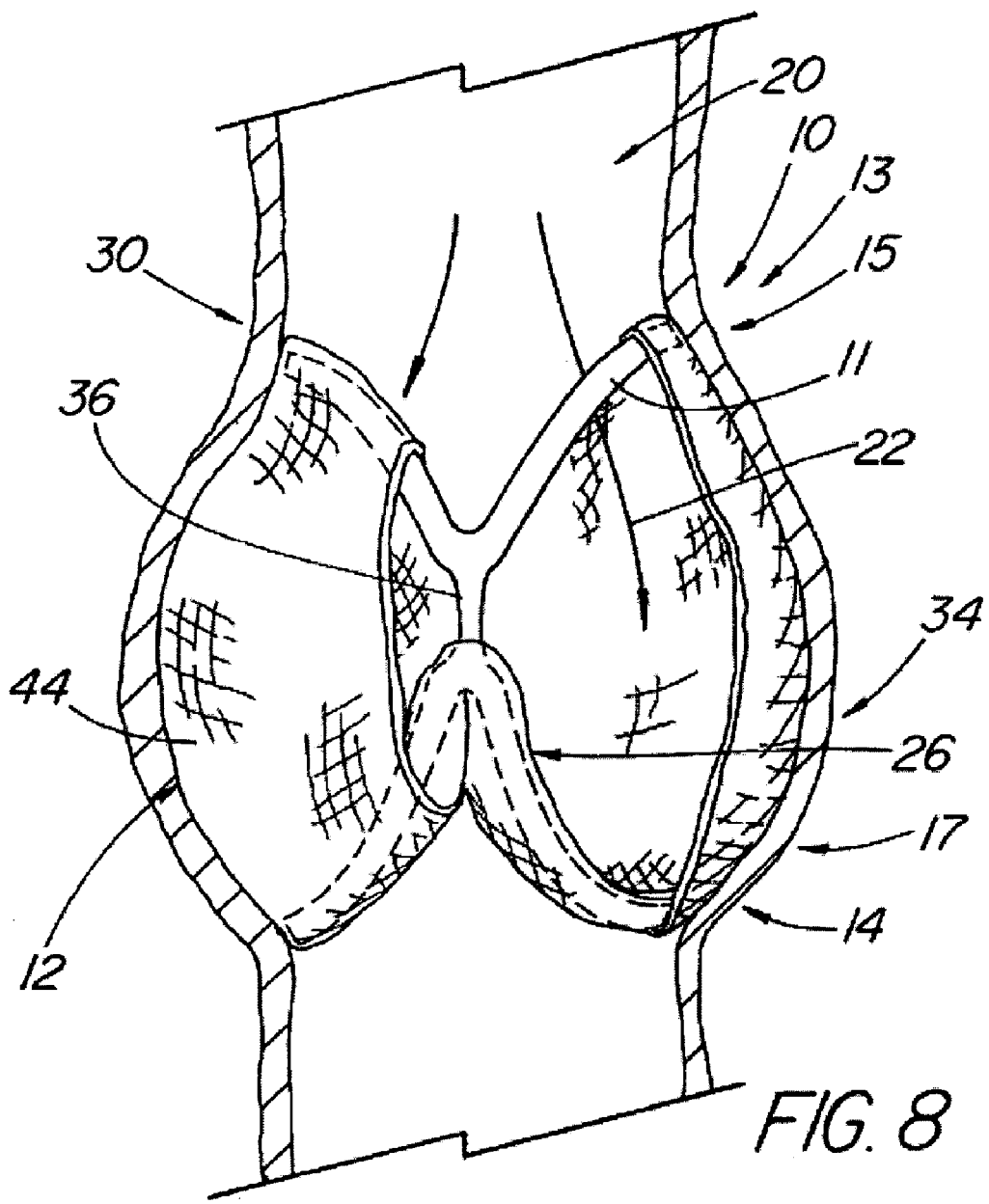
FIG. 8 depicts a partially sectioned side view of an embodiment of the present invention that includes an external sleeve of material.

The proximal and distal sections are preferably configured to include a substantially open area between them with the valve structure being attached to the distal section such that it can be positioned just below the artificial sinus. Optionally, a sleeve of a biomaterial (e.g. a bioremodelable material such as small intestinal submucosa (SIS) or another collagenous extracellular matrix) or fabric can be attached over the proximal and distal sections such that it forms a seal between the medical device and the vessel wall, including the artificial sinus. FIG. 8 depicts an embodiment in which the support structure 11 comprises a proximal portion 15 joined to a distal portion 17 by a interconnecting strut 36, the entire support structure being cut from a single piece of cannula, such as stainless steel or nitinol. The valve structure 12, comprising a plurality of leaflets 26, can be attached to the distal portion 17 such that the artificial sinus 34 can be formed in the largely open, unsupported region between the proximal and distal sections 15, 17 by the vessel 20 bulging outward, similar to the embodiment depicted in FIG. 2. The valve 10 further includes an optional covering 44, such as an outer sleeve of SIS (or other suitable biological or synthetic material), that can be attached to both the proximal and distal sections 15,17 of the support structure 11, which helps seal the medical device to prevent leakage of retrograde fluid therearound. The covering 44 is preferably of a constitution and configuration such that it does not interfere with the creation of the artificial sinus 34.

In still yet another aspect, the support structure of the medical device can be configured such that the attachment pathway has a first, proximal portion in which the one or more longitudinal attachment struts extending from the proximal bends or commissures that carry and support the proximal outer edges of the leaflets (and span the orifice) have a strongly longitudinal orientation with respect to the longitudinal axis of the medical device and valve structure, and a distal portion of the attachment pathway that extends circumferentially (laterally) and distally from the longitudinal axis to form the bottom or distal edge of the outer leaflet edge or perimeter. FIGS. 9, 11, and 13-20 illustrate embodiments of an artificial valve 10 in which support structure 11 carrying the leaflets 26 can be configured to increase the leaflet contact (coaptable) area 57 about the proximal portion of the valve structure 12 without relying on built-in slack within the material to bring the leaflets in closer proximity and provide for a extensive sealing area, longitudinally. As defined in this application, the leaflet contact area 57 comprises a longitudinal portion along the valve structure 12 in which the facing surfaces of opposing leaflets 26 (two or more) coapt or lie in close proximity to one other while in a dry or resting, neutral state (i.e., the pressure differentials across the valve orifice are essentially equalized such that the leaflets are not being forced together or apart due to external forces, such as fluid flow), when the medical device can be an expanded or deployed configuration.

Referring again the FIGS. 13-20, the support frame 11 may be configured for maximizing the extent of the leaflet contact area 57 by including one or more longitudinal attachment struts 49, 50 that define at least the proximal portion 75 of the attachment pathway 74 of each leaflet lateral outer edge 87, 88 (the terms outer edge 39 and lateral outer edges 87, 88 being defined herein as the area or zone along the leaflet that comprises the sealing interface). The longitudinal attachment struts 49, 50 and the proximal attachment pathways 75 have a substantially longitudinal orientation (e.g., substantially parallel) with respect to the longitudinal axis 64 of the medical device (and valve structure 12). At a point generally proximate the distal end 89 of the leaflet contact area 57 (the proximal portion 96 of the leaflet), the distal portions 76 of the adjacent attachment pathways 74 (which are joined proximally about a commissural point) diverge from one another (forming a generally Y-shaped pathway configuration) and assume a much more circumferential orientation than that of the proximal portion 75 of the pathway such that the outer leaflet lateral edges 87, 88 of each leaflet converge at a point lateral to the free inner edge 84 thereof to seal the passageway and form the distal portion 96 of the leaflet that defines the bottom 96 or "floor" of the pocket 55 or intravascular space adjacent the outer surfaces of each of the leaflets, which generally assumes a strongly cupped or curved shape such that the leaflet assumes a generally "folded" appearance due to the acutely angled attachment pathway 74 with the proximal portion of the leaflet having a strong longitudinal orientation with respect to the medical device and vessel and the bottom portion 96 having a strongly perpendicular orientation relative to the longitudinal axis of the vessel and medical device. It should be noted that the commissures 27, 28, while located about the proximal end 13 of the illustrative medical device 10, may be located proximal thereto such that additional support structure 10 extends proximally, such as in the embodiments of FIGS. 2-8, 12.

Figure 10:
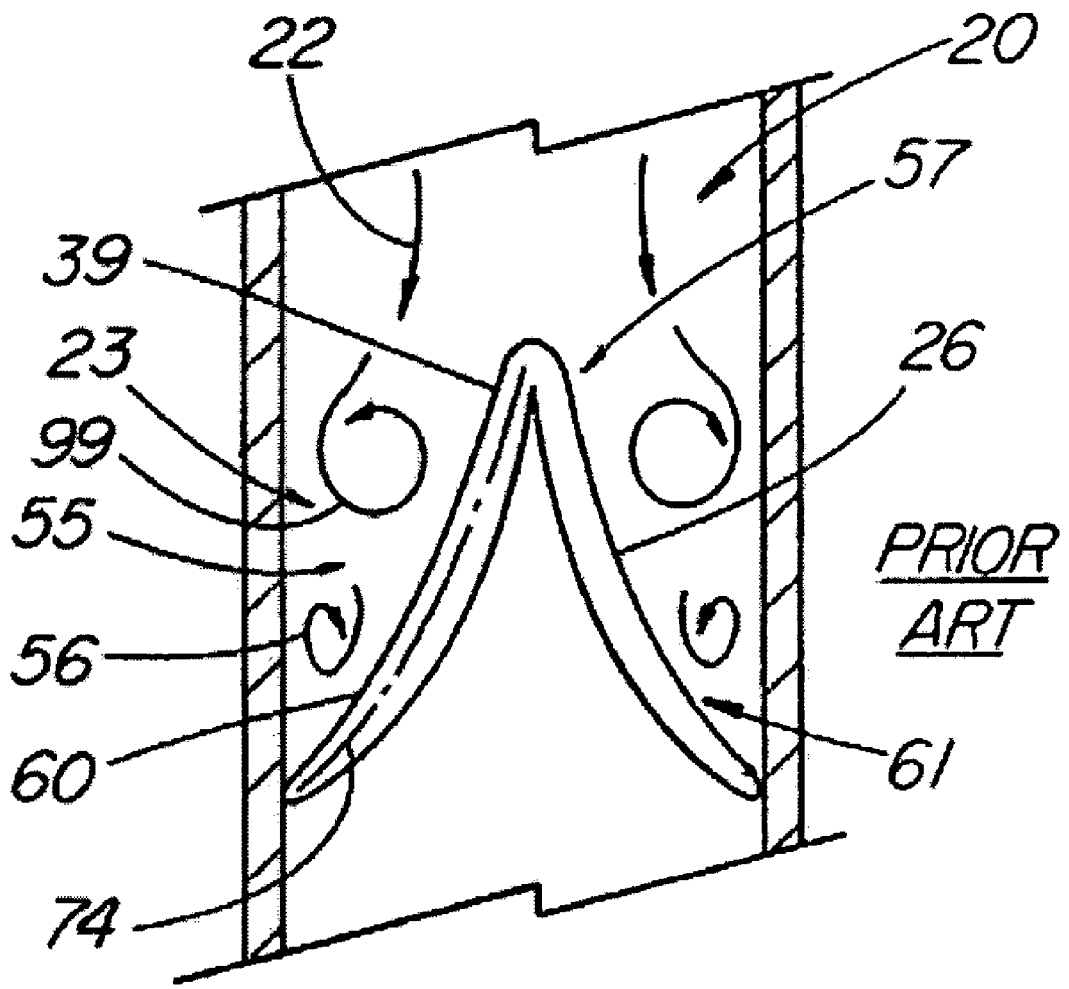
FIGS. 10-11 depict side views comparing the flow patterns in a standard valve leaflet configuration with those of the embodiment of FIG. 9.

By extending or maximizing the leaflet contact area and decreasing the radius of the curvature of the leaflet (increasing curvature) about the distal portion thereof, the basal or distal portion of the pocket 35 adjacent each leaflet can be enlarged to facilitate and maximize the size and/or velocity of the flow vortices 55, 56 formed therein during retrograde flow. During pre-clinical investigations, these broader pockets have been shown to be especially advantageous in bi-leaflet artificial valve designs implanted in the venous system, these valves exhibiting a marked reduction in thrombus formation as compared to earlier designs. The improvement in flow dynamics for the purpose of clearing the pocket 35 of stagnant blood that can thrombose and compromise valve function or lead to other complications can be depicted in a comparison of FIGS. 10 and 11. Laboratory analysis of the patterns of retrograde flow within a valve has shown that multiple vortices are typically created. In the embodiment of FIG. 10, which has a generally (inverted) V-shaped attachment pathway 74, a first vortex 55 can be created below which a second, smaller vortex 56 can be usually present, usually having opposite flow, which may be at least partially inadequate for clearing away blood pooling about the base of the leaflets 60,61 in a venous valve. The lateral distance between the bases of the leaflets 60, 61 is preferably less than the maximum diameter of a sinus region, and may be equal to or larger than the diameter of the body vessel proximate the sinus region. In the embodiment depicted in FIG. 11, which has a generally (inverted) Y-shaped attachment pathway 74, the larger pocket (at least at the basal portion) allows for a larger and stronger second vortex 56 of fluid created by retrograde flow that can improve the clearing away of any pooling blood that would otherwise collect there and potentially provide for greater downforce on the leaflets 60, 61 to improve closure of the valve.

Figure 9:
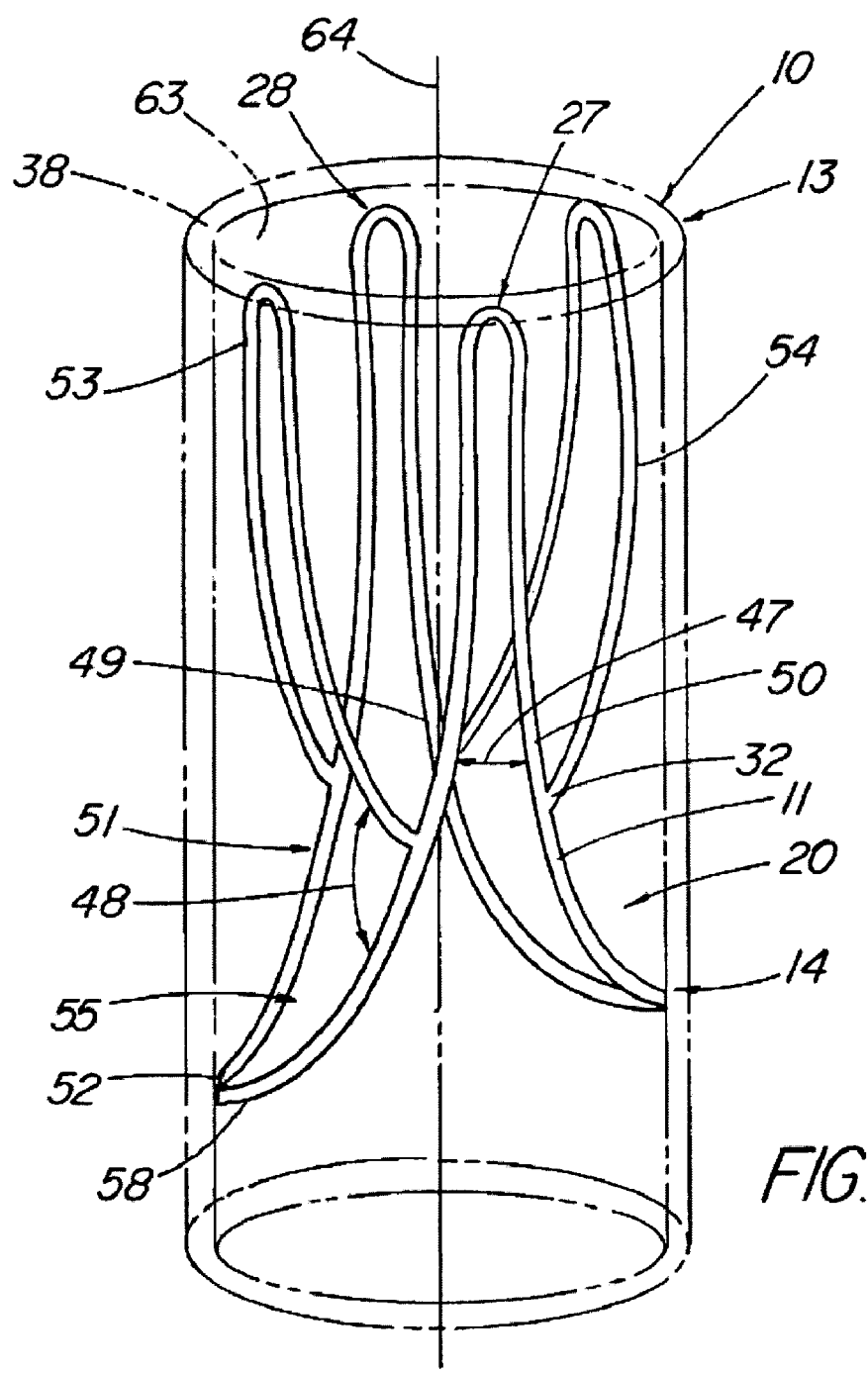
FIG. 9 depicts a perspective view of a support structure of the present invention adapted to increase coaptation of leaflets and pocket size within the vessel.
Figure 11:
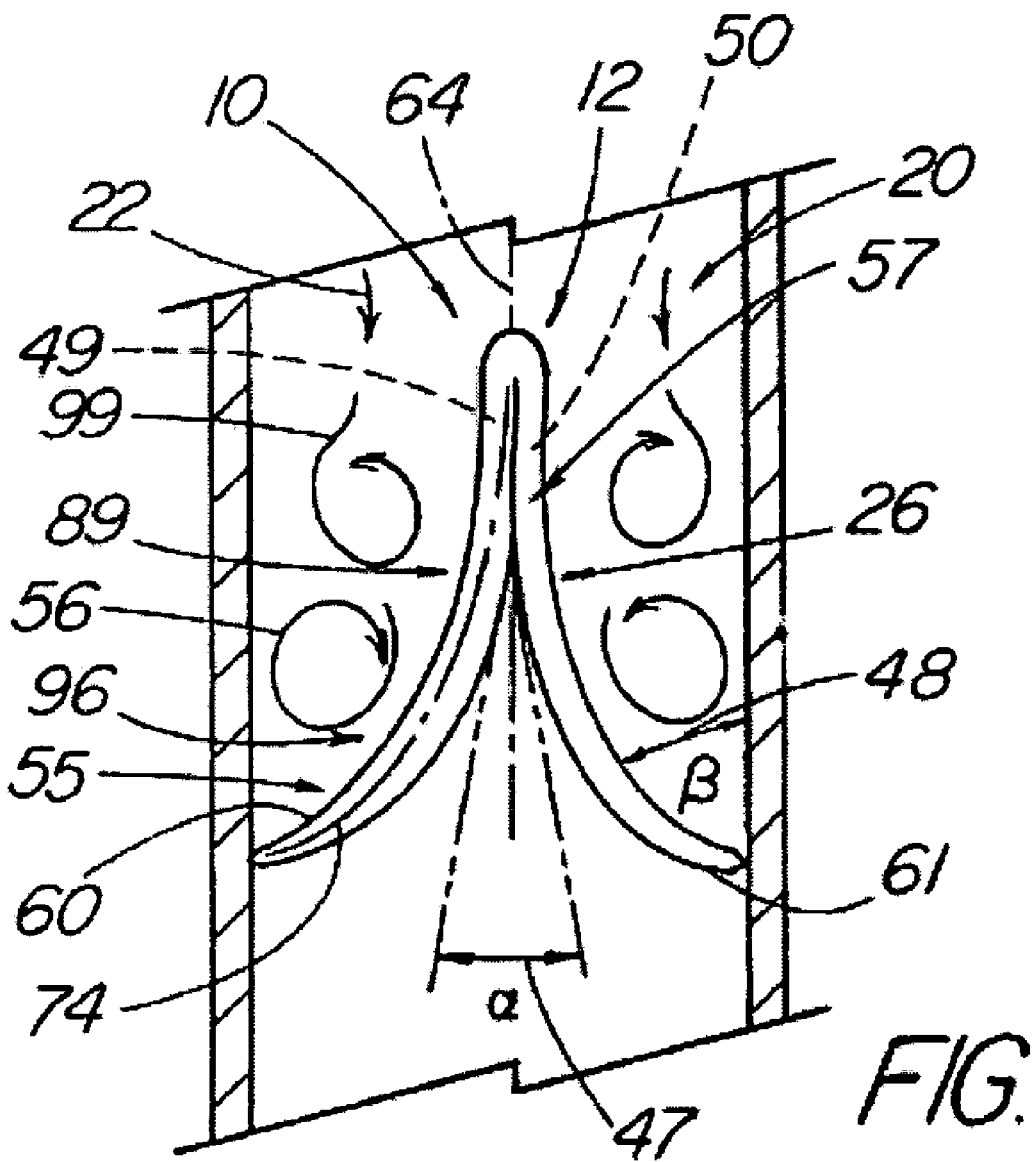

When viewed from the side in FIG. 11, the support frame and attached leaflet can be configured such that the angle (angle α) formed between the opposing leaflets, as carried along the proximal attachment pathway, can be substantially less than the angle (angle β) formed between distal attachment pathways and the vessel walls. This configuration can result in leaflets having large coaptable area relative to the overall surface area, which improves sealing (including reducing the effects of retraction by the valve material) and allows for larger pockets surrounding the leaflets which, like the sinus, facilitate the creation of larger, stronger vortices of retrograde flow that help close the leaflets and clear away blood or fluid that could otherwise stagnate under conditions where the surrounding pockets are smaller in size. As used herein, the term "retrograde flow" can be defined as bodily fluid traveling in a distal direction (away from the heart), whether due to gravitational forces, redirection due to contact with the medical device or bodily lumen walls, or by some other means. FIGS. 9 and 11 depict an artificial venous valve 10 in which the frame 32 of the support structure 11 can be configured such that the pair of longitudinal attachment struts 49,50 extending from each of the commissures 27, 28 that represent the proximal attachment points for the valve structure (not shown) form a first angle 47 (α) with respect to one another that can be less than the second angle 48 (β) that can be formed between the distal attachment struts 51,52, which comprise continuations of the longitudinal attachment struts 49,50 (together comprising the legs 58 of the frame 32), and the inside 63 of the vessel wall 38. The first angle 47 is preferably between about −10 and 45 degrees (a negative angle being possible with a sufficiently large-radius bend about the commissure) with a more preferred angle being about 0-25 degrees and a most preferred angle of about 0-10 degrees. The longitudinal attachment struts 49, 50 can diverge or converge at various points therealong (i.e., bow inward or outward), so the first angle may be measured for only the proximal portion 75 or can be measured between vectors representing the best straight line longitudinally traversing each strut 49, 50. The illustrative embodiment also includes a pair of optional stabilizing arms 53, 54 that extend laterally from the legs 58, 59 to help center the medical device 10 within the vessel 20. Ideally, the angles depicted in the frame 32 configuration of FIG. 11 results in the opposing leaflets 60, 61 being much more in alignment (e.g., parallel) with one another than in a medical device where the angles 47, 48 are relatively the same, such as the prior art valve shown in FIG.

10, particularly over the proximal half of the leaflets 60, 61. The creation of a larger pocket around the base of the leaflets 60, 61 can help create larger and/or stronger vortices of retrograde blood flow. A second clinical benefit can be related to the creation of a larger area of coaptation between the leaflets 60, 61, which can provide a better seal against possible reflux through the valve orifice.

FIGS. 13-18 depict another group of embodiments configured for maximizing the coaptation distance or region between the leaflets in which the attachment pathway 74 comprises a proximal portion 75 that generally extends along one or more longitudinal attachment struts 49, 50 that are generally aligned with the longitudinal axis 64 of the medical device and a distal portion 76 that can be angled laterally from the longitudinal attachment struts and generally follows the distal attachment struts 51, 52 which unlike the embodiment shown in FIG. 9, extend laterally outward from the longitudinal struts 49, 50 as separate struts. As with the embodiment shown in FIG. 9, the distal attachment struts/portions converge at a point oppositely facing each leaflet 60, 61 where they attach to the lateral support structure 53, 54, which helps center the medical device in the vessel and protects the leaflets from adhering to the vessel wall. In the embodiments of FIGS. 13-17, the support frame 11 further includes proximal support arms 77, 78 that attach to and extend from the longitudinal attachment struts 49, 50 about the commissure points 27, 28 and provide an interconnection with the lateral support structure 53, 54 (also shown in FIG. 15).

One embodiment includes a frame comprising a pair of longitudinal attachment struts originating from each commissure bend. The struts extend in generally longitudinal direction, and may diverge toward the distal end of the medical device before more acutely diverging as they curve laterally and circumferentially away from the proximal strut portions. The transition between the proximal and distal portions of attachment pathway preferably comprises a bend having a radius that can be distinctly smaller than that of the adjacent strut portions (the proximal portions being straight some embodiments). The distal attachment pathways may converge to define the bottom outer edge of each leaflet. Preferably, the support frame of the medical device includes a pair of substantially parallel longitudinal attachment struts to which the leaflets are attached to form the proximal portion of the attachment pathway, and distal attachment struts extend circumferentially and laterally outward from the substantially parallel struts to form the distal portion of the attachment pathway. The support frame carrying the valve structure may comprise radial sections (e.g., quadrants in a bicuspid valve) that are of an identical pattern but with alternating orientation such as to provide for radial stability and better expandability characteristics. The radial section not carrying the leaflet proximal outer edges desirably serves as a lateral support structure for adding longitudinal stability and protecting the leaflets from adhering to the vessel walls. The parallel struts provide for advantageous bending and torsional characteristics such that the frame has utility as a stent. In an alternate embodiment of the support structure, the lateral outer edges of the opposing leaflets can be attached to single longitudinal attachment strut having a pair of distal struts extending laterally outward and circumferentially to carry the bottom half of the leaflet and define the overall shape thereof. The strut may be thicker than adjacent struts and include aperture thereaolong for facilitating attachment of the valve structure.

Figure 13:
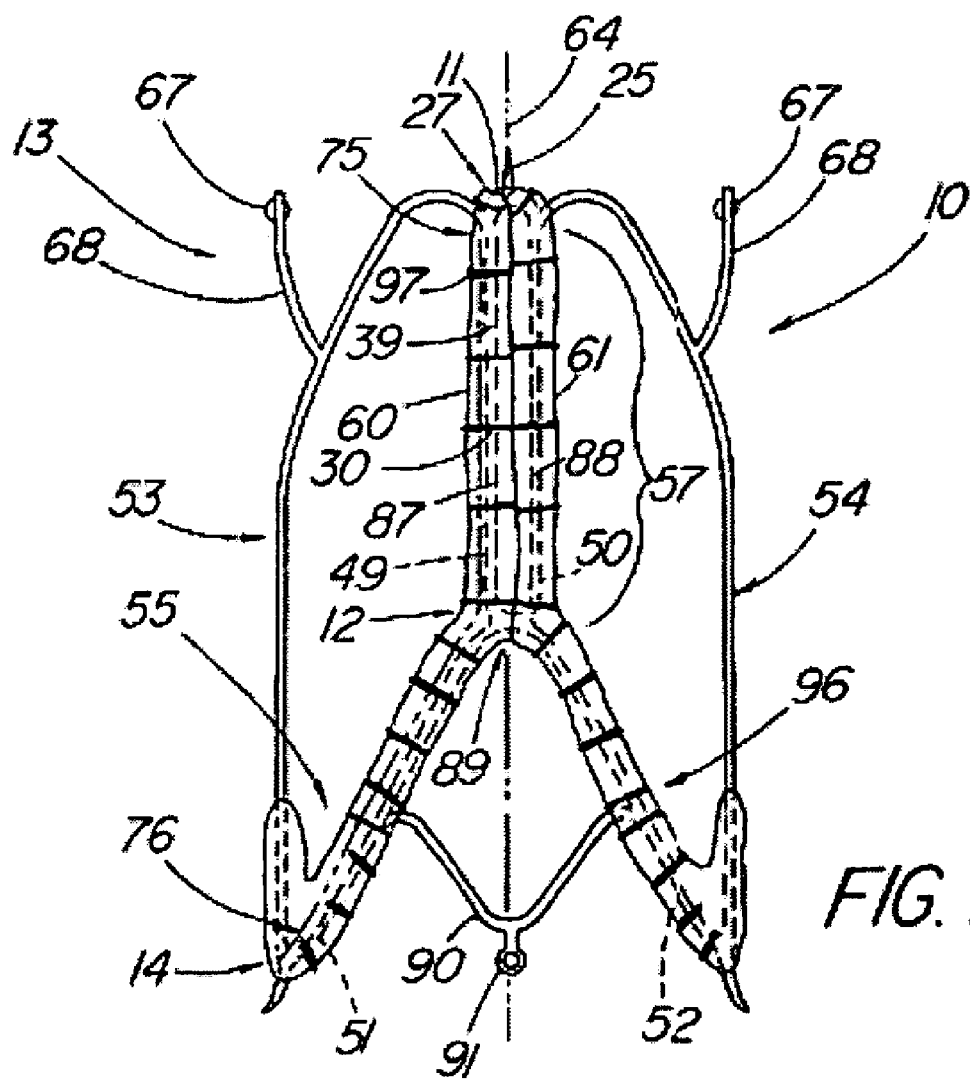
FIG. 13 depicts a side view of an embodiment of the present invention in which the leaflets are attached to the parallel struts to increase the area of coaptation.
Figure 14:
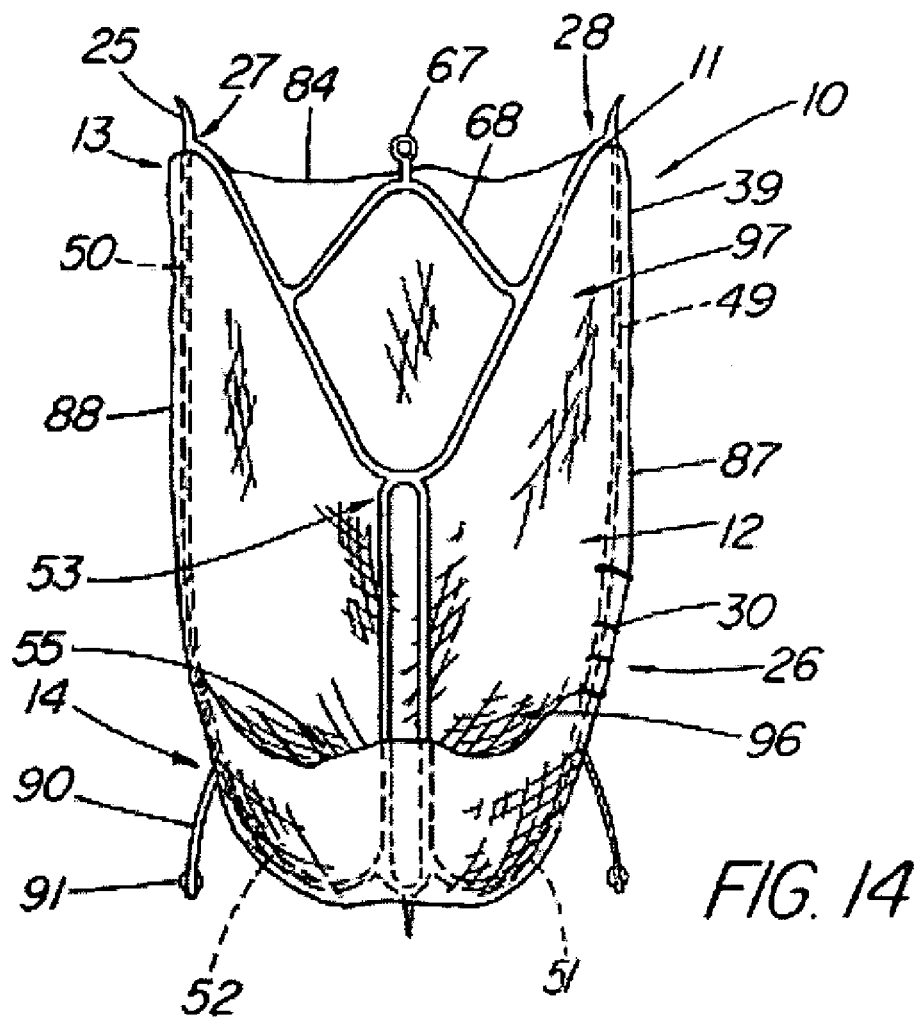
FIG. 14 depicts a side view of the embodiment of FIG. 13 that is rotated 90 degrees therefrom.
Figure 15:
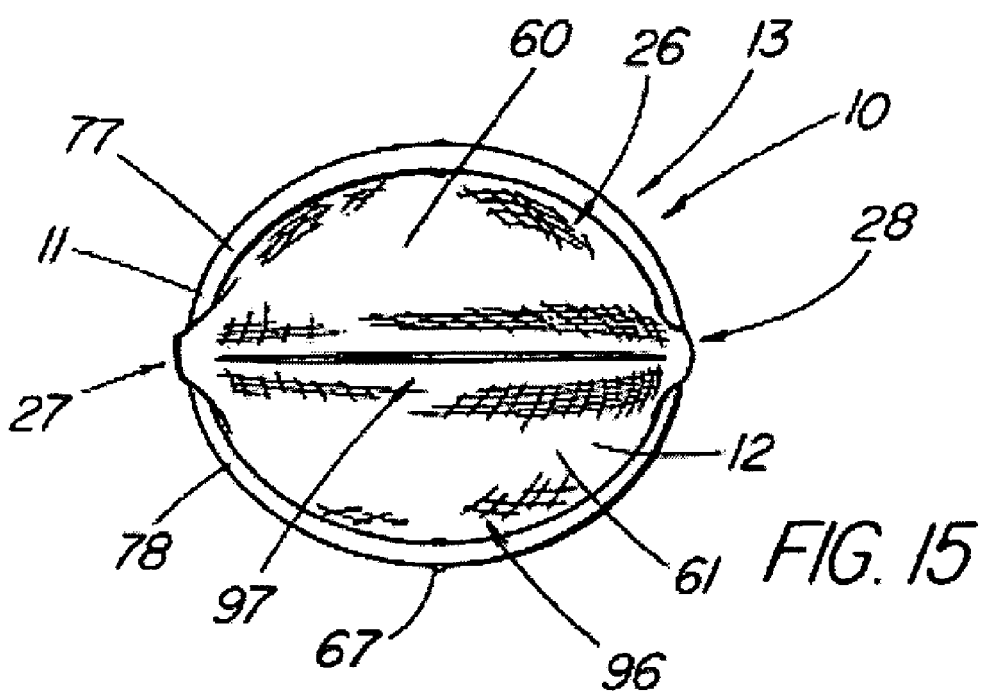
FIG. 15 depicts a top view of the embodiment of FIG. 13.
Figure 16:
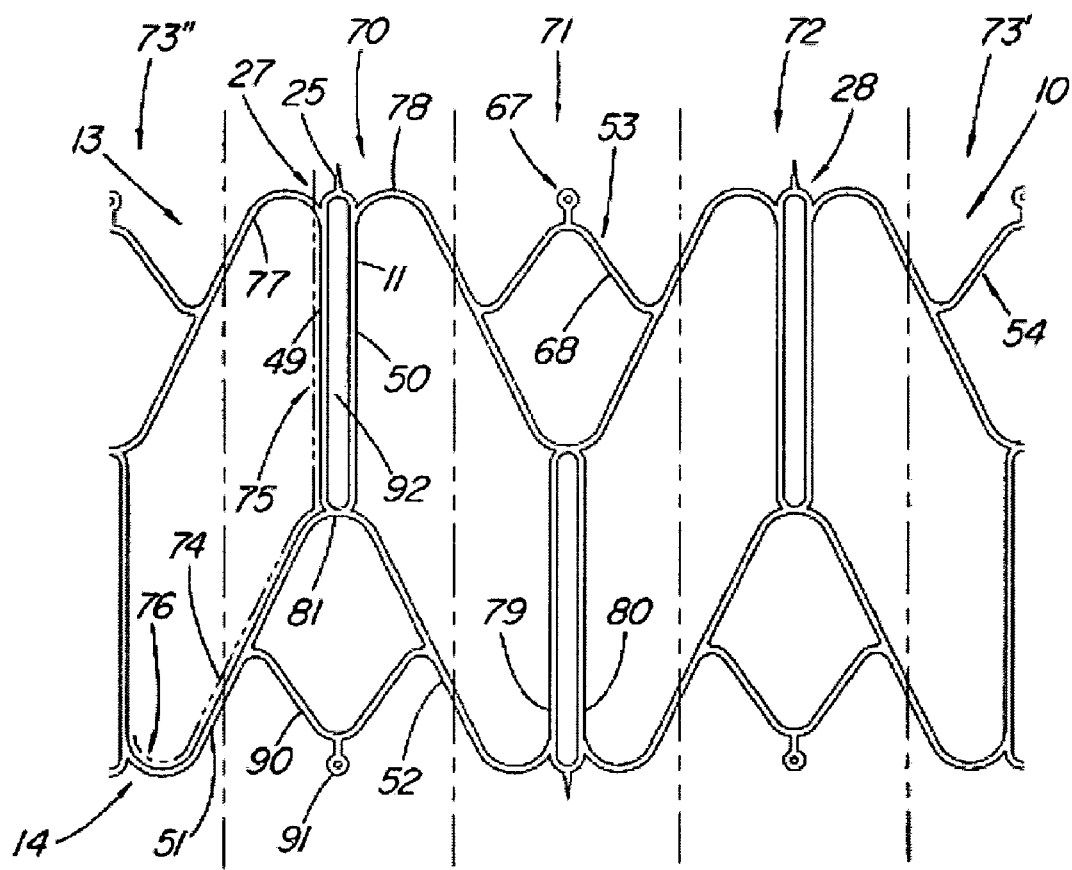
FIG. 16 depicts an unrolled view of the support frame of the embodiment FIG. 13.

The embodiment depicted in FIGS. 13-14 comprises a pair of longitudinal attachment struts 49, 50, generally parallel to one another, which are adapted for attaching the respective leaflets 26 therealong, thus creating a large leaflet contact or coaptable area 57 that preferably extends over half of the length of the medical device. As depicted in FIG. 16, the support structure 11 generally forms a serpentine configuration adapted to be readily collapsible and expandable. The support structure 11 or frame shown in FIG. 16 can be divided into four sections or quadrants 70, 71, 72, 73 that are identical except for their orientation, sections 70 and 72 being oriented with the commissures 27, 28 and longitudinal attachment struts 49, 50 carrying the valve structure 12 being oriented proximally toward the first end 13 of the medical device 10. The repeating, uniform design of the support structure 11 of the illustrative embodiment advantageously provides better structural stability, compressibility/expandability, and overall integrity than a support structure that does that comprise a non-uniform, non-repeating frame pattern.

The lateral arms 77, 78 of the lateral support structure 53, 54, that connect to the longitudinal attachment struts 49, 50 can each include a strut 68 that carries a proximal radiopaque marker 67 used to facilitate orientation of the device 10 and provide additional support. An identical distal strut 90 and an optional radiopaque marker 91 can be located distal to the longitudinal attachment struts 49, 50 and attached to the distal attachment struts 51, 52 to serve a similar orientation and stabilization function. An integral barb 25 can be located about the commissural bends 27, 28 that interconnect the longitudinal attachment struts 49, 50. The parallel longitudinal attachment struts 49, 50 can be interconnected about the distal ends by a short interconnecting strut 81 such that an elongate closed cell 92 can be formed. The width of cell 92 may vary, although it is preferably sufficiently narrow to join the leaflets 60, 61 to the struts 49, 50, which could be especially advantageous if the leaflet material retracts during the remodeling process. A preferred width between the two struts 49, 50 would be between 0-5 mm, with 0-3 mm being more preferred and 0-1 mm being most preferred. The spacing between the opposing leaflets should not permit an unacceptable amount of reflux through the valve.

Figure 17:
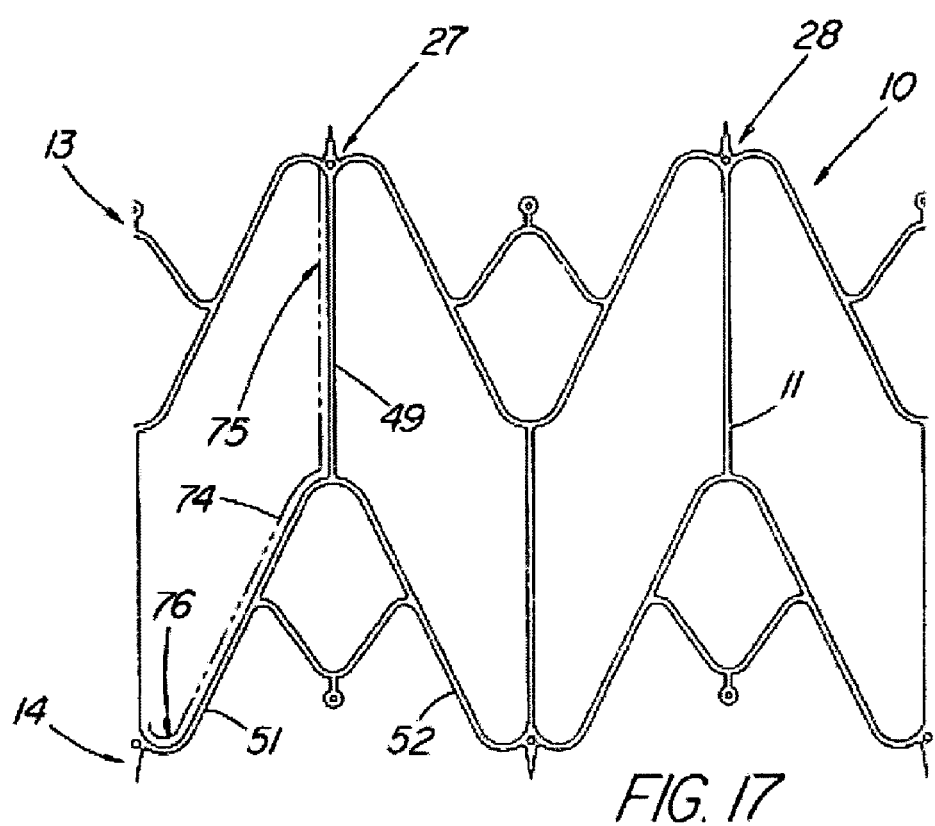
FIGS. 17-18 depict unrolled views of additional embodiments of the present invention for increasing the area of leaflet coaptation.
Figure 19:
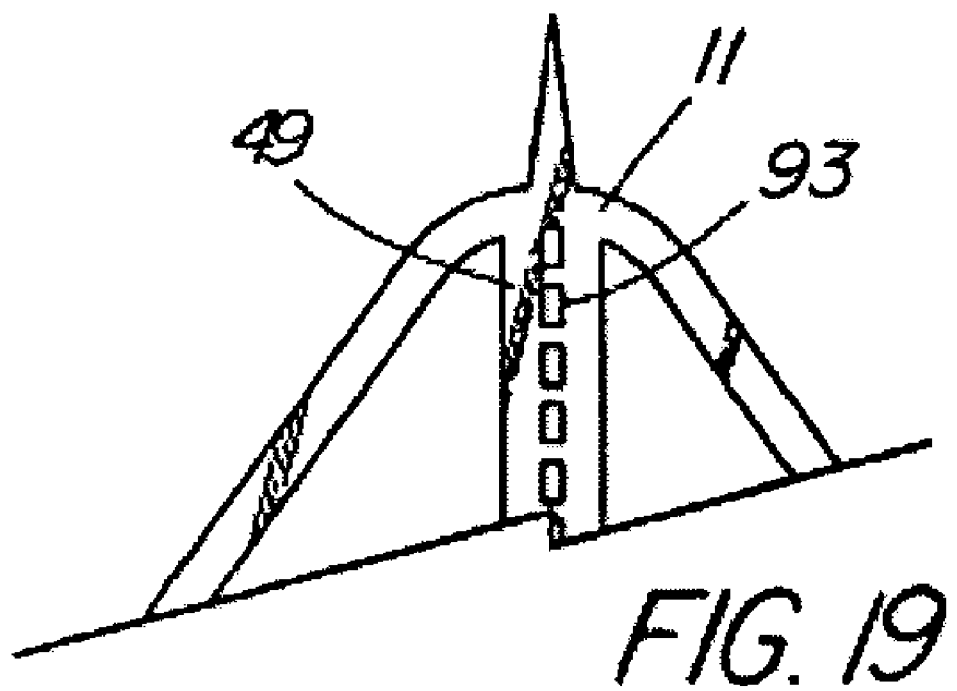
FIGS. 19-20 depict plan views of adaptations in the support structure for affixing the valve structure thereto.
Figure 20:
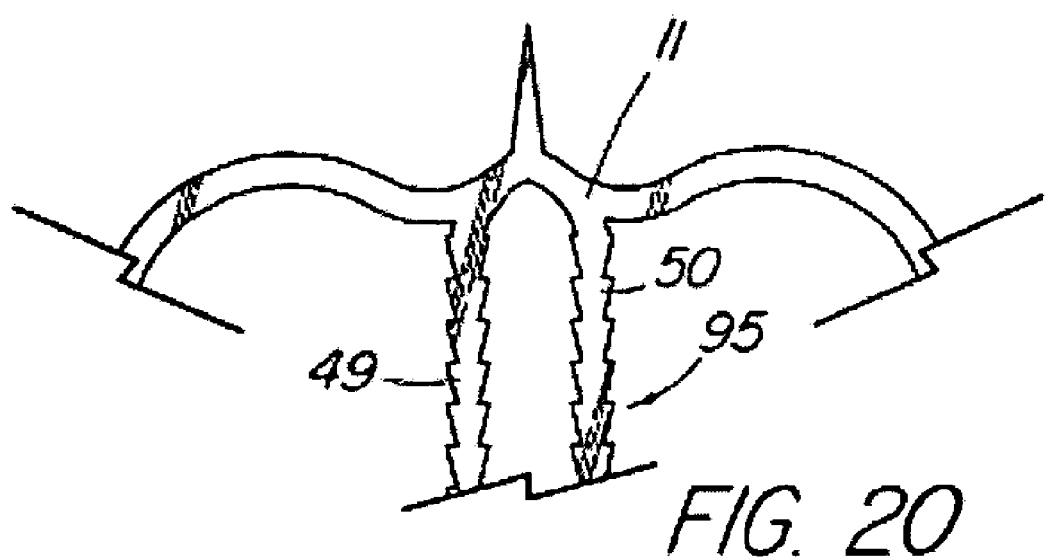
Figure 21:
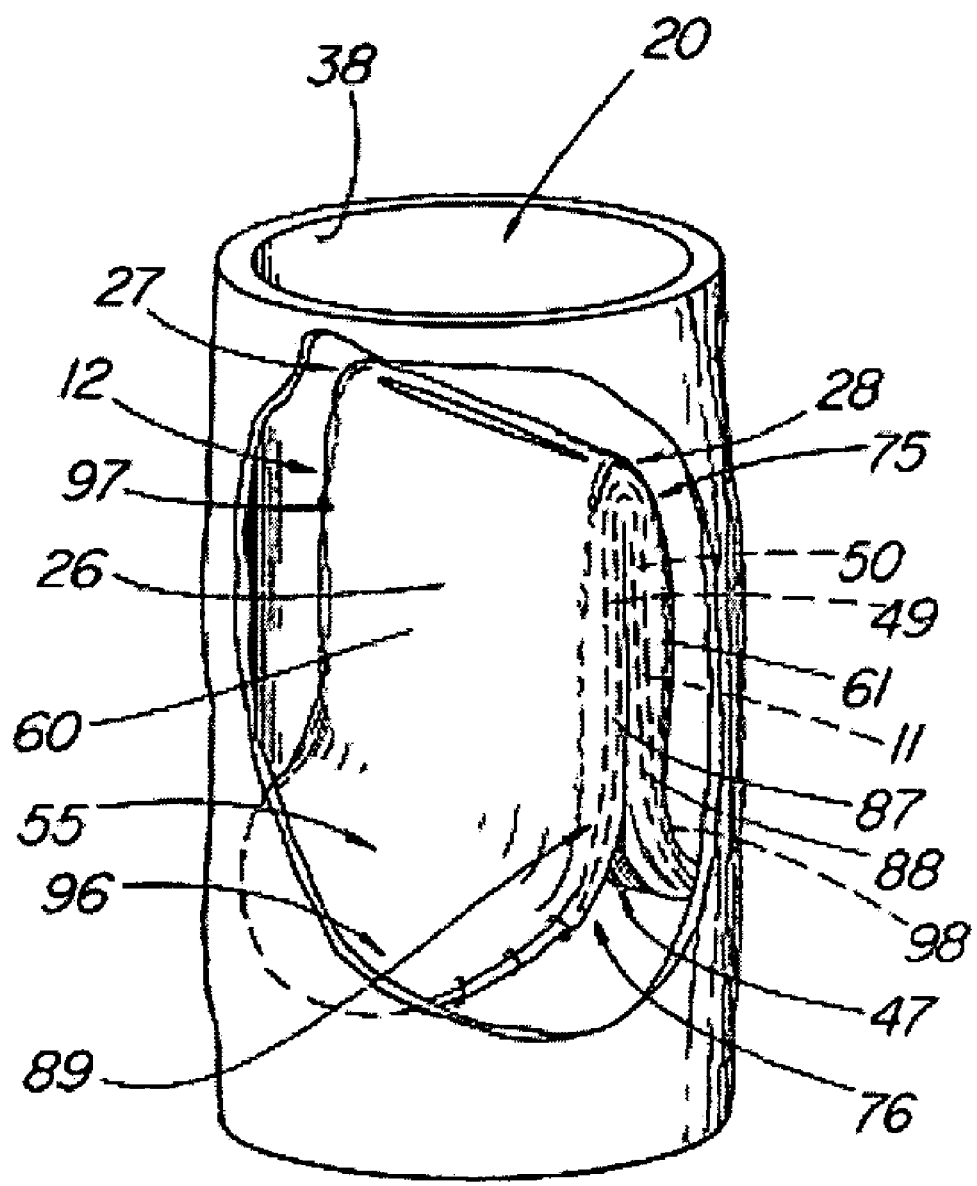
FIG. 21 depicts a partially sectioned perspective view of an embodiment in which the support structure does not co-extend along the entirety of the leaflet outer edges.

A similar frame design is shown in FIG. 17 which includes a single longitudinal attachment strut 49 to which both leaflets 60, 61 may be attached, allowing for extended coaptation between leaflets. The leaflets 60, 61 can be attached such that each abuts the strut 49 (e.g., sewn or attached with or without being wrapped over the strut) or the first lateral leaflet edge (not shown) can be wrapped around the strut 49 while the second leaflet lateral edge of the opposite leaflet can be sewn over the first lateral leaflet edge and strut 49. The single attachment strut can be of a width that can be generally uniform with respect to the other support structure or it may be made substantially thicker, such as shown in FIG. 19. Furthermore, a thicker strut 49 could include apertures 93 or slots of any shape or length distributed therealong for receiving sutures or other attachment elements 30, such as clips, rings, etc., for affixing or anchoring the leaf outer edges thereto. FIG. 20 depicts an embodiment having a pair of longitudinal attachment struts 49, 50 with anchoring structure 95, such as the illustrative scalloped edge that can be strategically configured therealong to help prevent or limit the attachment element 97 and the valve structure itself, from sliding down the longitudinal attachment struts 49, 50, especially during any retraction that may occur with a bioremodelable material. The anchoring structure can comprise any projections or other structure that provides a shoulder or irregularities along the edges of the struts that limits sliding of the leaflets along the longitudinal attachment struts 49, 50. Further examples of adaptations for limiting movement or migration of attachment elements (e.g., sutures) and covering material are disclosed in an application to Case et al. (U.S.

Ser. No. 10/820,918), entitled "Intraluminal Support Device with Graft" and filed Apr. 8, 2004, which is incorporated by reference herein.

Figure 18:
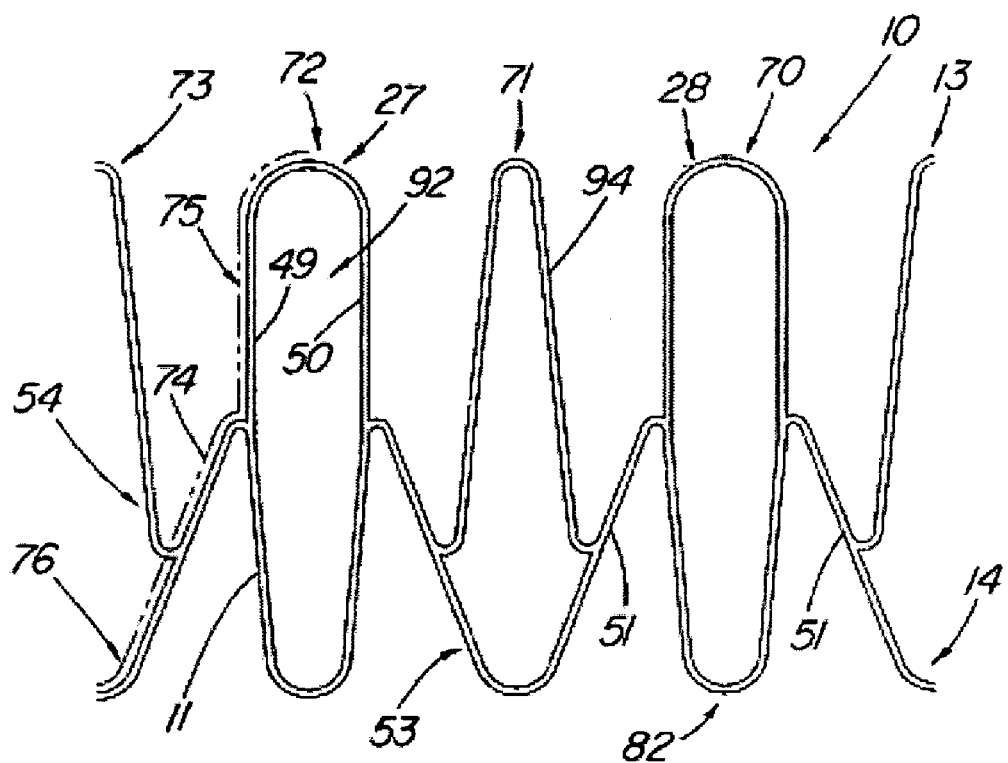

FIG. 18 depicts an embodiment having substantially parallel longitudinal attachment struts 49, 50 which can optionally slightly converge toward the distal end 14 of the medical device 10 (and are spaced more distant from each other than the embodiment of FIGS. 13-14. The commissural bends 27, 28 and distal bends 82 interconnect the longitudinal attachment struts and form a closed cell 92 as in the embodiment of FIGS. 13-16. The distal attachment struts 51, 52 provide the interconnection between the opposite closed cells 92 as well as the distal portion 76 of the attachment pathway 74. They also carry a lateral arm 93 and together comprise the lateral support structure 83, 84 that provide longitudinal support/stabilization and leaflet protection. The embodiment of FIG. 18 lacks proximal support arms 77, 78 of the embodiment of FIGS. 13-16.

Any suitable support structure 11, including those illustrated in FIGS. 9, 11, and 13-21, can be used to achieve the optimal leaflet angles in the valve structure 12 for creating larger pockets, as depicted. For example, the attachment pathway 74 of the valve structure 12 can comprise an attachment to an outside support frame to form the illustrative configuration with the frame 32 that does not extend along the outer edges 39 of the leaflets 60, 61, but is instead attached to one or more struts that cross the attachment pathway 74, especially along the distal portion 76 of the pathway. Furthermore, at least a portion of the outer edges 39 can be directly affixed to the vessel wall (such as being sutured, heat welded, or anchored with barbs, adhesives, etc.) with the frame 11 being absent or reinforcing or shaping only a limited portion of the leaflet outer edges 39, thus allowing for the vein to naturally collapse (at least partially) when not filled with blood. In the example depicted in FIG. 21, the frame 11 comprises a partial support 98 of a hair-pin configuration that includes a proximal bend about each commissure 27, 28 with free-ended longitudinal attachment struts 49, 50 extending therefrom which help form the leaflet angle 47, while the distal portion 76 of the attachment pathway 74 comprises an alternative attachment that does not result in the leaflet material being urged thereagainst by a radially expandable frame. Methods include surgical attachment, tissue welding, adhesives, barbs and other well-known methods, teachings of which can be included in a co-pending U.S. patent application entitled, "Percutaneously Deployed Vascular Valves with Wall-Adherent Adaptations," (Case et al.) filed Feb. 11, 2005 Ser. No. 11/056,903, the disclosure of which can be expressly incorporated by reference herein. The angle of the leaflets 60, 61 relative to the longitudinal axis 64 of the medical device and vessel (half of the first angle 47 or α/2) is preferably about −5-22.5 degrees with a more preferred angle of 0-10 degrees and a most preferred angle of 0-5 degrees. The relatively small or shallow angles of the longitudinal attachment struts 49, 50 about the commissures 27, 28 allows for a larger space adjacent the leaflets 60, 61 and broader pockets 35 at the base of the leaflets. The longitudinal attachment struts 49, 50 of the support structure can be formed generally parallel to one another along the proximal portions of the longitudinal attachment struts 49, 50 to create the maximum pocket size and greater coaptation of the leaflets. For example, the pocket 35 areas would be maximized in an attachment pathway 74 where angle 47 can be zero (or a negative angle) and angle 48 can be at least 90 degrees, such that the attachment pathway along each leaflet lateral outer edge 87, 88 can be generally L-shaped such that the distal portion 76 of the attachment pathway angles abruptly from the proximal portion rather than assuming a dog-leg configuration as shown in the illustrative embodiments.

The amount of contactable or coaptable area 57 can be expressed in different ways. Preferably, the length of the leaflet contact area 57 (or proximal portion 75 of the attachment pathway) in a typical venous valve is preferably at least 2 mm and as much as 50 mm (depending on the configuration of the valve), with a more preferred length of 5-30 mm and a most preferred range of 5-15 mm. In an average sized venous valve having a length of 25 mm, the preferred range of the leaflet contact area 57 or proximal attachment pathway 75 would be 10-100% of the medical device length (2.5-25 mm), assuming the valve structure 12 can be generally as long as the support frame 11. A more preferred leaflet contact area 57 would comprise 30-60% with 35-55% being most preferred in a medical device of the same general type as depicted. The relationship between leaf contact area and the diameter of the vessel may be a factor in optimizing the functionality of the valve 10. Preferably, the length of the longitudinal attachment struts 49, 50 and/or leaflet contact area 57 is about 25 to 250% of the nominal vessel diameter with a more preferred range of 25-150%.

The amount of slack in the leaflet material also helps determine how well the leaflets coapt during retrograde flow and how large of an opening they permit during antegrade flow. Preferably, but not essentially, the medical device is configured such that the distance formed between the leaflets in their fully open position and the vessel diameter remains preferably between 0-100% of the vessel diameter, with a more preferred range of 20-80% of the vessel diameter and a most preferred range of 50-70%. By substantially orienting the longitudinal attachment struts 49, 50 with the longitudinal axis 64 of the medical device, less slack can be necessary for optimal or extended coaptation. Not having the leaflets regularly contact the outer walls of the vessel can be especially important when using a bioremodelable material, such as an ECM, which can partially or completely adhere to the wall over time as tissue grows into the leaflets, thus compromising the functionality of the valve.

The proximal section of the valve may be wider in diameter at its proximal end, which anchors the medical device in the vessel, and narrower at the interface between the proximal and intermediate sections. This, in combination with a leaflet structure that maximizes pocket size, results in retrograde flow being subject to a Venturi effect which increases flow and the strength of the vortices to close the valve and clear the pockets of potentially stagnating fluids.

Figure 12:
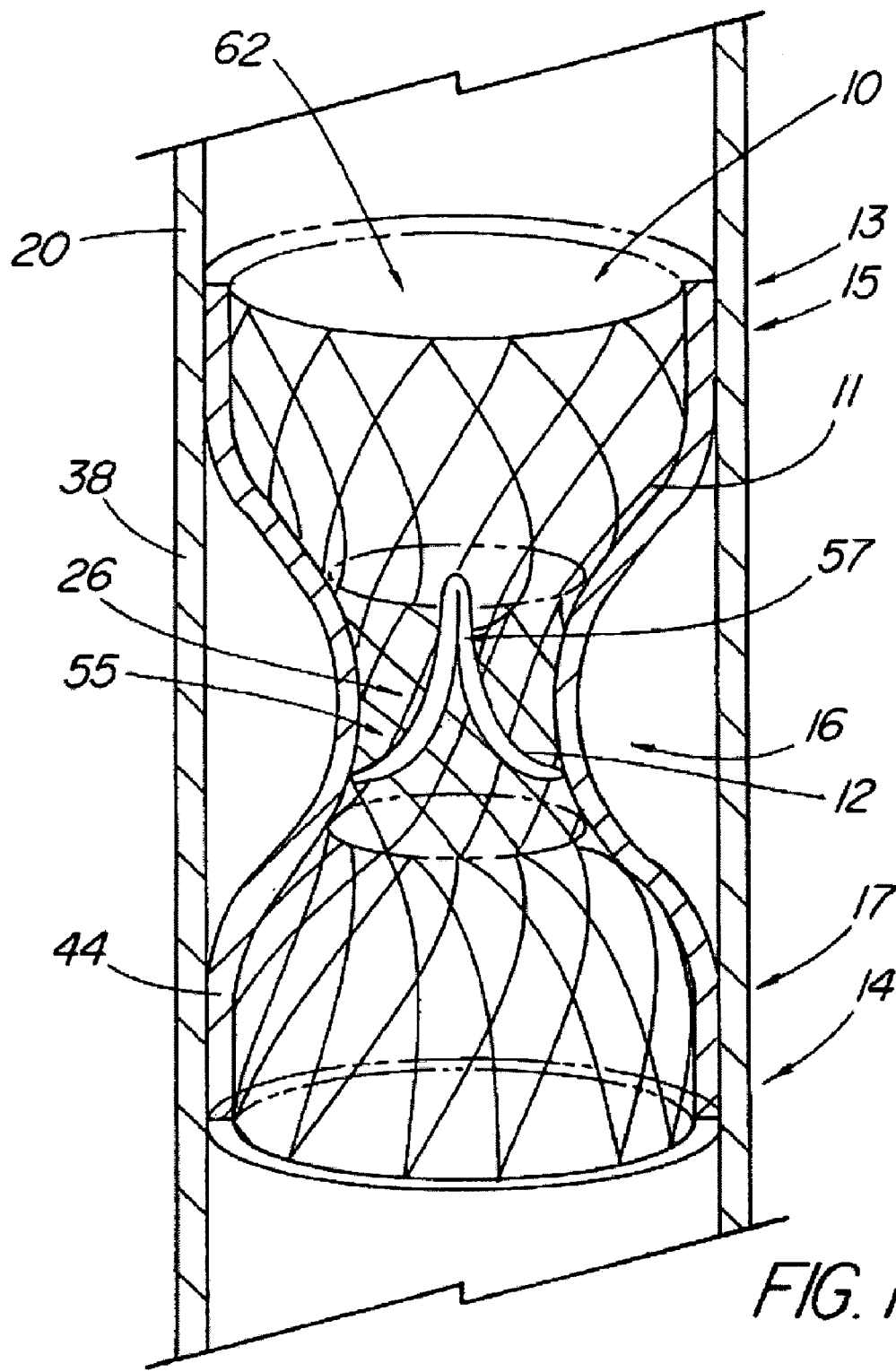
FIG. 12 depicts an embodiment of the present invention having a combination of a narrowed intermediate section and the valve structure configuration of FIG. 9.

FIG. 12 depicts an embodiment having different structural configuration to alter retrograde fluid flow patterns within the pocket to prevent pooling of blood or bodily fluid. The support structure 11 includes proximal and distal sections 15, 17 which are sized and configured to expand and engage the walls 38 when the valve 10 is deployed within the bodily passage 20. The intermediate section 16, which includes the valve structure 12, can be narrower than each of the adjoining proximal and distal sections 15, 17. A covering of biologically-derived or synthetic biocompatible or bioremodelable material 44, such as a collagenous extracellular matrix (ECM) (e.g., SIS), pericardial tissue, or fabric, such as DACRON, ePTFE, etc., can be attached over or inside the support structure to enclose passageway 62 and to help seal the medical device with the vessel. The proximal and distal sections 15, 17 are generally frustoconical or bowl-shaped with the interface 46 with the proximal or distal end of the intermediate section 16 being smaller in diameter than the proximal or distal ends 13, 14 of the medical device. By narrowing the passageway 62 of the medical device 10 at the point where it transitions between the proximal section 15 and the intermediate section 17, a Venturi effect can be created in which the retrograde flow can accelerate, which advantageously produces enhanced flushing action (e.g., stronger vortices) within the pockets 35 surrounding the leaflets 60, 61. The ability of the valve 10 to prevent pooling of blood or fluid around the pockets 35 can be further enhanced in the illustrative embodiment by configuring the leaflets 61, 62 as in the example shown in FIG. 11. The configuration of the proximal and distal sections may be the same or different configurations. The respective sections 15, 16, 17 may be separate, attached units, as shown, or represent subsections of a single anchoring portion 24, similar to the embodiment of FIG. 4.

It should be noted that the support structure and valve structure shown in each of the figures in the application are merely exemplary of the numerous well-known possibilities, many others of which are disclosed in U.S. patent application Ser. No. 10/642,372 entitled, "Implantable Vascular Device," filed Aug. 15, 2003 and whose disclosure can be expressly incorporated by reference herein. For example, the valve structure may comprise more than the illustrative two leaflets or comprise leaflets of other shapes and configuration.

The valve structure may also comprise a non-leaflet valve such as one or more tubular sleeves or other configurations adapted to restrict fluid flow. With regard to the support structure, it may be formed from wire, cut from a section of cannula, molded or fabricated from a polymer, biomaterial, or composite material, or a combination thereof. Any suitable pattern (i.e., configuration of struts and cells) of the anchoring portion(s) can be selected to provide radial expandability to the medical device.

Preferably, the implantable medical device can define a sinus region within a body vessel upon implantation. A sinus region is preferably characterized by one or more dimensional relationships between the diameter of the body vessel proximal to the sinus region, the maximum diameter of the sinus region, the length of the sinus region and/or the length of a valve leaflet within the sinus region. These preferred geometric relationships for a sinus region can be described with reference to an exemplary valve 110 comprising a sinus region 137 having a preferred geometry illustrated in FIG. 22, which is not drawn to scale. Implantable prosthetic valves can provide a sinus region having one or more geometric relationships illustrated by the exemplary valve 110, such as the sinus region 137 having a preferred geometry.

Figure 22:
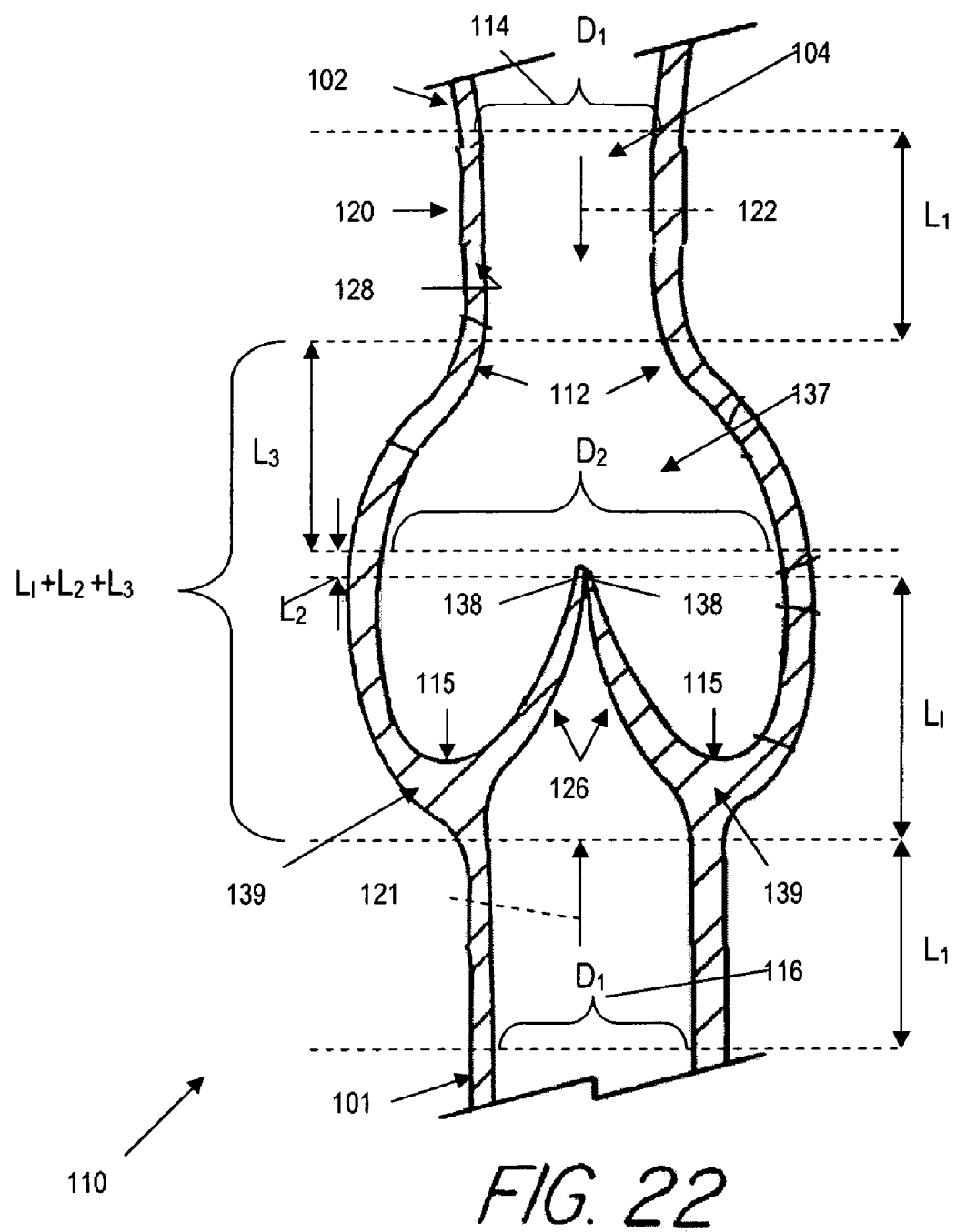
FIG. 22 depicts a cross-sectional view of a sinus having a particularly preferred geometry.

FIG. 22 shows the preferred-geometry valve 110 within a body vessel segment 120 that includes the sinus region 137 having a particularly preferred geometry that favors fluid flow in a direction 121 toward the heart. The interior wall 128 of the body vessel segment 120 defines a lumen 104 extending from the proximal end 101 to the distal end 102 of the body vessel segment 120, and including the sinus region 137. Two valve leaflets 126 are shown in the closed position, pressed together along the distal leaflet free edges 138, thereby preventing fluid flow in the retrograde direction 122. While the preferred valve 110 includes two valve leaflets 126, implantable prosthetic valves can have similar sinus geometries with one, two, three or more valve leaflets. Implantable prosthetic valves are provided that comprise one or more valve leaflets and can define a sinus region upon implantation within a body vessel. With the exception of diameters, radii and radial distance, all distances and lengths, unless otherwise indicated, are measured parallel to the central longitudinal axis of the body vessel. Preferably, an implantable medical device such as a prosthetic valve creates or defines at least a portion of a sinus region having one or more geometric characteristics of the preferred-geometry sinus 137.

Natural venous valves having a maximum internal lumen diameter of $D_1$ typically have a sinus region having a larger maximum diameter $D_2$ proximate to the site of a venous valve (i.e., $D_2$ is greater than $D_1$). Typically, natural venous valves have a ratio of $D_2/D_1$ that is about 1.67 (i.e., $D_2$ is about 67% larger than $D_1$). Preferably, the implantable medical device is a valve configured to form a sinus region upon implantation in a vein, where the sinus is characterized by dimensions similar to those of a natural venous valve. In a first embodiment, the maximum diameter of the sinus region can be about 110% to about 200%, preferably about 140% to about 180%, and most preferably about 160% to about 170% of the diameter $D_1$ of the body vessel 120 proximal 116 or distal 114 to the sinus region. In other words, the maximum diameter $D_2$ of the sinus region 137 is preferably about 10% to about 100%, preferably about 40% to about 80%, and most preferably about 60% to about 70% larger than the diameter $D_1$ of the body vessel 120 proximal or distal to the sinus region 137. Particularly preferred valve structures define a sinus region with $D_2$ being about 61, 62, 63, 64, 65, 66, 67, 68, or 70% larger than the diameter of the vessel $D_1$. The diameter of the body vessel $D_1$ proximal 116 to the sinus region is preferably measured at a longitudinal distance $L_1$ along the axis of the body vessel that can be equal to 50%-100% of the diameter $D_1$ of the body region upstream from the base of the valve leaflet. The diameter $D_1$ of the body vessel distal 114 to the sinus region can be measured at a longitudinal position along the axis of the body vessel that can be equal to one-half of the diameter of the body region downstream from the distal end of the sinus region.

In a second embodiment, the implantable medical device defines a sinus having a maximum diameter $D_2$ that is longitudinally positioned closer to one end of the frame. Preferably, the longitudinal distance $L_3$ measured along the longitudinal axis of the sinus from the intersection of the longitudinal axis with the maximum diameter $D_2$ of the sinus region 137 to the distal end 112 of the sinus region 137 is greater than half of the longitudinal length $L_S$ of the sinus region 137 (i.e., $L_1+L_2+L_3$). More preferably, $L_3$ is at least about 50% of $L_S$, including 50-80% of $L_S$, 60-70% of $L_S$ and most preferably, $L_3$ is about 67% of $L_S$.

In a third embodiment, the implantable medical device includes one or more valve leaflets having a length between about 10% and about 100%, preferably about 20% to about 50%, of the diameter $D_1$ of the body vessel proximal or distal to the sinus region. The valve leaflets 126 are positioned within the sinus region 137, which extends from a proximal end 115 to a distal sinus end 112. The body vessel 120 has a diameter $D_1$ that is substantially the same distal 114 to the sinus region 137 and proximal 116 to the sinus region 137. The sinus region 137 has a maximum diameter $D_2$ that is larger than the diameter $D_1$ of the body vessel segment 120 on either end of the sinus region 137. The sinus region 137 preferably forms a bulbous shape extending radially in a symmetric manner from the substantially cylindrical body vessel segment 120. The two valve leaflets 126 each have a length $L_1$ measured from the interior wall 138 at the leaflet base 139 to the distal leaflet free edge 138. Preferably, implantable prosthetic valves include one or more valve leaflets 126 having a length $L_1$ that is between about 10% and about 100%, more preferably about 20% to about 50%, of the diameter $D_1$ of the body vessel proximal or distal to the bulbous sinus region 137.

In a fourth embodiment, the total length of the sinus can be approximately equal to the maximum diameter of the sinus. Referring to FIG. 22, the sinus region 137 extends longitudinally from the distal sinus end 112 to the proximal sinus end 115. The length $L_S$ of the sinus region 137 is preferably equal to $L_1+L_2+L_3$, where $L_1$ is the length of the valve leaflets 126, $L_2$ is the longitudinal distance measured from the distal end of the leaflets to the portion of the sinus region 137 of the maximum diameter closest to the proximal end 115 of the sinus region, and $L_3$ is the longitudinal distance measured from the maximum diameter $D_2$ of the sinus region 137 to the distal end 112 of the sinus region 137. Notably, the distance $L_2$ can be measured as a positive number where the where the maximum diameter $D_2$ of the sinus region 137 is measured longitudinally distal to the end of the valve leaflet, or as a negative number where $D_2$ is measured longitudinally proximal to the end of the valve leaflet. For example, referring to the medical device shown in FIG. 4, the distance $L_2$ is measured as a negative distance, as the free edge of the valve leaflet is located distal to the maximum diameter of the sinus region. Referring again to FIG. 22, the distance $L_2$ is measured as a positive distance, as the free edge of the valve leaflet is positioned proximal to the maximum diameter of the sinus region. Preferably, in any medical device configuration, $L_2$ is between about $-0.5\ L_1$ and $+0.5\ L_1$, such that the end of the valve leaflets is within a longitudinal distance of the maximum diameter $D_2$ of the sinus region 137 that is about half the length of the leaflets, or less.

In a fifth embodiment, the longitudinal distance measured along the axis of the body vessel from the base of a valve leaflet to the maximum diameter of the body vessel can be at least about 50% of the length of the valve leaflet, and is preferably shaped to form a sinus pocket between a surface of the valve leaflet and the inner wall of the body vessel. Referring to the sinus region 137 in FIG. 22, the distance $L_2$ is a measured from the free edge 138 of the valve leaflets 126 to the portion of the sinus region 137 having the maximum diameter $D_2$ of the sinus region 137. $L_2$ is preferably up to about 50% of the length $L_1$ of the leaflet 126 measured toward the proximal 116 (i.e., 0 to about $-50\%\ L_1$) or distal 114 (i.e., 0 to about $+50\%\ L_1$) to the sinus region 137. In FIG. 22, the distance $L_2$ is measured as a positive number between 0 and $+0.5(L_1)$.

In a sixth embodiment, the longitudinal distance from the maximum diameter $D_2$ of the sinus region 137 to the distal end of the sinus region is preferably between about 10% and 100% of the leaflet length $L_1$. The length $L_3$ is the length of the distal sinus region measured from the maximum diameter $D_2$ of the sinus region 137. In the sinus region 137, $L_3$ can be between about $0.1(L_1)$ and about $2.0(L_1)$, more preferably between about $0.5(L_1)$ and about $1.5(L_1)$ and most preferably between about $0.75(L_1)$ and about $1.25(L_1)$.

In a seventh embodiment, the implantable medical device defines a sinus region with two or three valve leaflets of substantially equal length positioned within the sinus region, and the sinus region can be characterized by one or more of the geometric relationships described in Table 1 below.

TABLE 1

Preferred Sinus Geometric Relationships

| Variable | Minimum Value | Maximum Value |
|---|---|---|
| $D_2$ | $1.1\ (D_1)$ | $2.0\ (D_1)$ |
| $L_l$ | $0.1\ (D_1)$ | $1.0\ (D_1)$ |
| $L_1$ | $0.5\ (D_1)$ | $1.0\ (D_1)$ |
| $L_2$ | $-0.5\ (L_1)$ | $+0.5\ (L_1)$ |
| $L_3$ | $0.1\ (L_1)$ | $2.0\ (L_1)$ |
| $L_3$ | $0.5 L_s$ | $0.8 L_s$ |
| $L_s$ | $L_l + (-L_2) + L_3$ | $L_l + L_2 + L_3$ |

Referring to Table 1, $L_1$ is the length of the valve leaflets, $D_1$ is the diameter of the body vessel proximal 116 to the base of the valve leaflets, $D_2$ is the maximum diameter of the sinus region 137, $L_1$ is the longitudinal distance measured proximally along the axis of the body vessel from the base of the valve leaflets to the longitudinal position 116 where $D_1$ is measured, $L_2$ is the longitudinal distance measured from the free edge 138 of the valve leaflets to the maximum diameter $D_2$ of the sinus region 137 (can be measured in the distal 114 or proximal 116 directions, depending on the geometry of the sinus region), and $L_3$ is the longitudinal distance measured distally along the axis of the body vessel from the maximum diameter of the sinus region to the distal end of the sinus region. It is believed that implantable prosthetic devices that create a sinus region having one or more of the geometric relationships summarized in Table 1 beneficially facilitate the flow of fluid through the sinus region and mitigate or prevent incidence of thrombosis in the sinus region.

Figure 23:
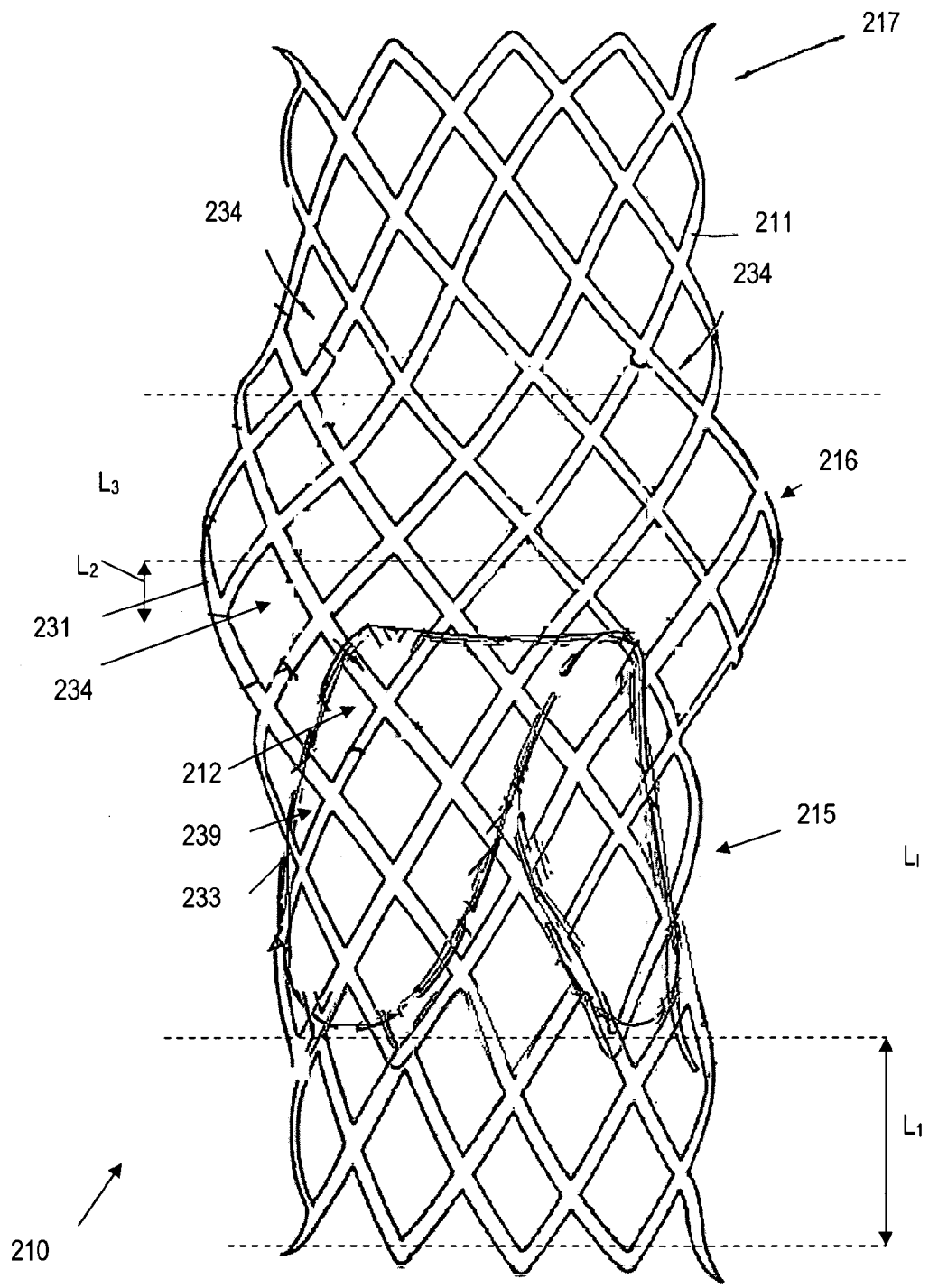
FIG. 23 depicts a cross-sectional view of a sinus formed by an implantable prosthetic valve within a body vessel.

In the embodiment of FIG. 23, an implantable valve 210 includes support frame 211 having a bulbous portion 231 defining an artificial sinus region 234 and a valve structure 212 located therein. The support frame 211 includes a proximal frame portion 215 connected to the proximal end of the bulbous expanded portion 216 of the frame (defining the sinus region 234), and a distal frame portion 217 connected to the distal end of the bulbous expanded portion 216 of the frame. The proximal frame portion 215 and the distal frame portion 217 have an annular shape, a substantially equal, diameter and a length that is at least about 50% of their respective diameters. Preferably, the proximal frame portion 215 and the distal frame portion 217 have a substantially equal diameter. The valve 210 may include a valve means. For example, one, two or three valve leaflets 239 can be sewn to the struts 233 of the support structure within the sinus region 234. The sinus region 234 can have a preferred geometry. The length of the valve leaflets $L_1$ is preferably about 35% of the diameter $D_1$ of the body vessel measured at a distance $L_1$ proximal to the sinus region 234. The total length of the sinus region $L_5$ ($L_1+L_2+L_3$) is desirably equal to the maximum diameter $D_2$ Of the sinus region. The longitudinal distance $L_2$ measured along the axis of the body vessel from the free edge of a valve leaflet to the maximum diameter of the body vessel is preferably about 30% of the leaflet length $L_1$. The maximum diameter $D_2$ of the sinus region is preferably about 60% larger than the diameter $D_1$ of the body vessel proximal to the sinus region. The distance from the end of the valve leaflets to the distal end of the sinus region is 50% larger than the diameter $D_1$ of the body vessel proximal to the sinus region.

Figure 24:
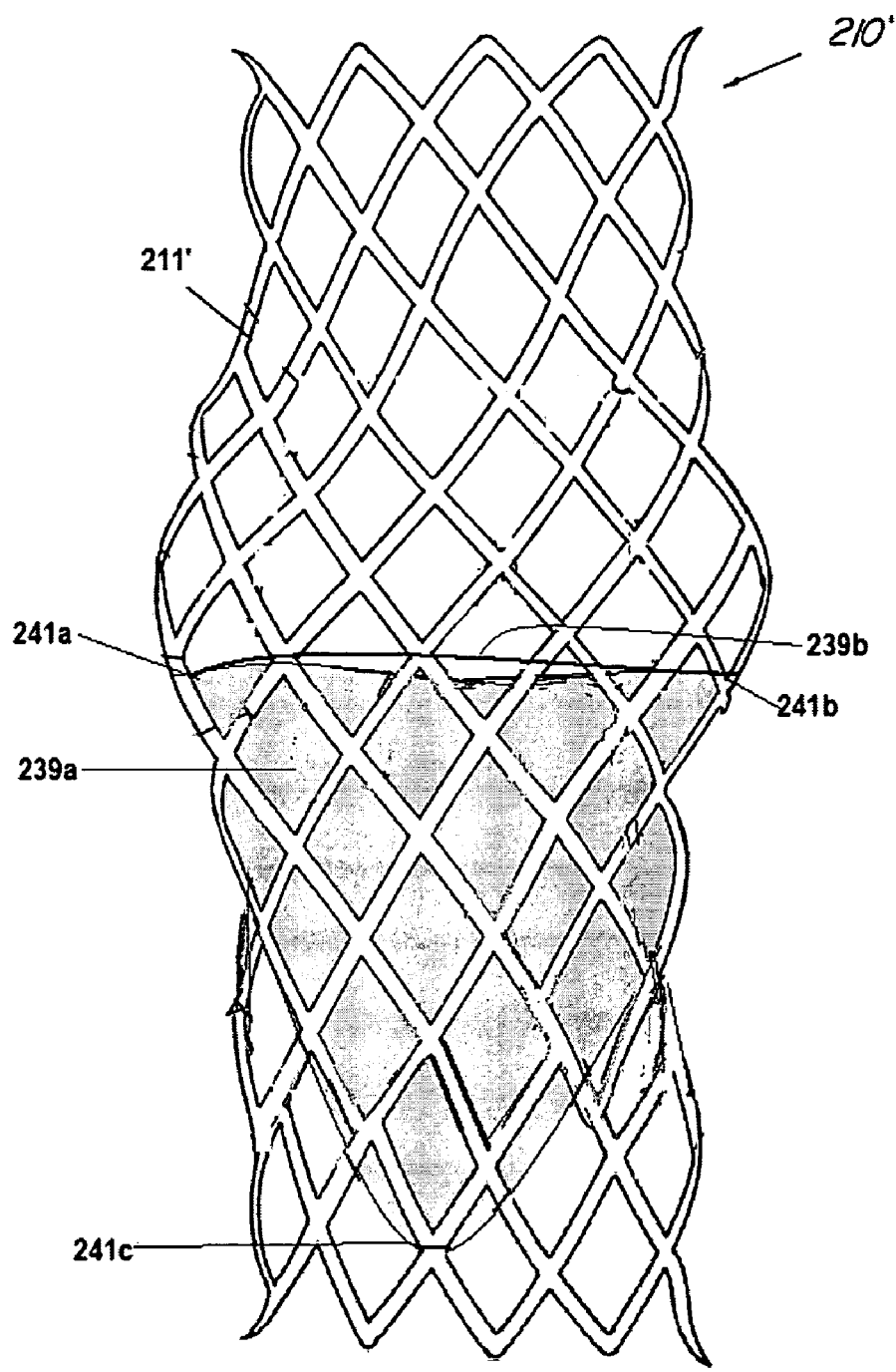
FIG. 24 is a side view of an exemplary bicuspid venous valve embodiment.

Optionally, the valve leaflets may extend laterally across the entire lumen defined by the frame. In the embodiment of FIG. 24, an implantable valve 210' includes support frame 211' having defining an artificial sinus region 234' and a valve structure comprising a pair of leaflets (239a, 239b) located therein. The valve 210' is similar to the valve 210' shown in FIG. 23, except that the leaflets (239a, 239b) extend laterally from attachment points 241a and 241b, across the entire lumen defined by the frame. The leaflet 239a is attached at point 241c at the proximal end, with both edges of the leaflet 239a sealed to the frame 211' therebetween in an arcuate configuration.

In one particularly preferred embodiment, the medical device is an expandable venous valve having a support structure configured to enlarge the area adjacent to the valve structure such that the flow patterns of retrograde flow are modified in a way that facilitates the flushing of the pockets at the base of the valve area to prevent stagnation of bodily fluid, which in the venous system can lead to thrombus formation. The enlarged pocket areas can be created by forming an artificial sinus adjacent the valve structure in an unsupported section of vessel wall between two support frame section or the support frame can comprise an expanded-diameter intermediate or proximal section that forms an artificial sinus adjacent the valve structure. The attachment pathway can be positioned between opposing leaflets and the support frame and/or vessel wall can comprise a proximal portion that places the leaflets in extended contact with one another and a distal portion forms a large angle with respect to the adjacent walls such that a large pocket can be created at the base of the leaflets. The attachment pathway can extend distally along a pair of substantially parallel longitudinal attachment struts to create an extended leaflet contact area, then angle circumferentially and distally from the former along distal attachment struts to define the bottom edge of the leaflets.

The frame can have any size and geometry suitable for intraluminal implantation. The support structure and valve structure can have any suitable configuration.

The length of the frame measured along the longitudinal axis is preferably from up to 50 mm, or preferably between 5 mm and 50 mm or higher, including 5, 6, 7, 8, 9, 10, 11, 12, 13, 14, 15, 16, 17, 18, 19, 20, 21, 22, 23, 24, 25, 26, 27, 28, 29, 30, 30, 32, 34, 35, 36, 38, 40, 42, 44, 45, 46, 48 and 50 mm, and any increment of 0.25 mm or 0.10 mm increment thereof. Some preferred embodiments have lengths of 8, 12, 13,16, 20, 23, 24, 25, 28, 32 or 33 mm. The diameter of the expanded state of the implantable frame can be selected by one skilled in the art given the desired location for implantation. When in the compressed state for delivery to a desired location within a body lumen, an implantable frame can be typically reduced from about two to about six times the diameter of the stents when in their expanded state before compression. For example, typical implantable frames may have a compressed external diameter of about 1 millimeter to about 3 millimeters for delivery and an expanded external diameter in a body lumen of about 3 millimeters to about 20 millimeters when released from compression in a large body vessel. Some implantable frames used in veins may have a compressed external diameter of about 1.00, 1.20, 1.25, 1.40, 1.50, 1.60, 1.75, 1.80, 2.00, 2.20, 2.25, 2.30, 2.40, 2.50, 2.60, 2.75, 2.80, 2.90, 3.00 mm or more and an expanded external diameter of up to about 20 mm, including between about 1 and 20 mm. Some implantable frames, for example for arterial body vessels, preferably have external diameters of 2.00, 2.20, 2.25, 2.30, 2.40, 2.50, 2.60, 2.70, 2.75, 2.80, 2.90, 3.00, 3.10, 3.20, 3.25, 3.30, 3.40, 3.50, 3.60, 3.70, 3.75, 3.80, 3.90, 4.00, 4.20, 4.25, 4.30, 4.40, 4.50, 4.60, 4.70, 4.75, 4.80, 4.90, 5.00 mm, or increments of 0.25, 0.10, 0.05 or 0.01 mm between these diameters. Other preferred embodiments, for example for implantation in veins, have expanded external diameters of between about 3 to about 25 mm, including external diameters of 3, 4, 5, 6, 7, 8, 9, 10, 11, 12, 13, 14, 15, 16, 17, 18, 19, 20, 21, 22, 23, 24, 25 mm, or any increments of 0.25, 0.10, 0.05 or 0.01 mm between these diameters. In certain preferred embodiments, the implantable frame has an expanded inner diameter of 1.25, 2.00, 2.50, 2.75, 3.00, or 3.50 mm.

The cross sectional shape of the implantable frame can be selected by one skilled in the art for particular applications, and can have the same or different shapes throughout the implantable frame or portions thereof. Suitable cross sectional dimensions of an implantable frame or portion thereof can be selected based on a variety of factors, including the intended use of the device, the material and design of the device, and other relevant concerns. The frame forming the undulating hoops, longitudinal connecting struts, or bridging members can have the same or different cross sectional shape(s). In one embodiment, the implantable frame has a square or rectangular cross sectional shape. Preferably, the undulating ring structures and the longitudinal connecting struts both have similar cross sectional dimensions. Suitable dimensions for each side of a square or rectangular cross section, or for the diameter of a circular cross section, range from 0.001-inch (0.0254 mm) to about 0.100-inch (2.54 mm). Preferably, the longest cross sectional dimension of an implantable frame member can be between about 0.001-inch (0.0254 mm) and 0.0049-inch (0.1245 mm). In one embodiment, one side of a rectangular or square cross sectional area (or diameter of a circular cross sectional area) can be between about 0.004-inch (0.102 mm) and about 0.010-inch (0.254 mm). In some embodiments, at least a portion of the frame has a strut thickness of 0.0022, 0.0025, 0.0027, 0.0036, 0.0037, 0.0049, 0.005, 0.0055, 0.006, or 0.009-inch.

For example, one preferred embodiment has an implantable frame with a width of 0.2286 mm (0.0090-inch) along the external surface of the implantable frame along the undulating ring structures and the longitudinal connecting members. In some embodiments, the implantable frame can comprise bridging members with a width of about 0.1524 mm (0.0060-inch).

In one preferred embodiment, the implantable frame has a length of 25.00 mm and an external outer diameter of 12.50 mm in the expanded state, and an outer diameter of 3.0 mm in the compressed delivery configuration.

Intraluminal Delivery

The implantable frames can be designed to be percutaneously delivered through a body lumen to a target site. The target site may be, for example, a location in the venous system adjacent to an insufficient venous valve. The implantable frames may be delivered, for example, on their own or as part of an implantable prosthetic valve. The delivery system can include a catheter having a distal end. A balloon can be positioned on the distal end of the catheter. A connector assembly can be disposed at the proximal end of the catheter and can be adapted to facilitate expansion of the balloon as can be known in the art. The connector assembly can provide access to an interior lumen of the catheter to provide access to the balloon, and possibly a guidewire or other conventional component.

A balloon expandable frame may be disposed on the distal end of the catheter. The expandable frame can surround the balloon and can be initially, prior to placement in a body vessel, in its unexpanded state. This positioning allows the balloon, upon inflation, to expand the expandable frame into its expanded state.

The medical device is desirably configured to provide artificial support to a body vessel in need thereof, for example to maintain vessel patency. This can be performed by inserting the distal end of the catheter into a body vessel and navigating the distal end, and the surrounding expandable frame, to a point in a vessel in need of artificial support. The catheter can be placed over a guidewire (not illustrated) to facilitate navigation. Once the expandable frame is at the point of treatment, the balloon can be inflated in the conventional manner. Inflation of the balloon can force the expandable frame to expand. During expansion, in which the expandable frame changes from its compressed state to its expanded state, circumferentially adjacent longitudinal connecting members can deviate from the axially-displaced configuration associated with the unexpanded state of the expandable frame, becoming substantially aligned in the axial direction. Following expansion, the balloon can be deflated, leaving the expandable frame in its expanded state. The catheter can then be withdrawn from the vessel, leaving the expandable frame in its expanded state at the point of treatment within the body vessel.

An appropriately sized delivery catheter can be selected by one skilled in the art for a given application. For example, some medical devices can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 french (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 F (1.10 mm) delivery catheters.

Implantable frames or prostheses comprising the implantable frame can be delivered into a body lumen using a system which includes a catheter. In some embodiments, implantable frames can be intraluminally delivered inside the body by a catheter that supports the implantable frame in a compacted form as it is transported to the desired site, for example within a body vessel. Upon reaching the site, the implantable frame can be expanded and securably placed within the body vessel, for example by securably engaging the walls of the body vessel lumen. The expansion mechanism may involve forcing the stent to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the implantable frame can be formed of an elastic material that will self-expand after being compacted. During introduction into the body, the implantable frame can be restrained in the radially compressed condition. When the stent has been delivered to the desired site for implantation, the restraint can be removed, allowing the implantable frame to self-expand by its own internal elastic restoring force. Once the implantable frame is located at the constricted portion of the lumen, the sheath can be removed to expose the stent, which can be expanded to contact the wall of the body vessel. The catheter can be subsequently removed from the body by pulling it in the proximal direction, through the larger lumen diameter created by the expanded medical device, which can be left in the body.

In some embodiments, the implantable frames impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed force does not traumatize the lumen walls.

The implantable frames can be placed in any medically appropriate location for a given application. For example, in some embodiments, the implantable frame can serve as part of a venous valve prosthetic and be implanted in the femoral vein, including at the proximal (groin), mid (mid section) or distal (adjacent to the knee) portions of the vein.

Frame Materials

Any suitable materials can be used to form the support structure, including metals and polymeric materials appropriate for the particular application, and depending on necessary characteristics that are required for an intended use (self-expansion, high radial force, collapsibility, etc.). The materials used for the valve structure can comprise a synthetic material or biologically-derived material appropriate for the clinical application; however, a bioremodelable material (such as an collagenous extracellular matrix (e.g., small intestinal submucosa), pericardial, or a growth factor-enhanced material may have superior anti-thrombogenic properties within the body as the native cells and tissues gradually replace the original leaflet material. The number of leaflets possible for embodiments may be one, two, three, four, or any desired number, but bi-leaflet valves may prove advantageous in low-flow venous situation as compared to tri-leaflet embodiments, such the type used as heart valves which are subject to high-flow situations where thrombus formation can be far less of a problem.

Preferred materials for implantable frames include those materials that can provide the desired functional characteristics with respect to mechanical load bearing, biological compatibility, modulus of elasticity, radio-opacity, or other desired properties. For some embodiments, the materials used to form the implantable frames can comprise a material that exhibits excellent corrosion resistance. For some embodiments, the material can be selected to be sufficiently radiopaque and create minimal artifacts during magnetic resonance imaging techniques (MRI). In some embodiments, the implantable frame can comprise a metal, a metal alloy, a polymer, or any suitable combination thereof, for example as frame with multiple layers.

Preferably, the implantable frames are self-expanding stents comprising a material capable of significant recoverable strain to assume a low profile for delivery to a desired location within a body lumen. After release, a radially-compressed self-expanding stent can radially expand back to its original diameter. Accordingly, some embodiments provide frames made from material with a low yield stress (to make the frame deformable at manageable balloon pressures), high elastic modulus (for minimal recoil), and can be work hardened through expansion for high strength. Particularly preferred materials for self-expanding implantable frames are nickel titanium alloys and other alloys that exhibit superelastic behavior, i.e., are capable of significant distortion without plastic deformation. Frames manufactured of such materials may be significantly compressed without permanent plastic deformation, i.e., they are compressed such that the maximum strain level in the stent can be below the recoverable strain limit of the material. Discussions relating to nickel titanium alloys and other alloys that exhibit behaviors suitable for frames can be found in, e.g., U.S. Pat. No. 5,597,378 (Jervis) and WO 95/31945 (Burmeister et al.). Nickel titanium alloys suitable for use in manufacturing implantable frames can be obtained from, e.g., Memry Corp., Brookfield, Conn. One suitable material possessing desirable characteristics for self-expansion can be Nitinol, a Nickel-Titanium alloy that can recover elastic deformations of up to 10 percent. This unusually large elastic range can be commonly known as superelasticity.

In some embodiments, the implantable frames are designed to be expanded by a balloon or some other device (i.e., the frames are not self-expanding). The frame may be manufactured from an inert, biocompatible material with high corrosion resistance that can be plastically deformed at low-moderate stress levels, such as tantalum. The implantable frames can be deployed by both assisted (mechanical) expansion, i.e. balloon expansion, and self-expansion means. In embodiments where the implantable frame can be deployed by mechanical (balloon) expansion, the implantable frame can be made from materials that can be plastically deformed through the expansion of a mechanical assist device, such as by the inflation of a catheter based balloon. When the balloon can be deflated, the frame can remain substantially in the expanded shape. Other acceptable materials include stainless steel, titanium ASTM F63-83 Grade 1, niobium or high carat gold K 19-22. One widely used material for balloon expandable structures can be stainless steel, particularly 316L stainless steel. This material can be particularly corrosion resistant with a low carbon content and additions of molybdenum and niobium. Fully annealed, stainless steel can be easily deformable. Alternative materials for mechanically expandable structural frames that maintain similar characteristics to stainless steel include tantalum, platinum alloys, niobium alloys, and cobalt alloys.

In addition, the frames may be formed from, or coated with, other materials such as polymers and bioabsorbable polymers. In one embodiment, the implantable frame can be formed from 316L stainless steel. In another embodiment, the implantable frame can be formed from a cobalt chromium alloy. The implantable frames can also comprise (that is, be formed from or coated with) a variety of polymers such as: polyethylene (PE); polypropylene (PP); polyisobutylene; poly(alpha olefin); alkyl (alkyl)acrylates such as poly(n-butyl methacrylate) (PBMA) poly(methyl acrylate) or poly(methyl methacrylate) (PMMA); poly(ethyl acrylate); parylenes such as parylene C; ethyl vinyl acetate (EVA); poly(ethylene-co-vinyl acetate) (PEVA), or copolymers or mixtures thereof.

For some embodiments, it can be desirable to provide implantable frames comprising bioabsorbable polymers. Bioabsorbable materials absorb into the body after a period of time. The period of time for the structural frame to absorb may vary, but can be typically sufficient to allow desired biological processes such tissue growth to occur at the implant location. The implantable frames can comprise one or more bioabsorbable materials. A wide variety of bioabsorbable materials are known in the art, as well as equivalents thereof, can be used to form implantable frame. Nonlimiting examples of bioabsorbable polymers include polyesters such as poly(hydroxyalkanoates), poly(lactic acid) or polylactide (PLA), poly(glycolic acid) or polyglycolide (PGA), poly(caprolactone), poly(valerolactone) and co-polymers thereof; polyoxaesters such as poly(ethylene oxalate), poly(alkylene oxalates); polyanhydrides; poly(amino acids); polyphosphazenes; hydrogels; polydioxanone, poly(DTE carbonate), and co-polymers or mixtures of two or more polymers. The implantable frames can also include various natural polymers such as fibrin, collagens, extracellular matrix (ECM) materials, dextrans, polysaccharides and hyaluronic acid.

The disclosure of various materials for forming the structural frame should not be construed as limiting the scope of possible frame materials. One of ordinary skill in the art would understand that other materials possessing similar characteristics may also be used in the construction of the implantable frame.

Implantable Medical Devices Comprising Bioactive Agents

Optionally, the support frame or a material attached thereto, such as a valve leaflet or graft material, can include one or more bioactive materials. Preferably, the bioactive material can be releasably associated with the frame, meaning that the bioactive material can be released from a medical device comprising the frame upon implantation. Releasably associated bioactive materials can be attached to the medical device in any suitable manner, including incorporation of the bioactive material within the frame material, attachment of the bioactive material to the frame material or incorporation of the bioactive material in one or more coatings applied to the frame material.

The bioactive material can be selected to treat indications such as thrombosis, coronary artery angioplasty, renal artery angioplasty, carotid artery surgery, renal dialysis fistulae stenosis, or vascular graft stenosis. The bioactive agent can be selected to perform one or more desired biological functions. An anti-angiogenic or antineoplastic bioactive such as paclitaxel, sirolimus or a rapamycin analog, or a metalloproteinase inhibitor such as batimastaat can be incorporated in or coated on the frame to mitigate or prevent undesired conditions in the vessel wall, such as restenosis. Many other types of bioactive agents can be incorporated in or coated on a support frame.

Medical devices comprising an antithrombogenic bioactive material are particularly preferred for implantation in areas of the body that contact blood. An antithrombogenic bioactive material can be any bioactive material that inhibits or prevents thrombus formation within a body vessel. The medical device can comprise any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid can be dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin. Further examples of antithrombotic bioactive materials include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, Cl-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive materials such as endothelial progenitor cells or endothelial cells.

Bioactive materials for use in bio-compatible coatings include those suitable for coating on an implantable medical device. The bioactive agent can include, for example, one or more of the following: antiproliferative agents (sirolimus, paclitaxel, actinomycin D, cyclosporin), immunomodulating drugs (tacrolimus, dexamedthasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

A bioactive material can be one or more pro-healing therapeutic agents, which include materials that provide or promote endothelial cell seeding. For instance, coatings comprise antibodies to CD34 receptors on progenitor circulating endothelial cells. Nitric oxide, vascular endothelial growth factor, and 17-β-estradiol are other examples of prohealing therapeutic agents. Another prohealing bioactive agent can be vascular endothelial growth factor (VEGF). VEGF can be an endothelial cell-specific mitogen, and a cytokine involved in processes essential to the growth, maintenance and repair of vascular structures. VEGF can be coated on an implantable frame. Local drug delivery of VEGF from a medical device, such as a stent frame, can reduce in-stent restenosis. Other examples of pro-healing therapeutic agents, along with methods for coating the same on implantable medical devices, are provided in published U.S. Patent Application Nos. 2005/0092440 (filed Nov. 8, 2002, by Weinstein); 2005/0191333 (filed Apr. 28, 2005 by Hsu); and 2005/0148585 (filed Aug. 26, 2004 by Davies et al.), which are incorporated herein by reference.

Various other bioactive materials can be incorporated on or in the frame, including one or more of the following: antiproliferative/antimitotic agents including natural products such as vinca alkaloids (i.e. vinblastine, vincristine, and vinorelbine), epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as (GP) II b/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i. e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat) and protease inhibitors. Other examples of bioactive coating compounds include antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR agonist and RXR agonists, as disclosed in published U.S. Patent Application US2004/0073297 to Rohde et al., published on Apr. 15, 2004 and incorporated in its entirety herein by reference.

The device can be coated with polysaccharides, for example as disclosed in published U.S. Patent Application US2004/091605 to Bayer et al., published on May 13, 2004 and incorporated herein by reference in its entirety. In one embodiment, the frame comprises a polysaccharide layer which has improved adhesion capacity on the substrate surface of the frame. For example, the coated frame can comprise the covalent bonding of a non-crosslinked hyaluronic acid to a substrate surface of the frame with the formation of hyaluronic acid layer and crosslinking of the hyaluronic acid layer.

The bioactive materials can be attached to the medical device in any suitable manner. For example, a bioactive can be attached to the surface of the medical device, or be positioned within the frame in pores. One or more bioactives can be coated on or incorporated within a frame. In one embodiment, a frame can be configured to absorb a solution of a bioactive material. For instance, a frame with absorbent properties can be selected, or a portion of a medical device can be coated with a cross-linked polymer hydrogel material to retain a bioactive material for elution within a body vessel. A bioactive can be incorporated by soaking the absorbent portion of the medical device in a solution of the bioactive material and allowing the absorption of the bioactive solution. Subsequently, the solvent can be evaporated to leave the bioactive within the medical device.

In another embodiment, a frame can also be coated with or formed from a biodegradable polymers, as well as copolymers of degradable polymers. A bioactive material can be mixed with or copolymerized with the bioabsorbable polymer. Alternatively, the bioactive material or a mixture of bioactive material and biostable or bioabsorbable polymer can be coated with a second layer comprising a bioabsorbable polymer. Upon implantation, absorption of the bioabsorbable polymer releases the bioactive. Bioabsorbable polymers can be formed by copolymerization of compatible monomers or by linking or copolymerization of functionalized chains with other functionalized chains or with monomers. Examples include crosslinked phosphorylcholine-vinylalkylether copolymer and PC-Batimastat copolymers. In one embodiment, the frame can be coated with a coating of between about 1 μm and 50 μm, or preferably between 3 μm and 30 μm, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier can be a bioabsorbable material, and one preferred carrier can be poly-L-lactic acid. U.S. patent application Ser. No. 10/639,225, filed Aug. 11, 2003 and published as US2004/0034409A1 on Feb. 19, 2004, describes methods of coating a bioabsorbable metal support frame with bioabsorbable materials such as poly-L-lactic acid that are incorporated herein by reference.

Methods of Manufacture

The implantable frames may be fabricated using any suitable method known in the art. Preferably, the complete frame structure can be cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame can be constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which can be incorporated herein by reference in its entirety.

In some embodiments, connections between the strut members and the bends in an undulating ring structure, as well as the connection between the undulating ring structure and the longitudinal connecting members, may be formed by welding or other suitable connecting means. Other connection means include the use of a binder, heat, or chemical bond, and/or attachment by mechanical means, such as pressing, welding or suturing. In addition, portions of the frame may be attached by applying a bonding coating.

An implantable frame can optionally be sterilized using any suitable technique known in the art, or equivalents thereto. For example, an implantable frame can be sterilized using ethylene oxide sterilization, as described in AAM/ISO 11135:1994 "Medical Devices—Validation and Routine Control of Ethylene Oxide Sterilization," incorporated herein by reference in its entirety. In some embodiments, a sterilized implantable frame satisfies a minimum Sterility Assurance Level (SAL) of about $10^{-6}$.

One preferred method of manufacture includes the steps of: providing a frame defining a lumen extending between a proximal end and a distal end along a longitudinal axis, the frame comprising a substantially annular distal frame end with a first diameter at the distal end and a sinus-forming frame portion proximal to the distal end, the sinus-forming frame portion having a maximum diameter of about 10% to about 200% larger than the first diameter; and attaching a valve leaflet comprising an extracellular matrix material to the frame within the lumen, the valve leaflet configured and positioned to define a sinus region within the lumen between the valve leaflet and the frame, the valve leaflet having a length measured from a base attached to the frame to a flexible free edge, the free edge moveable in response to fluid flow through the lumen. A "sinus-forming frame portion" refers to a portion of an implantable frame or valve that defines at least part of a sinus region upon implantation within a body vessel. Preferably, the valve leaflet is a dried extracellular matrix material attached to the frame within the lumen in a manner that reduces the diameter of at least a portion of a self-expanding frame. When the extracellular matrix material is placed in a fluid conducting body vessel, wetting of the material may permit gradual radial expansion of the self-expanding frame.

Vascular prostheses such as stent and stent/grafts undergo a number of different strain conditions in-vivo including: radial strain resulting from the applied diastolic and diastolic blood pressure, bending due to heart/limb movement and radial point loading due to limb motion or impact.

A variety of techniques can be used to measure and control the radial strains applied to vascular prostheses in bench-top simulators. A first technique involves applying a known volumetric fluid displacement to a vascular medical device that has been installed in a mock artery of known radial compliance. The volumetric displacement can be adjusted until the applied pressure closely simulates diastolic and diastolic conditions. The resulting radial strain can then be calculated as known in the art, for example with a formula that uses the volumetric displacement and mock artery dimensions. A second technique involves measuring the radial strain of the outside diameter of the mock artery using a laser micrometer. The internal radial strain can then be determined by multiplying the outside strain by a ratio that has been calculated using the outside and inside diameters and poison ratio of the mock artery material.

The implantable frames can be tested by placing them inside latex tubes filled with a phosphate buffered saline (PBS) solution and pulsating the tube volume to simulate physiological vessel compliance conditions (typically 3-5%). The tubes deflect radially with the applied pulsitile pressure. The assembly acts as a mechanical system, producing strain levels on the device comparable to the vessel-valve system of the human body. A laser transducer can be used to measure the tube dilation in real-time; WinTest uses the resulting signal to control the dilation within preset levels. At various intervals during the durability test, the devices can be removed and examined for mechanical integrity under a scanning electron microscope or with an endoscope assembly. A list of potential failure modes and potential tests that were identified by the AAMI/ISO TG150, SC2, WG31 committee in developing their working document for endovascular devices, incorporated herein by reference.

For intravascular applications, the use of x-ray angiography, pressure catheters, or intravascular ultrasound provides a good means for determining the radial dilation and pressures that occur during each heartbeat or extraneous movement. Combining measured data with finite element modeling provides a better understanding of the test parameters that must be generated.

A variety of other test protocols can also be used. Information provided on the FDA Web site about previously approved devices can be useful in developing test protocols. Published papers and articles about applied loading in relevant publications, for example in the orthopedic and intravascular fields. For example, Conti et al., *Biomed Sci Instrum* 35:339-46

(1999), incorporated herein by reference, discusses testing of intravascular implantable frames.

Kits comprising implantable frames are also provided. In one embodiment, a kit comprises an implantable medical device and a delivery catheter.

Methods of Treatment

Implantable frames can be deployed at various locations and lumens in the body, such as, for example, coronary, vascular, nonvascular and peripheral vessels, ducts, and the like, including but not limited to cardiac valves, venous valves, valves in the esophagus and at the stomach, valves in the ureter and/or the vesica, valves in the biliary passages, valves in the lymphatic system and valves in the intestines. In one embodiment, a valve leaflet can be attached to the frame to provide an implantable valve that can be implanted within a vein, for instance, near an incompetent venous valve to treat venous valve insufficiency.

Methods of treatment preferably include the steps of loading an implantable frame, or a device comprising an implantable frame, in a compressed state into a delivery catheter, inserting the delivery catheter into a body vessel, translating the delivery catheter to a desired location, deploying the device comprising the implantable frame by securably placing the device in an expanded state at the desired location, and withdrawing the delivery catheter from the body vessel.

Methods for treating certain conditions are also provided, such as venous valve insufficiency, varicose veins, esophageal reflux, restenosis or atherosclerosis. In some embodiments, the invention relates to methods of treating venous valve related conditions. A "venous valve related condition" is any condition presenting symptoms that can be diagnostically associated with improper function of one or more venous valves. In mammalian veins, natural valves are positioned along the length of the vessel in the form of leaflets disposed annularly along the inside wall of the vein which open to permit blood flow toward the heart and close to prevent back flow. These natural venous valves act as open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. Functioning leaflets return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve related conditions are chronic venous insufficiency and varicose veins.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood may collect, or pool, in vessels beneath the valve. This pooling of blood can cause an increase in the venous pressure below the valve. Venous valves that allow such deleterious retrograde flow are known as incompetent or inadequate venous valves. The condition resulting from such incompetent venous valves is known as venous valve insufficiency. In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

Accordingly, methods of treating a venous valve related condition may comprise the step of providing one or more medical devices comprising implantable frames as described herein. Methods of treatment may comprise the step of providing one or more frames attached to one or more valve leaflets. In some embodiments, methods of treatment may also include the steps of delivering a medical device to a point of treatment in a body vessel, and deploying a medical device at the point of treatment, wherein the medical devices are as described herein. Such medical devices can be inserted intravascularly, for example from an implantation catheter. The medical devices can function as a replacement venous valve, or enhance venous valve function by bringing incompetent valve leaflets into closer proximity. In one procedure, venous valve function can be provided by an implanted medical device.

In accordance with certain methods of treatment, a medical device comprising an implantable frame may be placed in a human leg having greater saphenous vein (GSV) and femoral vein which adjoin at the sapheno-femoral junction. Preferably, the medical device is implanted within the GSV near the medial side of the knee and a point prior to the sapheno-femoral junction. Desirably, the medical device functions as a valve to prevent or reduce reflux of venous blood from the sapheno-femoral junction in a direction down toward the medial side of the knee. Such occlusion may be effective to treat varicosities that commonly occur in lower portions of the leg, e.g. portions occurring below the knee.

The medical device is preferably implanted from a delivery catheter via percutaneous access to the GSV, for example by the Seldinger technique or any other suitable technique. For instance, an access needle can be passed through the skin to access the GSV, and a wire guide can be passed through the access needle and into the vein. Prior to deployment of an inverted occlusion device, wire guide can be used for any number of conventional procedures including catheterization and imaging procedures in order to locate the sapheno-femoral junction. After any such preliminary procedures that are performed, the wire guide can be used in a deployment procedure for an inflatable occlusion device.

Methods for delivering a medical device as described herein to any suitable body vessel are also provided, such as a vein, artery, billiary duct, ureteral vessel, body passage or portion of the alimentary canal. The invention includes other embodiments within the scope of the claims, and variations of all embodiments.

EXAMPLES

Twelve radially self-expanding medical devices were percutaneously implanted from a catheter in sheep jugular veins from and were explanted at 1 month or 3 months later. Each of the twelve medical devices includes a tubular frame 300, shown in FIG. 25, having a bulbous sinus forming portion with a maximum diameter positioned between cylindrical distal and proximal ends each having a smaller diameter. The frame 300 was formed from a network of interconnected struts and bends formed from a self-expanding nitinol nickel-titanium alloy. The frame 300, shown in FIG. 25, has a maximum diameter of 20 mm at D2 and a diameter of 14 mm formed by a first sinusoidal hoop member 315' at the proximal end 302 and the same diameter formed by a second sinusoidal hoop member 315 at the distal end 304. A sinusoidal hoop member 314 with a diameter of 20 mm is positioned between, and joined to, the first sinusoidal hoop member 315' and the second sinusoidal hoop member 315, by a first plurality of connecting struts 306 and a second plurality of connecting struts 312. The maximum diameter D2 of the frame 300 is defined by the connection of the first plurality of connecting struts 306 to the first sinusoidal hoop member 315'.

Figure 25:
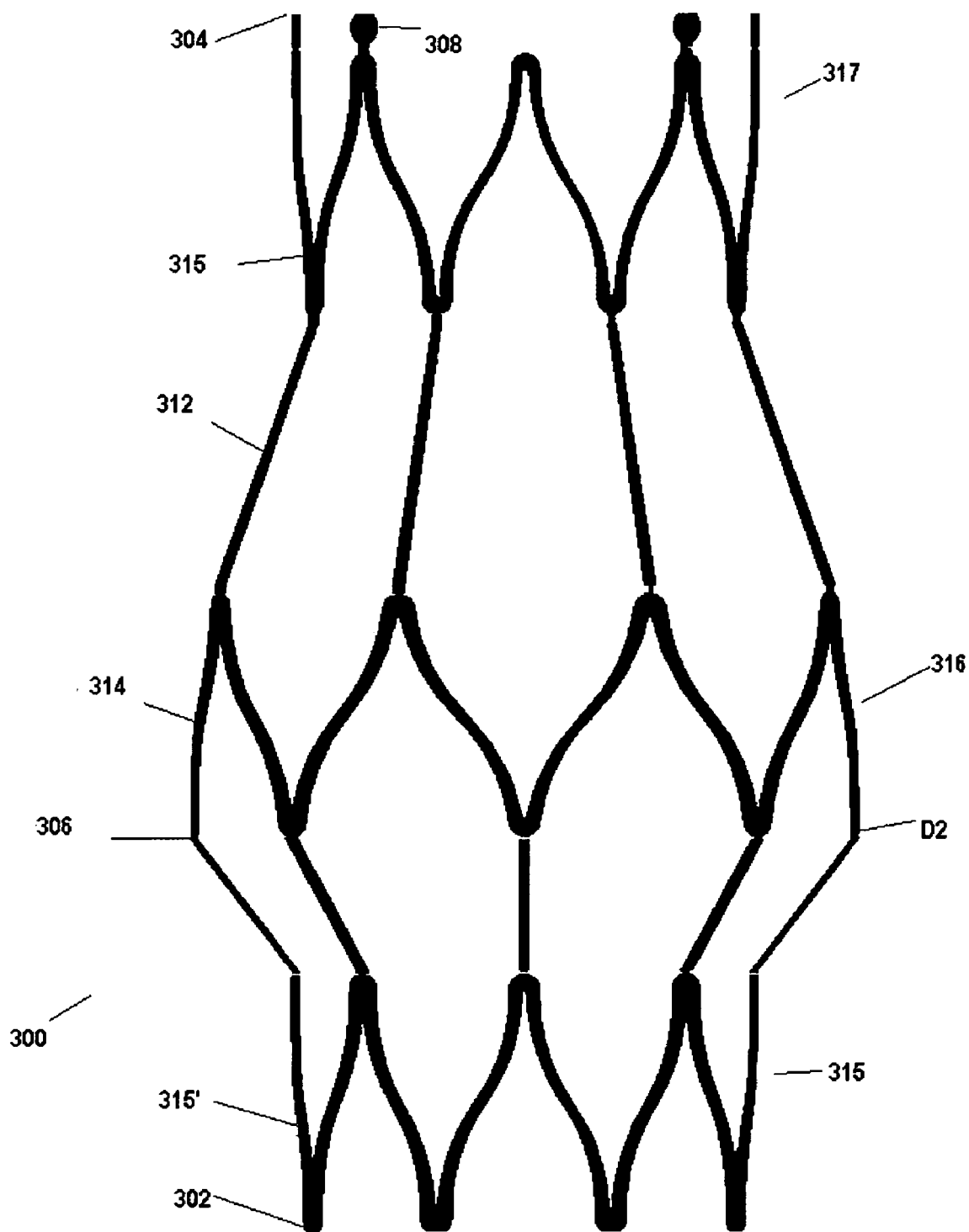
FIG. 25 is a side view of an exemplary implantable frame having a preferred geometry sinus region.
Figure 26A:
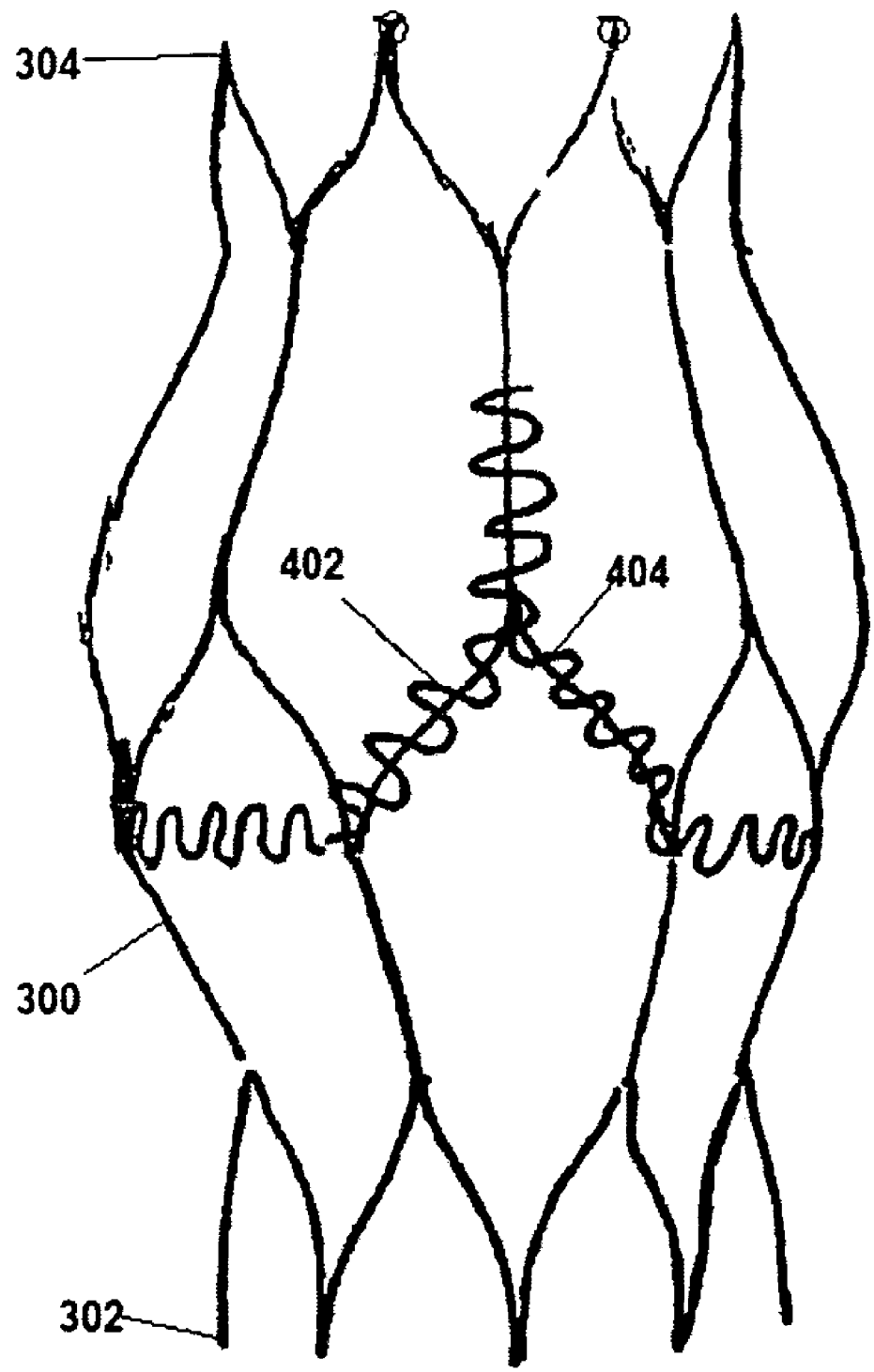
FIG. 26A is a side view of an exemplary bicuspid venous valve embodiment.
Figure 27A:
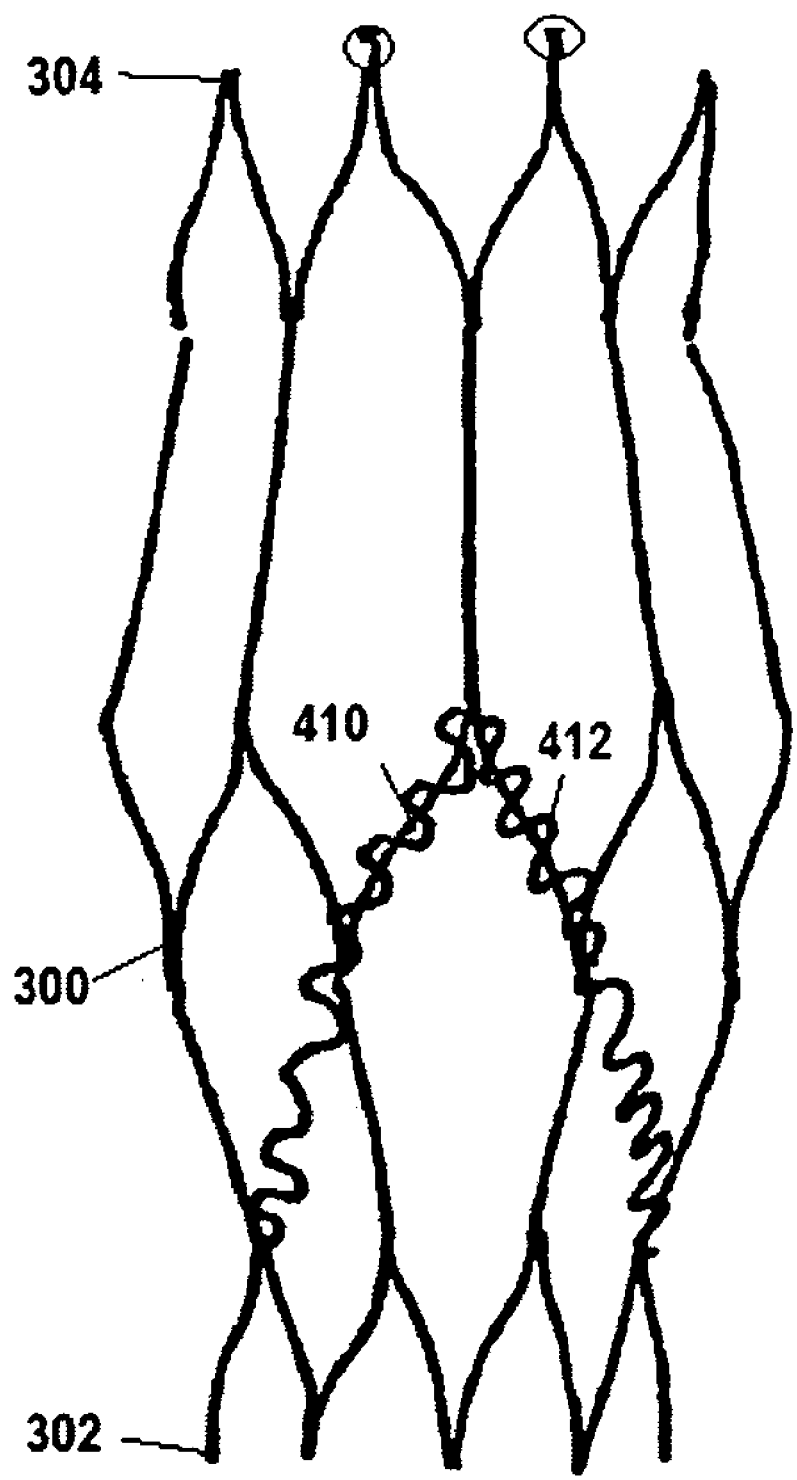
FIG. 27A is a side view of an exemplary bicuspid venous valve embodiment.

The twelve implanted medical devices were each selected from three different configurations: four of the medical devices consisted of the frame 300 shown in FIG. 25 alone, four of the medical devices were formed by attaching two valve leaflets 402, 404 to the frame 300 in a shallow-pocket valve configuration shown in FIG. 26A, and four of the medical devices were formed by attaching two valve leaflets 410, 412 to the frame 300 in a deep-pocket configuration shown in FIG. 27A. The frame configuration of frame 300 used in all twelve medical devices was formed from a self-expanding nitinol (niti alloy) material. All of the valve leaflets (402, 404; 410, 412) were formed from lyophilized small intestine submucosa. The medical device depicted in FIG. 26A exhibited leaflets 402, 404 positioned with the full length of the leaflets 402, 404 within the sinus portion of the frame. The medical devices shown in FIG. 27A were constructed with leaflets 410, 412 extending from a base positioned at the smaller diameter of the stent where the sinus begins to a leaflet free edge positioned at the widest portion of the stent frame. Both designs had valve leaflets extending laterally across the entire lumen of the device.

The medical devices were implanted from a delivery catheter into sheep jugular veins at a site having a vein diameter less than the diameter of the bulbous sinus-forming portion of the medical devices. The medical devices were explanted at 1 month and 3 months. Each medical device expanded within the body vessel due to accommodation by the vein to the self-expanding force of the frame. The results are summarized in Table 2 as a ratio of the maximum diameter of the vein at the point of implantation ($D_2$) to the vein diameter proximal to the medical device ($D_1$). The accommodation of the vein to the radial self-expanding force of the frame resulted in an increased ratio in Table 1 at 1 and 3 months, while remodeling of the small intestine submucosal valve leaflets was examined over a 1 month time period.

TABLE 2

| ratio of maximum diameter of medical device to vein diameter | | | |
|---|---|---|---|
| | Frame Only | Valve Config. 1 | Valve Config. 2 |
| At implant | 1.056 | 1.128 | 1.128 |
| 1 month explant | 1.336 | 1.325 | 1.420 |
| 3 months explant | 1.521 | n/a | n/a |

Figure 26B:
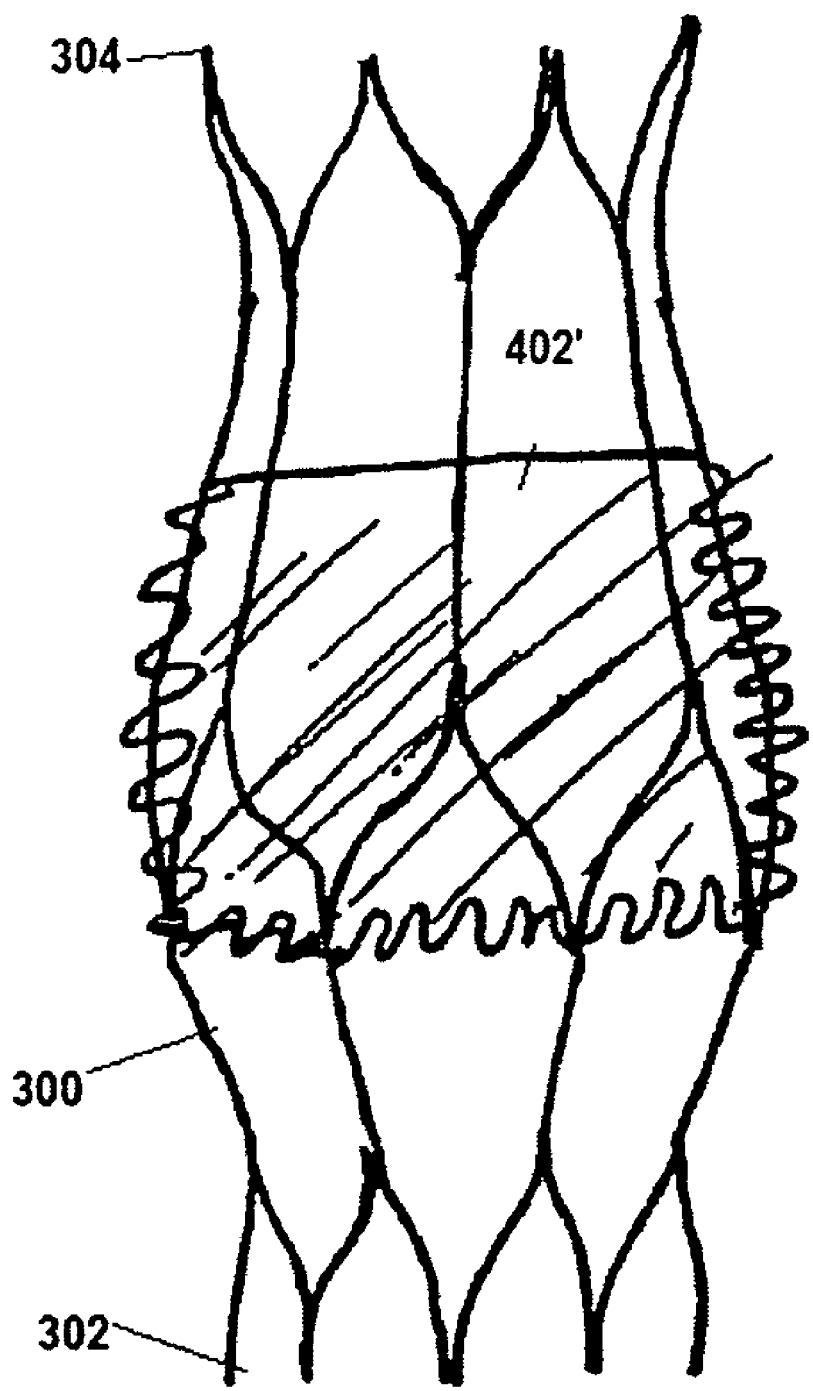
FIG. 26B is a side view of an exemplary monocuspid venous valve embodiment.
Figure 27B:
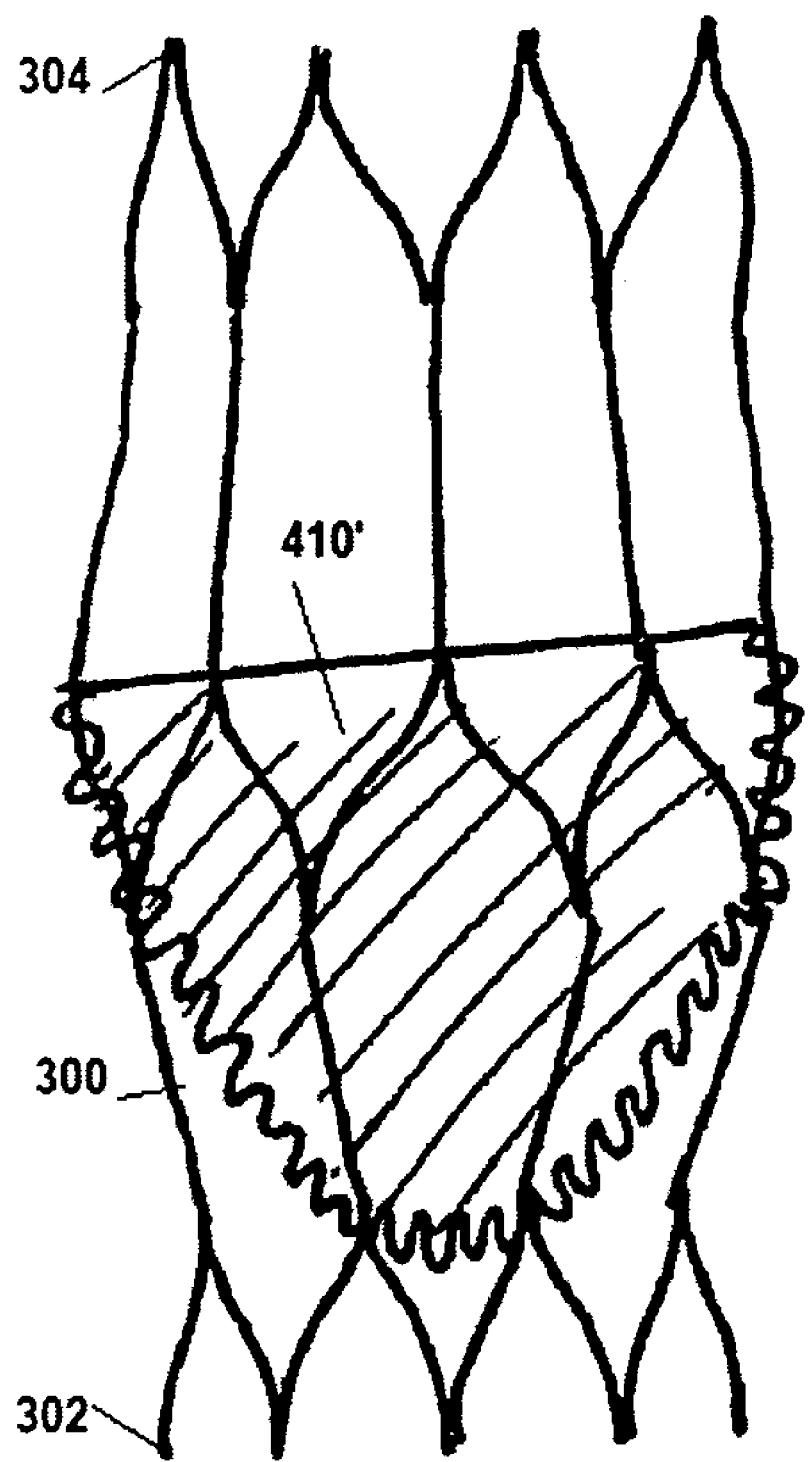
FIG. 27B is a side view of an exemplary monocuspid venous valve embodiment.

Two alternative, monocuspid valve configurations are shown in FIG. 26B and FIG. 27B. The valve shown in FIG. 26B is formed by attaching a single leaflet 402' to the frame 300 between the proximal end 302 and the distal end 304. Similarly, FIG. 27B shows a valve configuration having a single valve leaflet 410' attached to the frame 300 between the proximal end 302 and the distal end 304 of the frame 300. The valves shown in FIG. 26B and FIG. 27B are axially rotated by 90-degrees with respect to the views of FIG. 26A and FIG. 27A, respectively.

Illustrative embodiments of the present invention have been described in considerable detail for the purpose of disclosing a practical, operative structure whereby the invention may be practiced advantageously. The designs described herein are intended to be exemplary. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27th edition.

What is claimed:
1. An implantable valve comprising:
   a frame defining a lumen extending between a proximal end and a distal end along a longitudinal axis, the frame comprising a proximal frame portion having a substantially annular shape with a first diameter at the frame proximal end and a sinus-forming frame portion having a distal end and a proximal end connected to the proximal frame portion, the sinus-forming frame portion having a bulbous shape with a maximum diameter of about 10% to about 200% larger than the first diameter to define a sinus region; and a valve leaflet having a body with a base and a flexible free edge, the valve leaflet base attached to the proximal frame portion within the lumen, the valve leaflet extending from the base, into the sinus region and terminating with the free edge before the maximum diameter of the sinus-forming frame portion so that the valve leaflet free edge is located within the sinus region, the valve leaflet defining a sinus pocket within the lumen between the valve leaflet body and the sinus-forming frame portion, the valve leaflet having a length measured from the base to the flexible free edge, the free edge moveable in response to fluid flow through the lumen;

wherein the maximum diameter of the sinus-forming frame portion is positioned between the distal and proximal end of the sinus-forming frame portion such that a longitudinal distance from one of the proximal end and the distal end of the sinus-forming frame portion to the maximum diameter is less than a longitudinal distance from the other of the proximal end and the distal end of the sinus-forming frame portion to the maximum diameter; and wherein the frame comprises struts.

2. The implantable valve of claim 1, wherein the maximum diameter of the sinus-forming frame portion is positioned between the distal and proximal end of the sinus-forming frame portion such that the longitudinal distance from the proximal end of the sinus-forming frame portion to the maximum diameter is less than the longitudinal distance from the distal end of the sinus-forming frame portion to the maximum diameter.

3. The implantable valve of claim 2, wherein the longitudinal distance from the proximal end of the sinus-forming frame portion to the longitudinal position of the maximum diameter of the sinus-forming frame portion is about 30-40% of the distance between the distal end and the proximal end of the sinus-forming frame portion.

4. The implantable valve of claim 1, wherein the length of the valve leaflet is between about 10% to about 100% of the first diameter of the proximal frame portion.

5. The implantable valve of claim 1, wherein the maximum diameter of the sinus-forming frame portion is approximately equal to a distance measured along the longitudinal axis of the frame from the free edge of the valve leaflet to the distal end of the sinus-forming frame portion.

6. The implantable valve of claim 1, wherein the distance measured along the longitudinal axis of the frame from the base of the valve leaflet to the maximum diameter of the sinus-forming frame portion is equal to between about 50% and 150% of the length of the value leaflet.

7. The implantable valve of claim 1, wherein the distance measured along the longitudinal axis of the frame from the maximum diameter to the distal end of the sinus-forming frame portion is between about 10% and about 200% of the leaflet length.

8. The implantable valve of claim 1, wherein the frame further comprises a bioactive material releasably attached to at least a portion of the implantable valve.

9. The implantable valve of claim 1, further comprising a distal frame portion having a substantially annular shape with a second diameter at the frame distal end, wherein the maximum diameter of the sinus-forming frame portion is about 60% to about 70% greater than the first diameter and about 10% to about 200% larger than the second diameter.

10. The implantable valve of claim 9, wherein the frame is radially moveable from a compressed state to a radially expanded state; wherein the leaflet length is between about 20% to about 50% of the first diameter; wherein the first diameter is substantially equal to the second diameter; wherein the maximum diameter of the sinus region is about 60% to about 70% larger than each of the first diameter and the second diameter; wherein the maximum diameter of the sinus-forming frame portion is approximately equal to a distance measured along the longitudinal axis of the frame from the free edge of the valve leaflet to the distal end of the sinus-forming frame portion; and wherein the distance measured along the longitudinal axis of the frame from the free edge of the valve leaflet to the maximum diameter of the sinus region is equal to about 20% to about 40% of the first diameter.

11. An implantable valve comprising a frame and a valve means attached to the frame; wherein the frame defines a lumen extending between a proximal end and a distal end along a longitudinal axis, the frame being radially symmetrical along the longitudinal axis and moveable from a compressed configuration to a radially expanded configuration, the frame comprising a substantially cylindrical proximal frame portion including the proximal frame end, a substantially cylindrical distal frame portion including the distal frame end and a sinus frame portion having a bulbous shape defining a sinus region, the sinus frame portion being positioned between and connected to the proximal frame portion and the distal frame portion; wherein each of the proximal frame portion and the distal frame portion has a first diameter and wherein at least a portion of the sinus frame portion has a maximum diameter that is about 10% to about 200% larger than the first diameter; and wherein at least a portion of the valve means defines a portion of the sinus regions;

wherein the valve means comprises one or more valve leaflets having a body with a base and a flexible free edge, the valve leaflet base attached to the proximal frame portion within the lumen, the valve leaflet extending from the base, into the sinus region and terminating with the free edge before the maximum diameter of the sinus frame portion so that the valve leaflet free edge is located within the sinus region;

wherein the maximum diameter of the sinus frame portion is positioned between the distal and proximal end of the sinus frame portion such that a longitudinal distance from one of the proximal end and the distal end of the sinus frame portion to the maximum diameter is less than a longitudinal distance from the other of the proximal end and the distal end of the sinus frame portion to the maximum diameter; and wherein the frame comprises struts.

12. The implantable valve of claim 11, wherein the length of the sinus region measured along the longitudinal axis of the frame from a distal end of the proximal frame portion to a proximal end of the distal frame portion, is approximately equal to the maximum diameter of the sinus frame portion.

13. The implantable valve of claim 11, wherein the length of the proximal frame portion measured along the longitudinal axis of the frame is about 50% to about 100% of the first diameter of the proximal frame portion.

14. The implantable valve of claim 11, wherein the valve means comprises one or more valve leaflets having a body with a base and a flexible free edge, the valve leaflet base attached to the proximal frame portion within the lumen, the valve leaflet extending distally from the leaflet base to the leaflet free edge and radially inward into the sinus region, the leaflet length being about 10% to about 100% of the first diameter of the proximal frame portion.

15. The implantable valve of claim 14, wherein the distance measured along the longitudinal axis of the frame from the most proximal portion of the sinus region having the maximum diameter to the distal end of the sinus region is between about 10% and about 200% of the leaflet length.

16. The implantable valve of claim 14 wherein the portion of the sinus frame portion having the maximum diameter is about 60% to about 70% larger than the first diameter, wherein the valve leaflet free edge is located within the sinus region to define a sinus pocket between the valve leaflet body and the sinus frame portion, the free edge moveable in response to fluid flow through the lumen between an open position during antegrade flow and a closed position during retrograde flow, wherein during retrograde flow each defined sinus pocket is adapted to enhance the movement of fluid flow within the sinus pocket such that fluid stagnation is inhibited.

17. An implantable valve comprising:
  a frame defining a lumen extending between a proximal end and a distal end along a longitudinal axis, the frame having a bulbous portion interposed between a proximal portion and a distal portion, the bulbous portion defining a sinus region having a maximum diameter of about 60% to about 70% greater than a diameter of the proximal frame portion, each of the proximal and distal frame portions having a substantially annular shape; and
  one or more valve leaflets having a body with a base and a flexible free edge, the valve leaflet base attached to the proximal frame portion within the lumen, the valve leaflet extending from the base, into the sinus region and terminating with the free edge before the maximum diameter of the bulbous portion so that the valve leaflet free edge is located within the sinus region, the valve leaflet defining a sinus pocket between each valve leaflet body and the bulbous frame portion, the valve leaflet moveable in response to fluid flow through the lumen between an open position during antegrade flow and a closed position during retrograde flow, wherein during retrograde flow each defined sinus pocket is adapted to enhance the movement of fluid flow within the sinus pocket such that fluid stagnation is inhibited;
  wherein the maximum diameter of the bulbous portion is positioned between the distal and proximal end of the bulbous portion such that a longitudinal distance from one of the proximal end and the distal end of the bulbous portion to the maximum diameter is less than a longitudinal distance from the other of the proximal end and the distal end of the bulbous portion to the maximum diameter; and
  wherein the frame comprises struts.

18. The implantable valve of claim 17, wherein the length of the valve leaflet is about 20% to about 50% of the diameter of the proximal frame portion.

19. The implantable valve of claim 18, wherein the bulbous portion has a proximal end connected to the proximal frame portion and a distal end connected to the distal frame portion, wherein the longitudinal distance along the longitudinal axis from the proximal end of the bulbous portion to the portion of the bulbous portion having the maximum diameter is about 60% to about 70% of the diameter of the proximal frame portion.

20. The implantable valve of claim 19, wherein the maximum diameter of the bulbous portion is approximately equal to the longitudinal distance between the proximal and distal ends of the bulbous portion.

* * * * *